(12) United States Patent
Kawamura et al.

(10) Patent No.: US 8,217,570 B2
(45) Date of Patent: Jul. 10, 2012

(54) ANTHRACENE DERIVATIVE AND ORGANIC ELECTROLUMINESCENT ELEMENT USING THE SAME

(75) Inventors: Masahiro Kawamura, Chiba (JP); Chishio Hosokawa, Chiba (JP)

(73) Assignee: Idemitsu Kosan Co., Ltd., Tokyo (JP)

( * ) Notice: Subject to any disclaimer, the term of this patent is extended or adjusted under 35 U.S.C. 154(b) by 774 days.

(21) Appl. No.: 11/722,609

(22) PCT Filed: Nov. 25, 2005

(86) PCT No.: PCT/JP2005/021664
§ 371 (c)(1),
(2), (4) Date: Jun. 22, 2007

(87) PCT Pub. No.: WO2006/067931
PCT Pub. Date: Jun. 29, 2006

(65) Prior Publication Data
US 2008/0111473 A1    May 15, 2008

(30) Foreign Application Priority Data
Dec. 22, 2004   (JP) .................................. 2004-371919

(51) Int. Cl.
*H01L 51/54* (2006.01)
*H05B 33/14* (2006.01)
*C09K 11/06* (2006.01)

(52) U.S. Cl. ........ 313/504; 313/506; 428/690; 428/917; 257/40; 257/E51.049

(58) Field of Classification Search .................. None
See application file for complete search history.

(56) References Cited

U.S. PATENT DOCUMENTS

| 5,077,142 | A | 12/1991 | Sakon et al. |
| 2001/0024738 | A1* | 9/2001 | Hawker et al. ............... 428/690 |
| 2003/0082402 | A1* | 5/2003 | Zheng et al. ............... 428/690 |
| 2006/0019116 | A1 | 1/2006 | Conley et al. |
| 2007/0200490 | A1 | 8/2007 | Kawamura et al. |

FOREIGN PATENT DOCUMENTS

| JP | 3-200889 | 9/1991 |
| JP | 7-138561 | 5/1995 |
| JP | 8-239655 | 9/1996 |
| JP | 2004 2297 | 1/2004 |
| JP | 2005 120296 | 5/2005 |
| WO | 03 060956 | 7/2003 |
| WO | 2005 097756 | 10/2005 |

OTHER PUBLICATIONS

Yamamoto et al., JP (2004)-002297, machine assisted translation.*
C. W. Tang, et al., "Organic Electroluminescent Diodes", Applied Physics Letters, vol. 51, No. 12, Sep. 21, 1987, pp. 913-915.
Itoh, T. et al.,"Preparation of Copper Ion Compexes of Sterilically Congested Diaryldiazomethanes Having a Pyridine Ligand and Characterization of Their Photoproducts", J. Am. Chem. Soc., vol. 127, No. 19, pp. 7079-7093, 2005.
U.S. Appl. No. 13/375,020, filed Nov. 29, 2011, Kawamura, et al.

* cited by examiner

*Primary Examiner* — Jennifer Chriss
*Assistant Examiner* — Brett A Crouse
(74) *Attorney, Agent, or Firm* — Oblon, Spivak, McClelland, Maier & Neustadt, L.L.P.

(57) ABSTRACT

Provided are an anthracene derivative having a heteroaryl group containing a nitrogen-containing six-membered ring and having a specific structure and an organic electroluminescence device in which an organic thin film layer comprising a single layer or plural layers including at least a light emitting layer is interposed between a cathode and an anode, wherein at least one layer in the above organic thin film layer contains the anthracene derivative described above in the form of a single component or a mixed component. Provided are the organic electroluminescence device in which homogeneous light emission is obtained over a long period of time and which has a long lifetime and the anthracene derivative which materializes the same.

16 Claims, No Drawings

ANTHRACENE DERIVATIVE AND ORGANIC ELECTROLUMINESCENT ELEMENT USING THE SAME

BACKGROUND OF THE INVENTION

The present invention relates to an anthracene derivative and an organic electroluminescence device obtained by using the same, more specifically to an organic electroluminescence device which provides homogeneous light emission over a long period of time and which has a long lifetime and a novel anthracene derivative which materializes the same.

RELATED ART

An organic electroluminescence (EL) device is a spontaneous light emitting device making use of the principle that a fluorescent substance emits light by recombination energy of holes injected from an anode and electrons injected from a cathode by applying an electric field. Since organic EL device of a laminate type driven at a low voltage was reported by C. W. Tang et al. of Eastman Kodak Company (C. W. Tang and S. A. Vanslyke, Applied Physics Letters, Vol. 51, p. 915, 1987 and the like), researches on organic EL devices comprising organic materials as structural materials have actively been carried out. Tang et al. use tris(8-quinolinolatealuminum) or the light emitting layer and a triphenyldiamine derivative for the hole transporting layer. The advantages of a laminate structure include an elevation in an efficiency of injecting holes into a light emitting layer, a rise in a production efficiency of excitons produced by blocking electrons injected from a cathode to recombine them and shutting up of excitons produced in a light emitting layer. As shown in the above example, a two-layer type comprising a hole transporting (injecting) layer and an electron transporting and light emitting layer and a three-layered type comprising a hole transporting (injecting) layer, a light emitting layer and an electron transporting (injecting) layer are well known as the device structures of an organic EL device. In such laminate type structural devices, device structures and forming methods are studied in order to enhance a recombination efficiency of holes and electrons injected.

Known as light emitting materials for an organic EL device are light emitting materials including chelate complexes such as a tris(8-quinolinolate)aluminum complex, coumarin derivatives, tetraphenylbutadiene derivatives, distyrylarylene derivatives, oxadiazole derivatives and the like. It is reported that light emission of a blue color to a red color in a visible region is obtained from them, and it is expected that color display devices are materialized (refer to for example, patent documents 1 to 3).

Further, in recent years, it has been tried to provide an electron injecting layer in an organic EL device to enhance a current efficiency. However, involved therein were the defects that exciplexes were observed to be formed and that light emission at a high luminance was obtained but the lifetime was short. Also, separation between a metal electrode and an organic layer was brought about by current application over a long period of time, and an organic layer and an electrode were crystallized and clouded so that the above phenomena had to be prevented. It is described in a patent document 4 as trial for solving the above matters to use pyrazine compounds, quinoline compounds and quinoxaline compounds, for example, 2,3,5,6-tetraphenylpyrazine, 2,3,4-triphenylquinoline and 2,3-diphenylquinoxaline as constitutional components for an organic EL device. However, involved therein was the problem that the above compounds had a low melting point and therefore were crystallized soon when used for an amorphous thin film layer in an organic EL device to scarcely emit light. Further, brought about was the problem that separation between a metal electrode and an organic layer was caused by current application to shorten a lifetime of the organic EL device.

Patent document 1: Japanese Patent Application Laid-Open No. 239655/1996
Patent document 2: Japanese Patent Application Laid-Open No. 183561/1995
Patent document 3: Japanese Patent Application Laid-Open No. 200889/1991
Patent document 4: U.S. Pat. No. 5,077,142

DISCLOSURE OF THE INVENTION

The present invention has been made in order to solve the problems described above, and an object thereof is to provide an organic EL device in which homogeneous light emission is obtained over a long period of time and which has a long lifetime and an anthracene derivative which materializes the same.

Intensive researches repeated by the present inventors in order to achieve the object described above have resulted in finding that the above object can be achieved by using an anthracene derivative having a heteroaryl group containing a nitrogen-containing six-membered ring and having a specific structure as a material for an organic EL device, and thus the present inventors have completed the present invention.

That is the present invention provides an anthracene derivative represented by the following Formula (1) or (2):

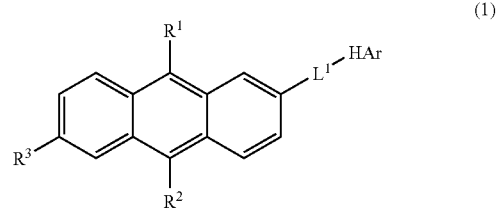

(wherein $R^1$ to $R^3$ each represent independently a hydrogen atom, a halogen atom, a substituted or non-substituted aliphatic hydrocarbon group having 1 to 40 carbon atoms, a substituted or non-substituted aryl group having 5 to 60 carbon atoms or a substituted or non-substituted heteroaryl group having 3 to 60 carbon atoms; provided that $R^1$ and $R^2$ are not hydrogen atoms at the same time;

$L^1$ to $L^3$ each represent independently a single bond, a substituted or non-substituted divalent aliphatic hydrocarbon group having 1 to 40 carbon atoms, a substituted or non-substituted arylene group having 5 to 60 carbon atoms or a substituted or non-substituted heteroarylene group having 3 to 60 carbon atoms; and HAr represents a substituted or non-substituted heteroaryl group which has 3 to 60 carbon atoms and contains a nitrogen-containing six-membered ring).

Further, the present invention provides an organic EL device in which an organic thin layer comprising a single layer or plural layers comprising at least a light emitting layer is interposed between a cathode and an anode, wherein at least one layer in the above organic thin layer contains the anthracene derivative of the present invention in the form of a single component or a mixed component.

The anthracene derivative of the present invention and the organic EL device obtained by using the same provide homogeneous light emission over a long period of time and have a long lifetime.

BEST MODE FOR CARRYING OUT THE INVENTION

The anthracene derivative of the present invention is an anthracene derivative represented by the following Formula (1) or (2).

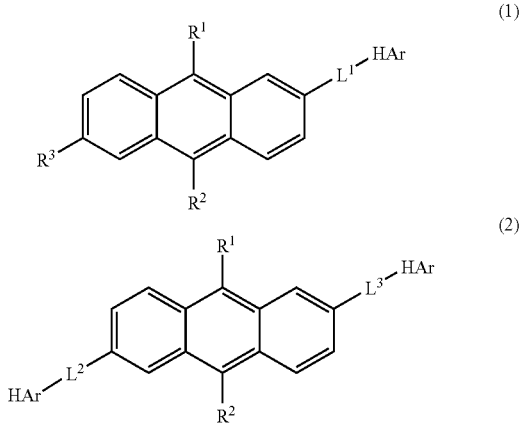

In Formulas (1) and (2), $R^1$ to $R^3$ each are independently preferably a hydrogen atom, a halogen atom, a substituted or non-substituted aliphatic hydrocarbon group having 1 to 40 carbon atoms, a substituted or non-substituted aryl group having 5 to 60 carbon atoms or a substituted or non-substituted heteroaryl group having 3 to 60 carbon atoms, provided that $R^1$ and $R^2$ are not hydrogen atoms at the same time.

The halogen atom represented by $R^1$ to $R^3$ includes, for examples fluorine, chlorine, bromine and iodine.

The substituted or non-substituted aliphatic hydrocarbon group having 1 to 40 carbon atoms represented by $R^1$ to $R^3$ includes an alkyl group having 1 to 40 carbon atoms, an alkenyl group having 2 to 40 carbon atoms and an alkynyl group having 2 to 40 carbon atoms. The alkyl group includes, for example, methyl, ethyl, 1-propyl, 2-propyl, 1-butyl, 2-butyl, s-butyl, t-butyl, pentyl, hexyl, octyl, decyl, dodecyl, 2-ethylhexyl, 3,7-dimethyloctyl, cyclopropyl, cyclopentyl, cyclohexyl, 1-adamantyl, 2-adamantyl, norbornyl, trifluoromethyl, trichloromethyl and the like. It is preferably methyl, ethyl, 1-propyl, 2-propyl, 1-butyl, 2-butyl, s-butyl or t-butyl. The alkenyl group includes vinyl, propenyl, butenyl, oleyl, eicosapentaenyl, docosahexaenyl and the like, and it is preferably vinyl or propenyl. The alkynyl group includes ethynyl, methylethynyl and the like, and it is preferably ethynyl.

Substituents for the aliphatic hydrocarbon group described above include, for example, an aryl group (having preferably 6 to 30 carbon atoms, more preferably 6 to 20 carbon atoms and particularly preferably 6 to 12 carbon atoms and including, for example, phenyl, p-methylphenyl, naphthyl and the like), an amino group (having preferably 0 to 20 carbon atoms, more preferably 0 to 12 carbon atoms and particularly preferably 0 to 6 carbon atoms and including, for example, amino, methylamino, dimethylamino, diethylamino, diphenylamino, dibenzylamino and the like), an alkoxy group (having preferably 1 to 20 carbon atoms, more preferably 1 to 12 carbon atoms and particularly preferably 1 to 8 carbon atoms and including, for example, methoxy, ethoxy, butoxy and the like), an aryloxy group (having preferably 6 to 20 carbon atoms, more preferably 6 to 16 carbon atoms and particularly preferably 6 to 12 carbon atoms and including, for example, phenyloxy, 2-naphthyloxy and the like), an acyl group (having preferably 1 to 20 carbon atoms, more preferably 1 to 16 carbon atoms and particularly preferably 1 to 12 carbon atoms and including, for example, acetyl, benzoyl, formyl, pivaloyl and the like), an alkoxycarbonyl group (having preferably 2 to 20 carbon atoms, more preferably 2 to 16 carbon atoms and particularly preferably 2 to 12 carbon atoms and including, for example, methoxycarbonyl, ethoxycarbonyl and the like), an aryloxycarbonyl group (having preferably 7 to 20 carbon atoms, more preferably 7 to 16 carbon atoms and particularly preferably 7 to 10 carbon atoms and including, for example, phenyloxycarbonyl and the like), an acyloxy group (having preferably 2 to 20 carbon atoms, more preferably 2 to 16 carbon atoms and particularly preferably 2 to 10 carbon atoms and including, for example, acetoxy, benzoyloxy and the like), an acylamino group (having preferably 2 to 20 carbon atoms, more preferably 2 to 16 carbon atoms and particularly preferably 2 to 10 carbon atoms and including, for example, acetylamino, benzoylamino and the like), an alkoxycarbonylamino group (having preferably 2 to 20 carbon atoms, more preferably 2 to 16 carbon atoms and particularly preferably 2 to 12 carbon atoms and including, for example, methoxycarbonylamino and the like), an aryloxycarbonylamino group (having preferably 7 to 20 carbon atoms, more preferably 7 to 16 carbon atoms and particularly preferably 7 to 12 carbon atoms and Including, for example, phenyloxycarbonylamino and the like), a sulfonylamino group (having preferably 1 to 20 carbon atoms, more preferably 1 to 16 carbon atoms and particularly preferably 1 to 12 carbon atoms and including, for example, methanesulfonylamino, benzenesulfonylamino and the like), a sulfamoyl group (having preferably 0 to 20 carbon atoms, more preferably 0 to 16 carbon atoms and particularly preferably 0 to 12 carbon atoms and including, for example, sulfamoyl, methylsulfamoyl dimethylsulfamoyl, phenylsulfamoyl and the like), a carbamoyl group (having preferably 1 to 20 carbon atoms, more preferably 1 to 16 carbon atoms and particularly preferably 1 to 12 carbon atoms and including, for example, carbamoyl, methylcarbamoyl, diethylcarbamoyl, phenylcarbamoyl and the like), an alkylthio group (having preferably 1 to 20 carbon atoms, more preferably 1 to 16 carbon atoms and particularly preferably 1 to 12 carbon atoms and including, for example, methylthio, ethylthio and the like), an arylthio group (having preferably 6 to 20 carbon atoms, more preferably 6 to 16 carbon atoms and particularly preferably 6 to 12 carbon atoms and including, for example, phenylthio and the like), a sulfonyl group (having preferably 1 to 20 carbon atoms, more preferably 1 to 16 carbon atoms and particularly preferably 1 to 12 carbon atoms and including, for example, mesyl, tosyl and the like), a sulfinyl group (having preferably 1 to 20 carbon atoms, more preferably 1 to 16 carbon atoms and particularly preferably 1 to 12 carbon atoms and including, for example, methanesulfinyl, benzenesulfinyl and the like), a ureido group (having preferably 1 to 20 carbon atoms, more preferably 1 to 16 carbon atoms and particularly preferably 1 to 12 carbon atoms and including, for example, ureido methylureido, phenylureido and the like), a phosphoric amide group (having preferably 1 to 20 carbon atoms, more preferably 1 to 16 carbon atoms and particularly preferably 1 to 12 carbon atoms and including, for example, diethylphosphoric amide, phenylphosphoric am-de and the like), a hydroxy group a mercapto group, a halogen atom (for example, a fluorine atom, a chlorine atom, a bromine atom and an iodine atom), a cyano group, a sulfo group, a carboxyl group, a nitro group, a hydroxamic acid group, a sulfino group, a hydrazino group, an imino group, a heterocyclic group (having preferably 1 to 30 carbon atoms, more preferably 1 to 12 carbon atoms containing, for example, a nitrogen atom, an oxygen atom and a sulfur atom as a hetero atom and, to be specific including, for example, imidazolyl, pyridyl, quinolyl, furyl, thienyl, piperidyl, morpholino, benzoxazolyl, benzimidazolyl, benzothiazolyl, carbazolyl and the like) and a silyl group (having preferably 3 to 40 carbon atoms, more preferably 3 to 30 carbon atoms and particularly preferably 3 to 24 carbon atoms and including, for example, trimethylsilyl, triphenylsilyl and the like). The above substituents may further be substituted. When two or more substituents are present, they may be the same or different. If possible, they may be combined with each other to form rings.

The substituted or non-substituted aryl group having 5 to 60 carbon atoms represented by $R^1$ to $R^3$ includes, for example, phenyl, 2-biphenylyl, 3-biphenylyl, 4-biphenylyl, terphenylyl, 3,5-diphenylphenyl, 3,4-diphenylphenyl, pentaphenylphenyl, fluorenyl, 1-naphthyl, 2-naphthyl, 9-anthryl, 2-anthryl, 9-phenanthryl, 1-pyrenyl, chrysenyl, naphthacenyl, coronyl, 10-phenyl-anthracene-9-yl, 10-naphthalene-2-yl-anthracene-9-yl, 12-phenyl-chrysene-6-yl, (10-phenyl-anthracene-9-yl)-4-phenyl, (10-naphthalene-2-yl-anthracene-9-yl)-4-phenyl, fluorenyl, 9,9'-dimethylfluorene-2-yl, a spiro aromatic ring group and the like.

The spiro aromatic ring group is preferably a compound represented by the following Formula (A):

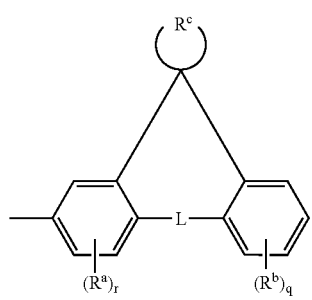

(A)

(wherein $R^a$ to $R^b$ each are independently a hydrogen atom, a substituted or non-substituted amino group, a substituted or non-substituted alkyl group having 1 to 50 carbon atoms, a substituted or non-substituted aryl group having 6 to 40 carbon atoms or a substituted or non-substituted heterocyclic group having 5 to 40 carbon atoms; $R^c$ represents an atomic group forming a cyclic structure; L is a single bond, —O—, —S—, —NR'— or —CR''R'''— (R', —R'' and R''' each are independently a substituted or non-substituted alkyl group having 1 to 50 carbon atoms or a substituted or non-substituted aryl group having 6 to 40 carbon atoms); s, q and r each are an integer of 0 to 2; and $R^a$ and $R^b$ may be combined with each other to form a ring) includes, for example, spiro(cyclohexane-1,9'-fluorene)-2'-yl, spiro(cyclopentane-1,9'-fluorene)-2'-yl, spiro(indene-1,9'-fluorene)-2'-yl, dispiro(bis-fluorene-9,10,9',9''-9,9,10,10-tetrahydroanthracene)-2-yl, dispiro(bisfluorene-9,10,9',9''-9,9,10,10-tetrahydroanthracene)-2'-yl, 9,9'-spirobifluorene-2-yl and the like.

Substituents for the aryl group described above include, for example, an alkyl group (having preferably 1 to 20 carbon atoms, more preferably 1 to 12 carbon atoms and particularly preferably 1 to 8 carbon atoms and including, for example, methyl, ethyl, i-propyl, t-butyl, n-octyl, n-decyl, n-hexadecyl, cyclopropyl, cyclopentyl, cyclohexyl and the like), an alkenyl group (having preferably 2 to 20 carbon atoms, more preferably 2 to 12 carbon atoms and particularly preferably 2 to 8 carbon atoms and including, for example, vinyl, allyl, 2-butenyl, 3-pent ethyl and the like), an alkynyl group (having preferably 2 to 20 carbon atoms, more preferably 2 to 12 carbon atoms and particularly preferably 2 to 8 carbon atoms and including, for example, propargyl, 3-pentynyl and the like), an amino group (having preferably 0 to 20 carbon atoms, more preferably 0 to 12 carbon atoms and particularly preferably 0 to 6 carbon atoms and including, for example, amino, methylamino, dimethylamino, diethylamino, diphenylamino, dibenzylamino and the like), an alkoxy group (having preferably 1 to 20 carbon atoms, more preferably 1 to 12 carbon atoms and particularly preferably 1 to 8 carbon atoms and including, for example, methoxy, ethoxy, butoxy and the like), an aryloxy group (having preferably 6 to 20 carbon atoms, more preferably 6 to 16 carbon atoms and particularly preferably 6 to 12 carbon atoms and including, for example, phenyloxy, 2-naphthyloxy and the like), an acyl group (having preferably 1 to 20 carbon atoms, more preferably 1 to 16 carbon atoms and particularly preferably 1 to 12 carbon atoms and including, for example, acetyl, benzoyl, formyl, pivaloyl and the like), an alkoxycarbonyl group (having preferably 2 to 20 carbon atoms, more preferably 2 to 16 carbon atoms and particularly preferably 2 to 12 carbon atoms and including a for example, methoxycarbonyl, ethoxycarbonyl and the like), an aryloxycarbonyl group (having preferably 7 to 20 carbon atoms, more preferably 7 to 16 carbon atoms and particularly preferably 7 to 10 carbon atoms and including, for example, phenyloxycarbonyl and the like), an acyloxy group (having preferably 2 to 20 carbon atoms, more preferably 2 to 16 carbon atoms and particularly preferably 2 to 10 carbon atoms and Including for example, acetoxy, benzoyloxy and the like), an acylamino group (having preferably 2 to 20 carbon atoms, more preferably 2 to 16 carbon atoms and particularly preferably 2 to 10 carbon atoms and including, for example, acetylamino, benzoylamino and the like), an alkoxycarbonylamino group (having preferably 2 to 20 carbon atoms more preferably 2 to 16 carbon atoms and particularly preferably 2 to 12 carbon atoms and including for example, methoxycarbonylamino and the like), an aryloxycarbonylamino group (having preferably 7 to 20 carbon atoms, more preferably 7 to 16 carbon atoms and particularly preferably 7 to 12 carbon atoms and including, for example, phenyloxycarbonylamino and the like), a sulfonylamino group (having preferably 1 to 20 carbon atoms, more preferably 1 to 16 carbon atoms and particularly preferably 1 to 12 carbon atoms and including, for example, methanesulfonylamino, benzenesulfonylamino and the like), a sulfamoyl group (having preferably 0 to 20 carbon atoms, more preferably 0 to 16 carbon atoms and particularly preferably 0 to 12 carbon atoms and including, for example, sulfamoyl, methylsulfamoyl, dimethylsulfamoyl, phenylsulfamoyl and the like), a carbamoyl group (having preferably 1 to 20 carbon atoms, more preferably to 16 carbon atoms and particularly preferably 1 to 12 carbon atoms and including, for example, carbamoyl, methylcarbamoyl, diethylcarbamoyl, phenylcarbamoyl and the like) an alkylthio group (having preferably 1 to 20 carbon atoms, more preferably 1 to 16 carbon atoms and particularly preferably 1 to 12 carbon atoms and including, for example, methylthio, ethylthio and the like), an arylthio group (having preferably 6 to 20 carbon atoms, more preferably 6 to 16 carbon atoms and particularly preferably 6 to 12 carbon atoms and including, for example, phenylthio and the like), a sulfonyl group (having preferably 1 to 20 carbon atoms, more preferably 1 to 16 carbon atoms and particularly preferably 1 to 12 carbon atoms and including, for example, mesyl, tosyl and the like), a sulfinyl group (having preferably 1 to 20 carbon atoms, more preferably 1 to 16 carbon atoms and particularly preferably 1 to 12 carbon atoms and including, for example, methanesulfinyl, benzenesulfinyl and the like), a ureido group (having preferably 1 to 20 carbon atoms, more preferably 1 to 16 carbon atoms and particularly preferably 1 to 12 carbon atoms and including, for example, ureido methylureido, phenylureido and the like), a phosphoric amide group (having preferably 1 to 20 carbon atoms, more preferably 1 to 16 carbon atoms and particularly preferably 1 to 12 carbon atoms and including, for example, diethylphosphoric amide, phenylphosphoric amide and the like) a hydroxy group, a mercapto group, a halogen atom (for example, a fluorine atom, a chlorine atom, a bromine atom and an iodine atom), a cyano group, a sulfo group, a carboxyl group, a nitro group, a hydroxamic acid group, a sulfino group, a hydrazino group, an imino group, a heterocyclic group (having preferably 1 to 30 carbon atoms, more preferably 1 to 12 carbon atoms, containing, for example, a nitrogen atom, an oxygen atom and a sulfur atom as a hetero atom and, to be specific, including, for example, imidazolyl, pyridyl, quinolyl, furyl, thienyl piperidyl, morpholino, benzoxazolyl, benzimidazolyl, benzothiazolyl, carbazolyl and the like) and a silyl group (having preferably 3 to 40 carbon atoms, more preferably 3 to 30 carbon atoms and particularly preferably 3 to 24 carbon atoms and including, for example, trimethylsilyl, triphenylsilyl and the like). The above substituents may further be substituted. When two or more substituents are present they may be the same or different. If possible, they may be combined with each other to form rings.

The substituted or non-substituted heteroaryl group having 3 to 60 carbon atoms represented by $R^1$ to $R^3$ includes, for example, monovalent residues of furan, thiophene, pyrrole, imidazole, pyrazole, triazole, oxadiazole, pyridine, pyrazine, triazine, pyrimidine, benzofuran, dibenzofuran, benzothiophene, dibenzothiophene, carbazole, benzimidazole, imidazopyridine and the like.

Further, substituents for the heteroaryl group described above include the same groups as the substituents for the aryl group described above.

In Formulas (1) and (2), $L^1$ to $L^3$ each are independently preferably a single bond, a substituted or non-substituted divalent aliphatic hydrocarbon group having 1 to 40 carbon atoms, a substituted or non-substituted arylene group having 5 to 60 carbon atoms or a substituted or non-substituted heteroarylene group having 3 to 60 carbon atoms.

The substituted or non-substituted divalent aliphatic hydrocarbon group having 1 to 40 carbon atoms represented by $L^1$ to $L^3$ includes, for example, methylene, propylene, butylene, vinylene, ethynylene and the like, and it is preferably methylene. Substituents for the above aliphatic hydrocarbon group include the same groups as the substituents for the aliphatic hydrocarbon group described above represented by $R^1$ to $R^3$.

The substituted or non-substituted arylene group having 5 to 60 carbon atoms represented by $L^1$ to $L^3$ includes, for example, phenylene, naphthylene, anthrylene, biphenylene, terphenylene, pyrenylene, chrysenylene, fluorenylene, spirofluorenylene and the like, and it is preferably phenylene. Substituents for the above arylene group include the same groups as the substituents for the aryl group described above represented by $R^1$ to $R^3$.

The substituted or non-substituted heteroarylene group having 3 to 60 carbon atoms represented by $L^1$ to $L^3$ includes, for example, di-valent residues of thiophene, furan, selenophene, pyridine, pyrazine, pyrimidine, oxadiazole, thiadiazole, oxazole, thiazole, triazole and the like. It is preferably the divalent residues of thiophene, pyridine, oxadiazole and triazole. Substituents for the above heteroarylene group include the same groups as the substituents for the aryl group described above represented by $R^1$ to $R^3$.

In Formulas (1) and (2), the substituted or non-substituted heteroaryl group represented by HAr which has 3 to 60 carbon atoms and contains a nitrogen-containing six-membered ring includes, for example, monovalent residues of pyridine, pyrazine, triazine, pyrimidine, quinoxaline, quinazoline, quinoline, phenanthroline and the like, and it is preferably a group represented by:

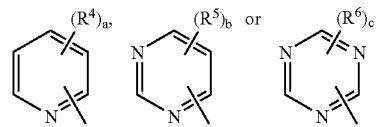

(wherein $R^4$ to $R^6$ each represent independently a hydrogen atom, a halogen atom, a substituted or non-substituted aliphatic hydrocarbon group having 1 to 40 carbon atoms, a substituted or non-substituted aryl group having 5 to 60 carbon atoms or a substituted or non-substituted heteroaryl group having 3 to 60 carbon atoms, and the specific examples of the above respective groups include the same groups as given in $R^1$ to $R^3$ described above;

plural adjacent $R^4$ and $R^5$ may be combined to form a cyclic structure, and the cyclic structure includes, for example, cycloalkanes having 4 to 12 carbon atoms such as cyclobutane, cyclopentane, cyclohexane, adamantane, norbornane and the like, cycloalkenes having 4 to 12 carbon atoms such as cyclobutene, cyclopentene, cyclohexene, cycloheptene, cyclooctene and the like, cycloalkadienes having 6 to 12 carbon atoms such as cyclohexadiene, cycloheptadiene, cyclooctadiene and the like and aromatic rings having 6 to 50 carbon atoms such as benzene, naphthalene, phenanthrene, anthracene, pyrene, chrysene, acenaphthylene and the like;

a represents an integer of 0 to 4; b represents an integer of 0 to 3; and c represents an integer of 0 to 2).

Substituents for the heteroarylene group described above include the same groups as the substituents for the aryl group described above represented by $R^1$ to $R^3$.

The anthracene derivative of the present invention can be used as a material for an organic EL device, particularly an electron injecting and transporting material for an organic EL device and an electron transporting material for an electrophotographic photoreceptor, and it is preferably used as a material for an organic EL device.

The specific examples of the anthracene derivative of the present invention represented by Formula (1) or (2) are shown below, but they shall not be restricted to these compounds shown as the examples.

9
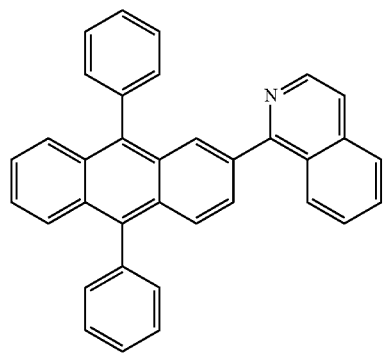
10
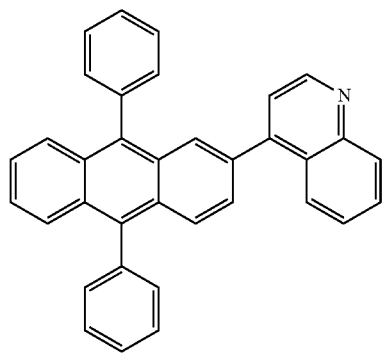
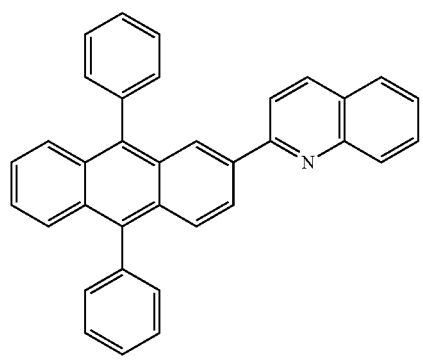
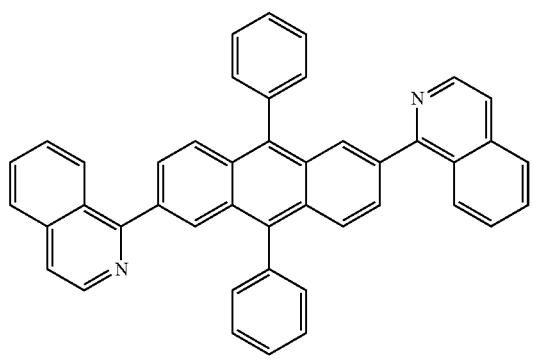
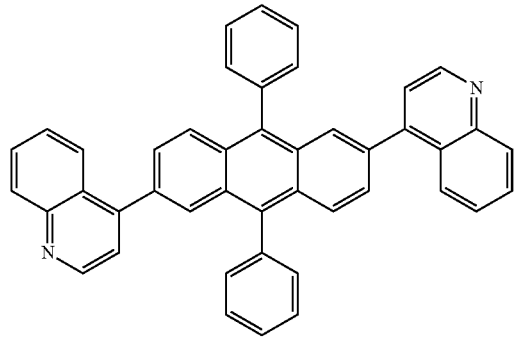
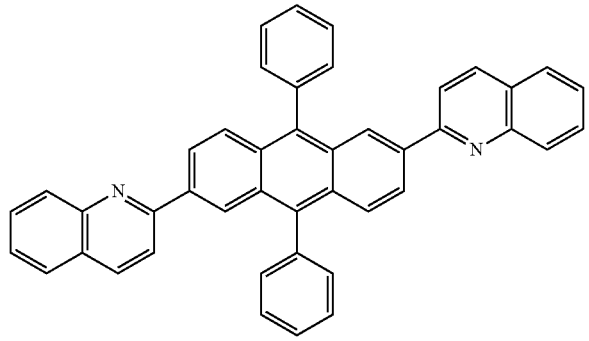
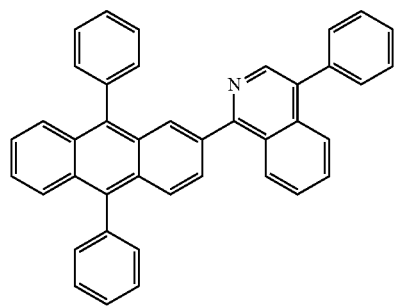
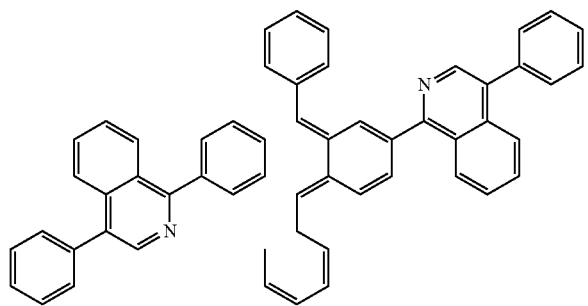

-continued
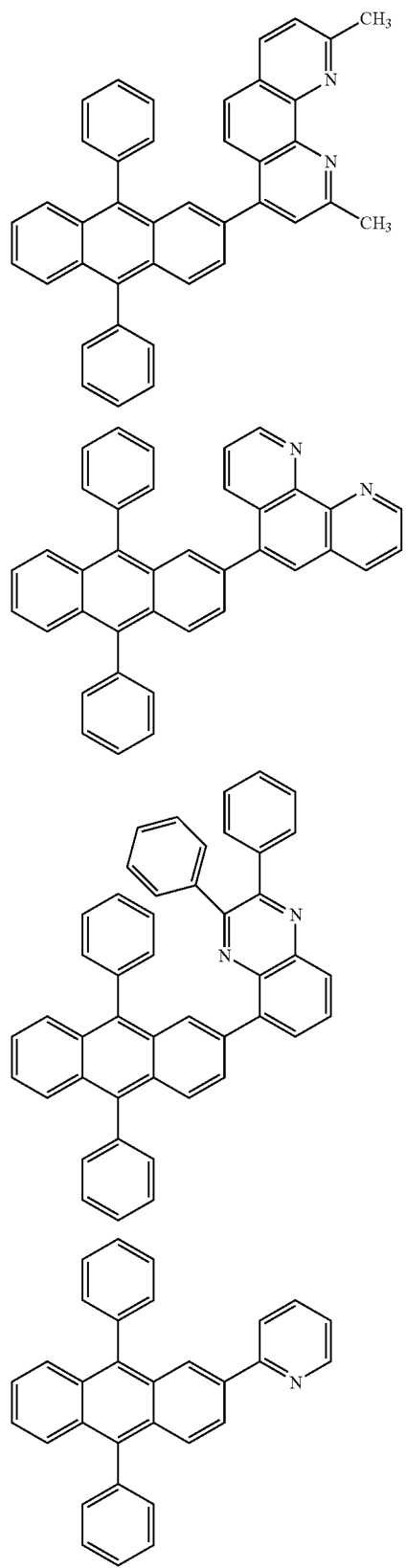
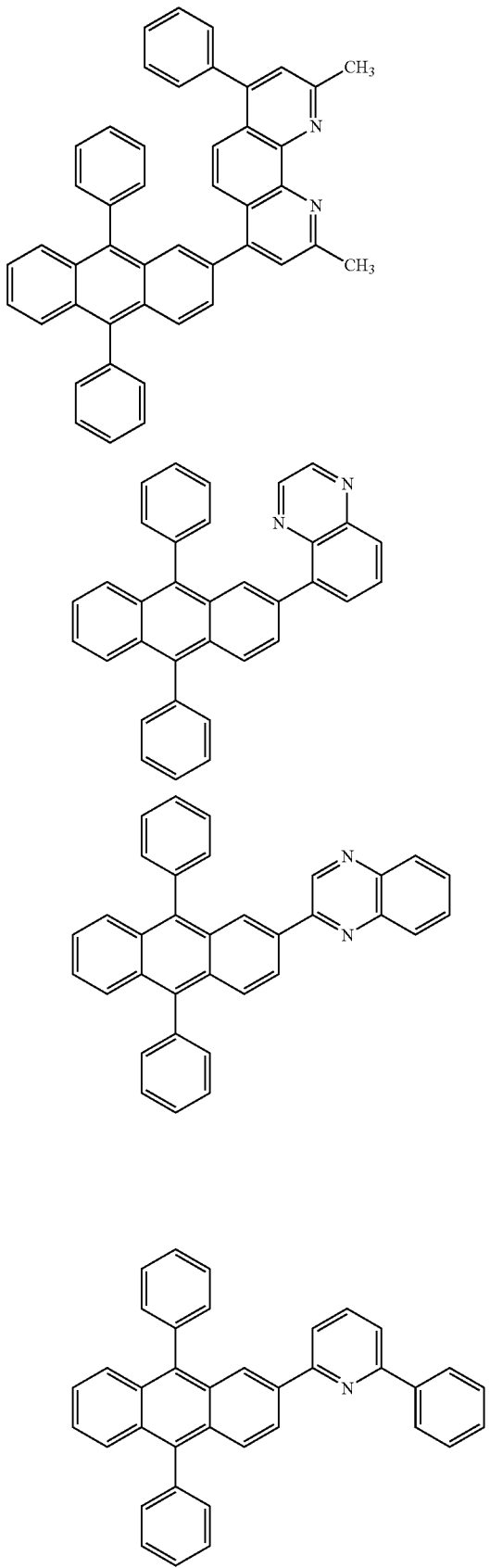

13
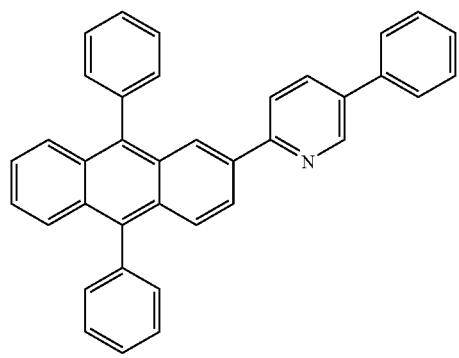
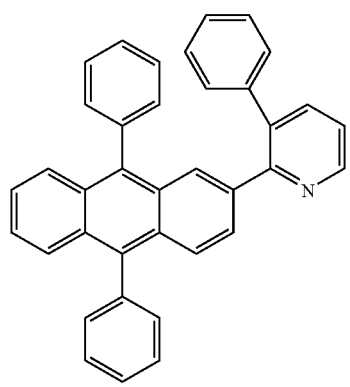
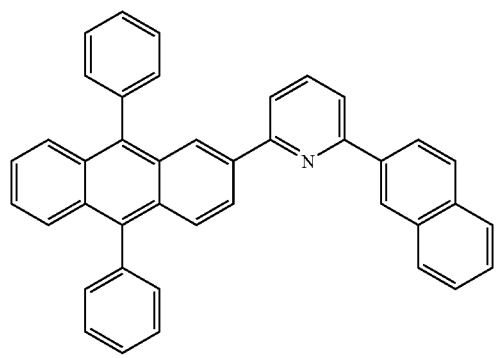
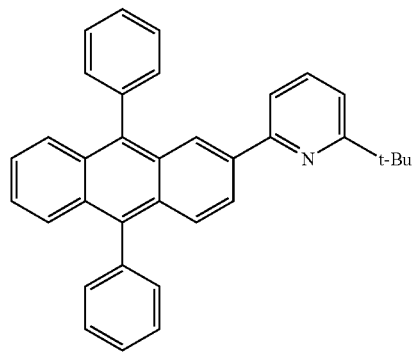
14
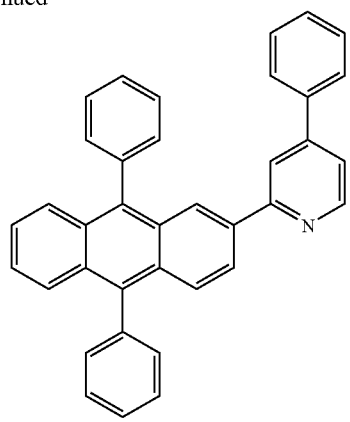
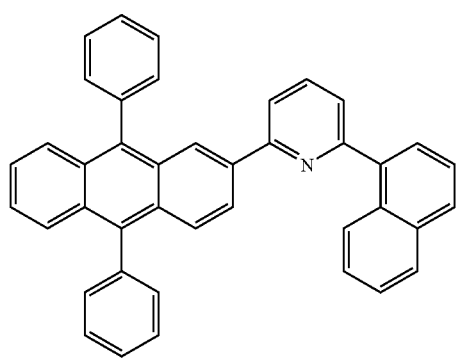
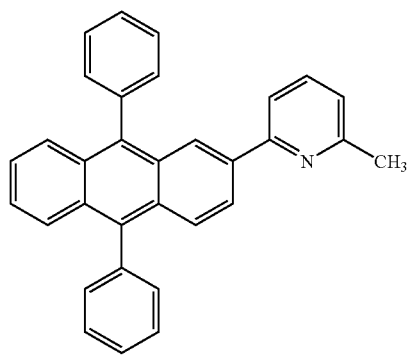
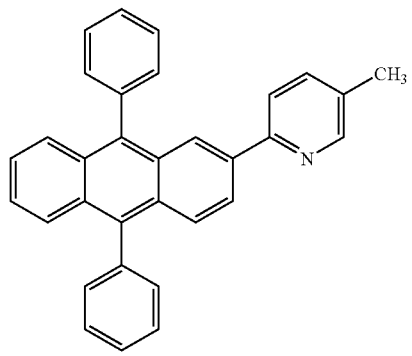

-continued
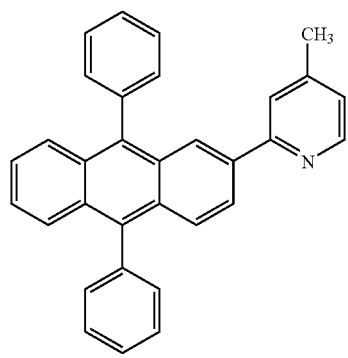
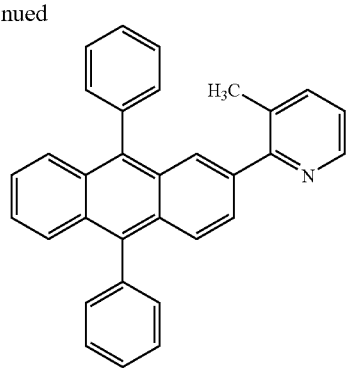
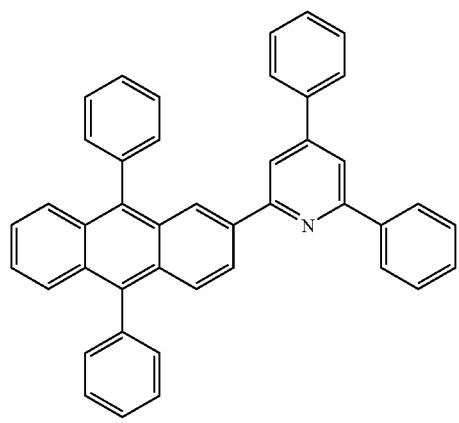
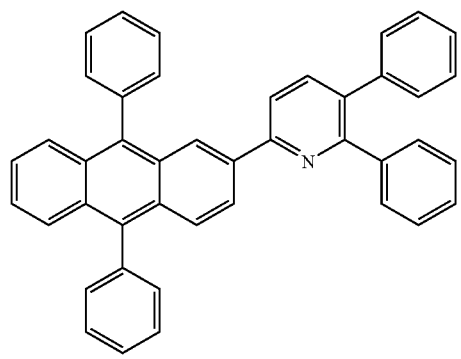
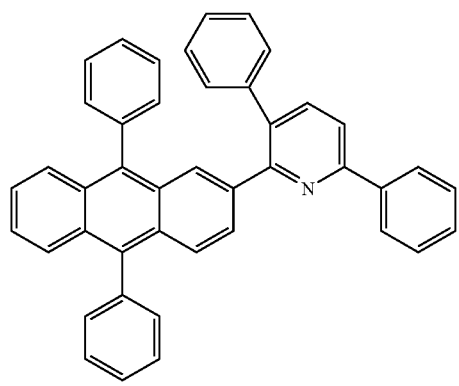
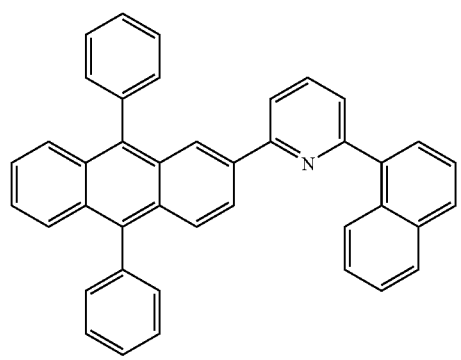
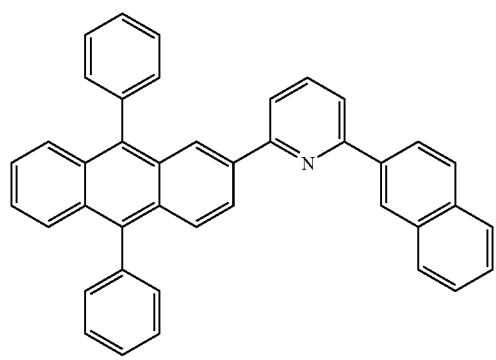
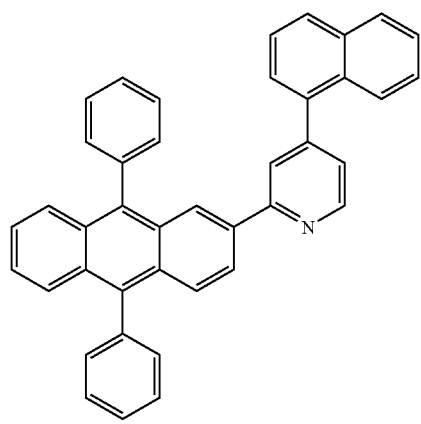

-continued
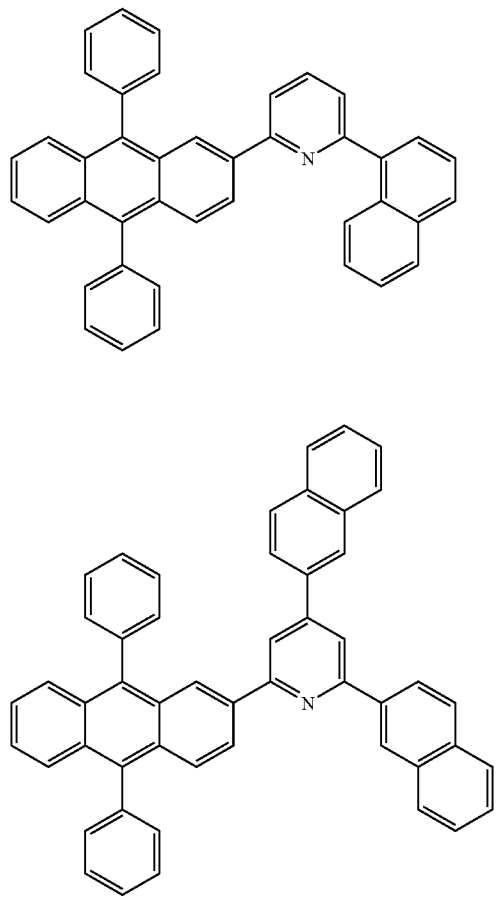
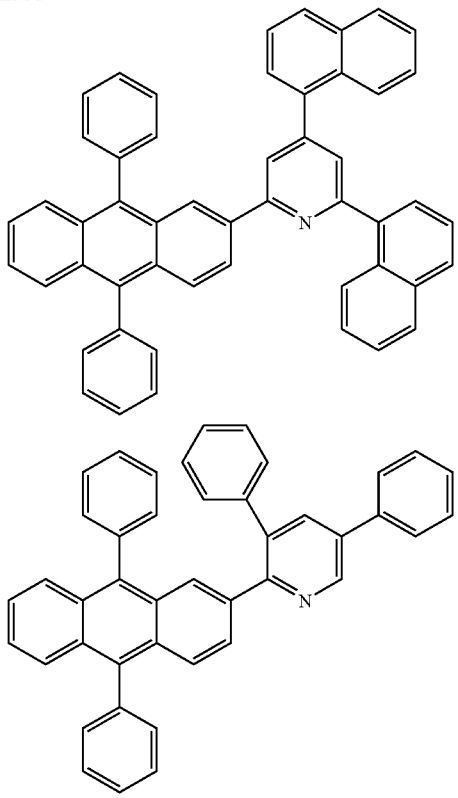
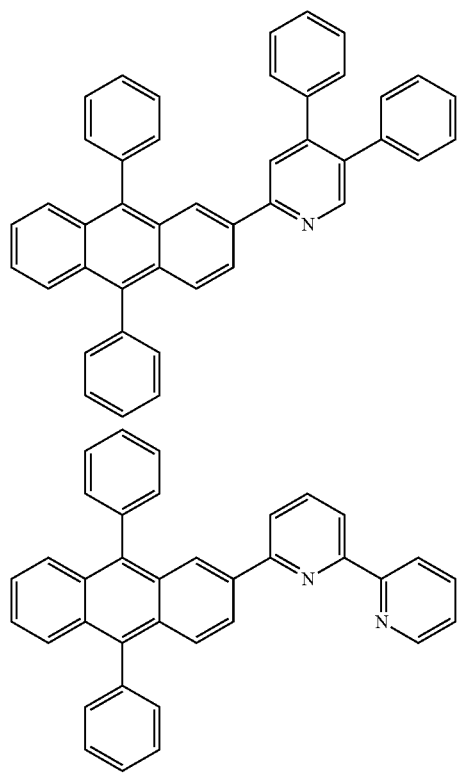
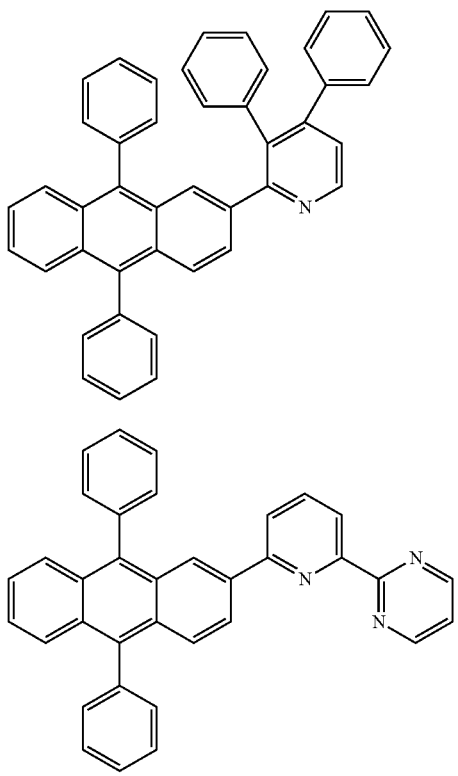

-continued
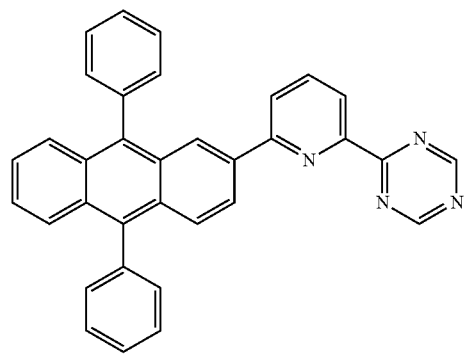
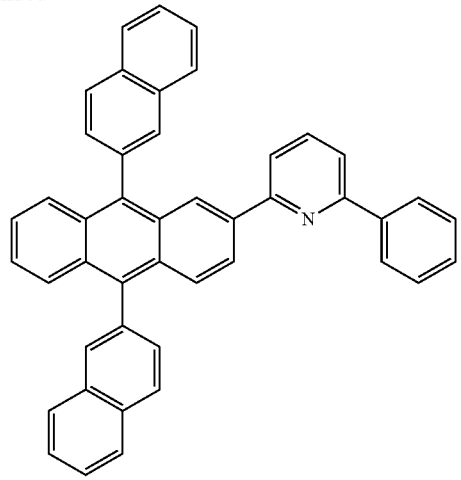
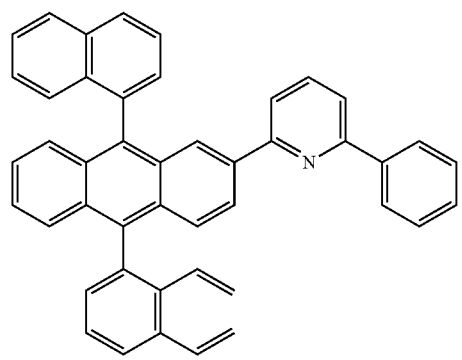
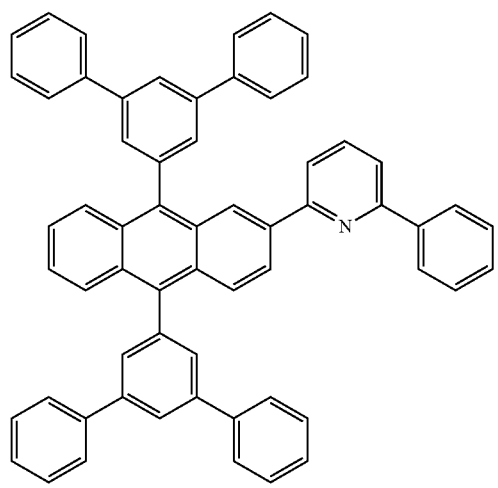
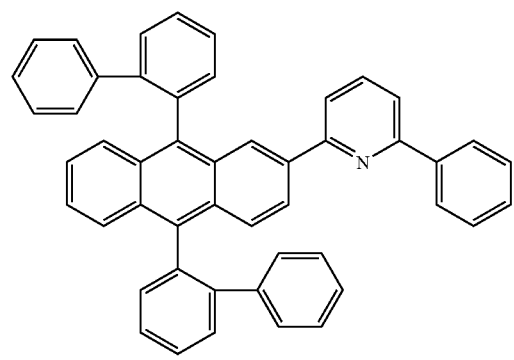
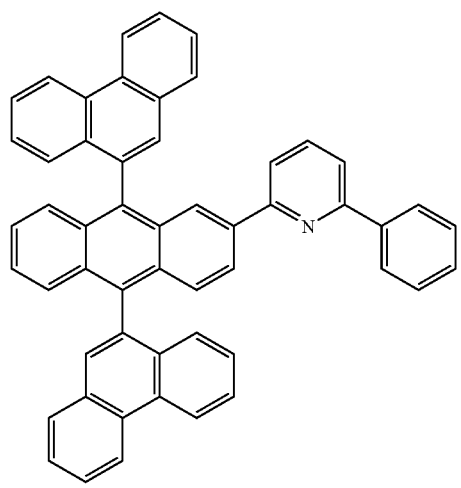

-continued
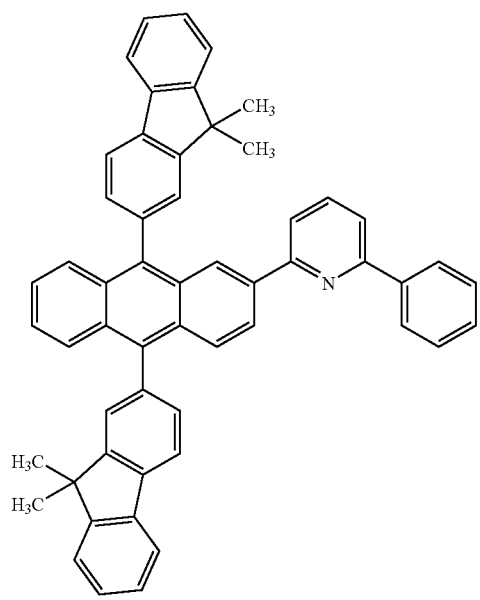
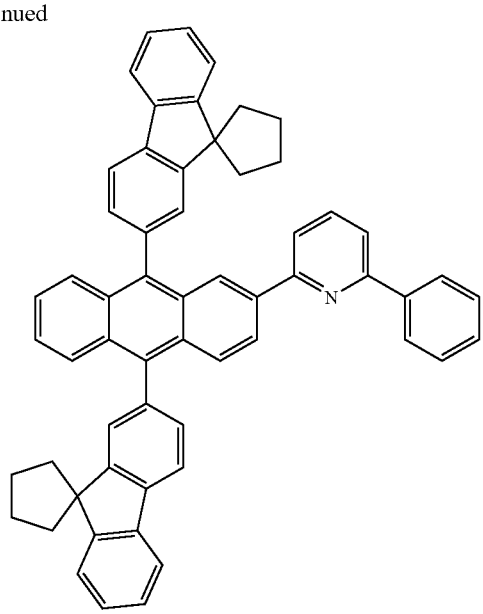
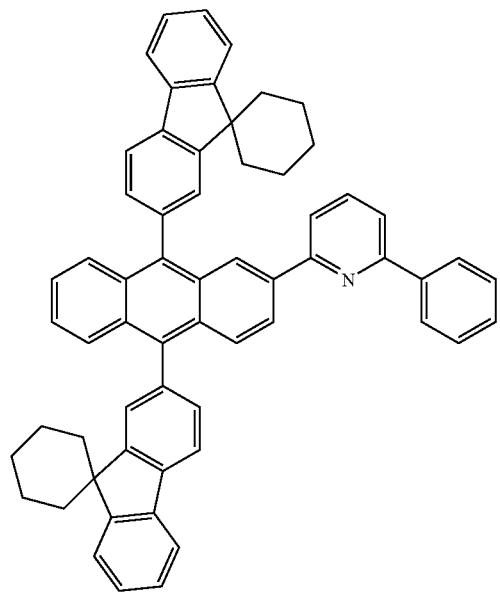
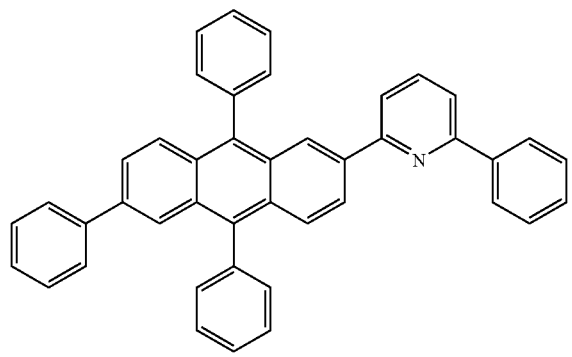
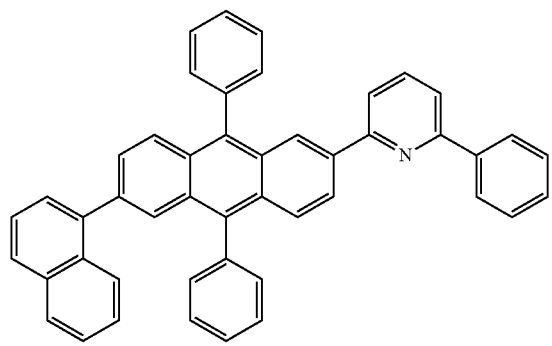
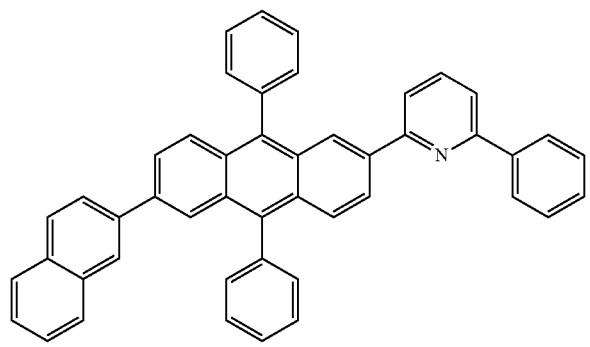

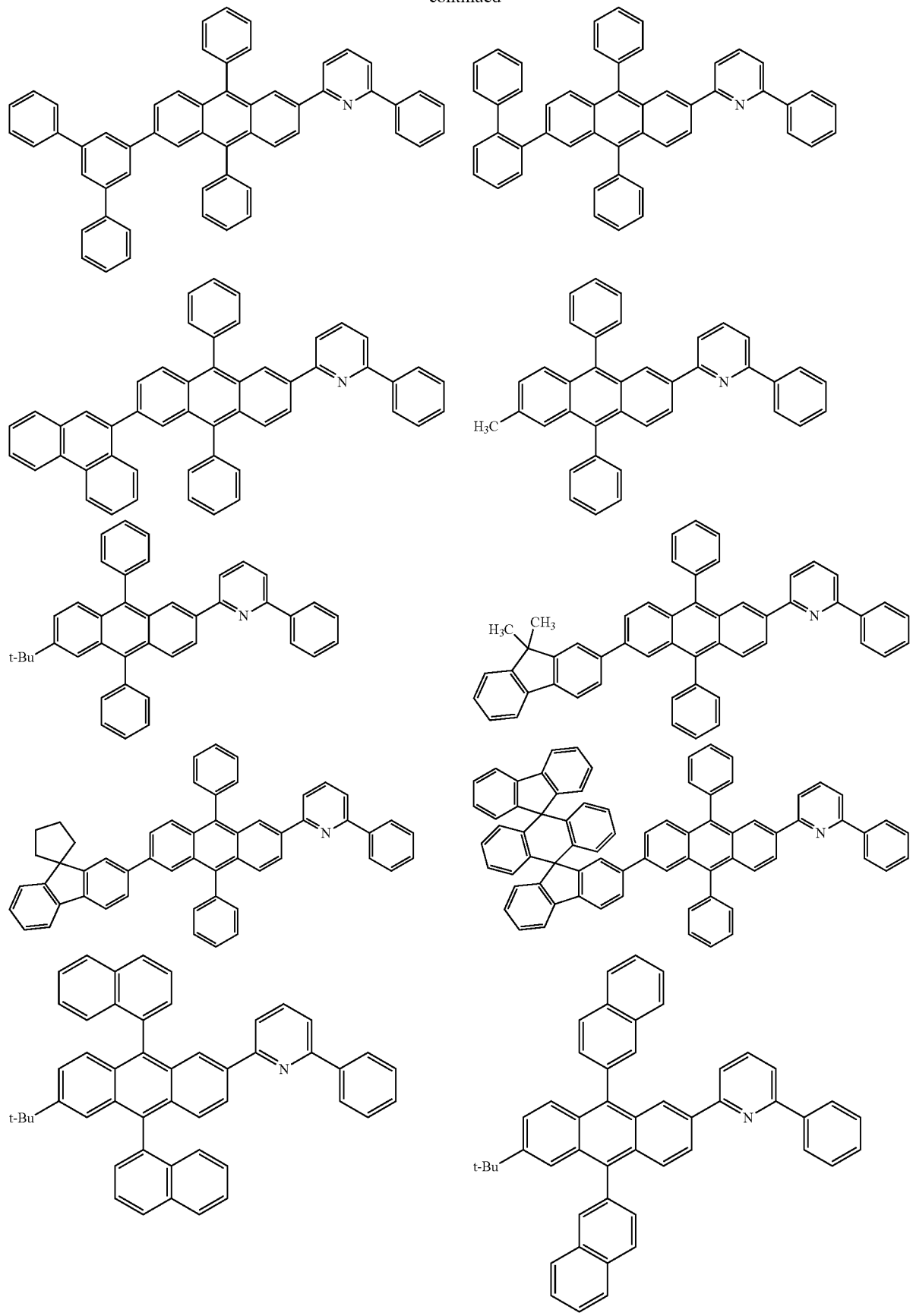

-continued
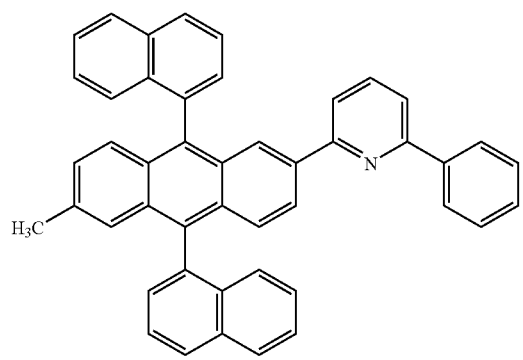
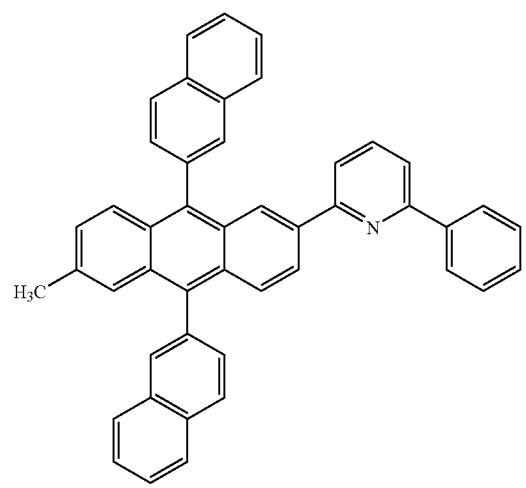
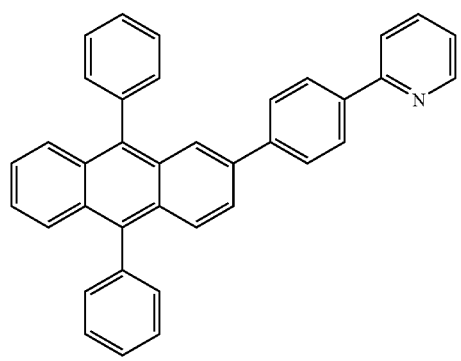
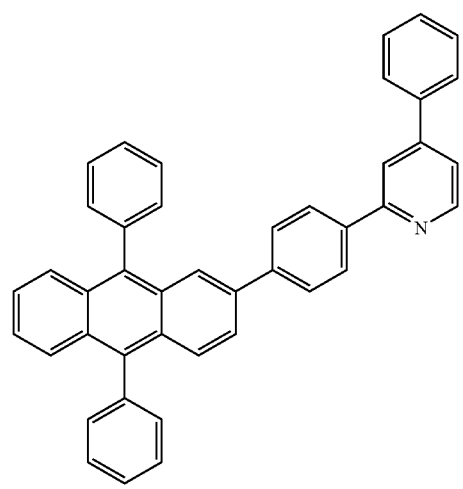
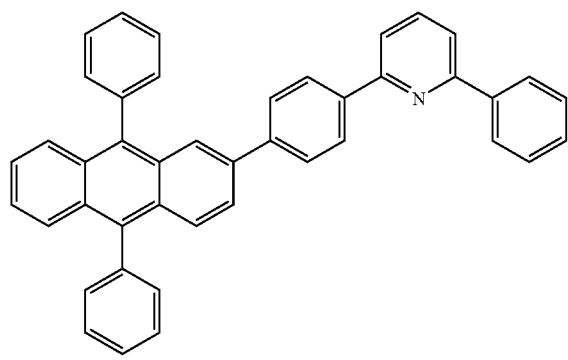
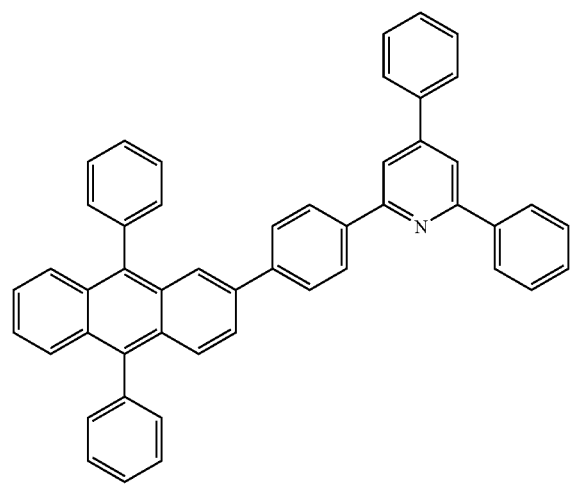

-continued
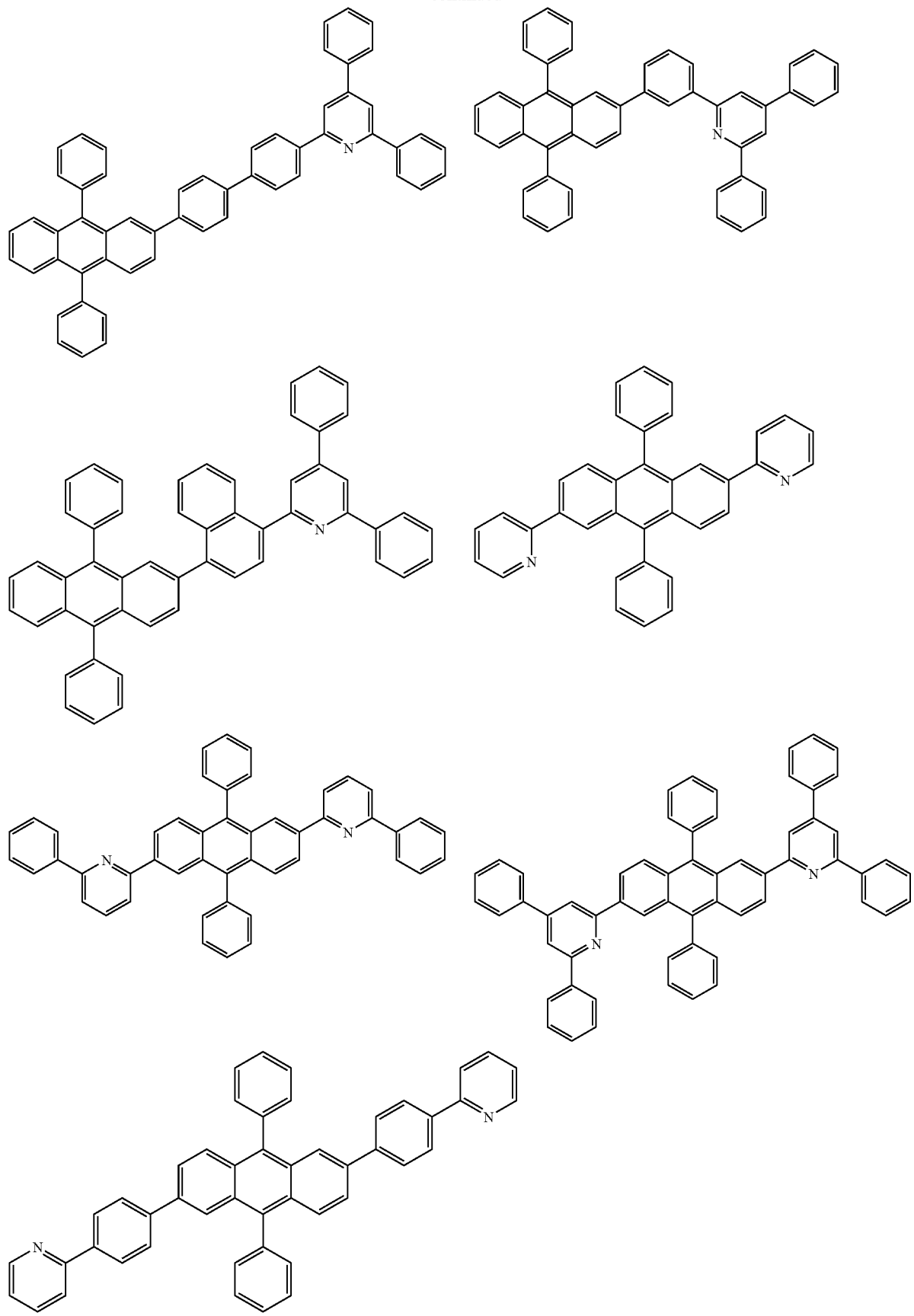

-continued
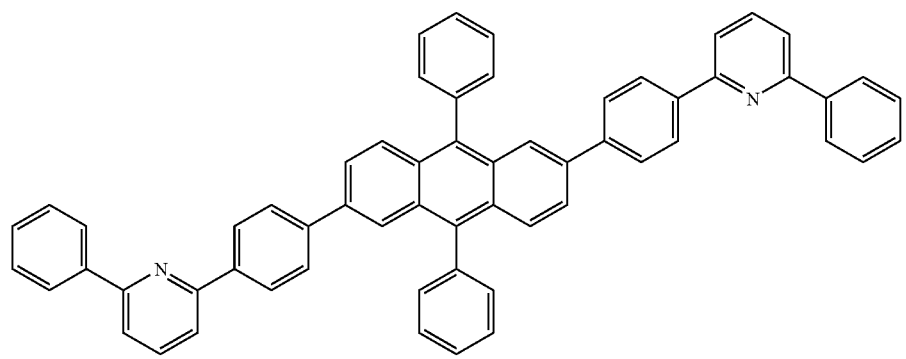
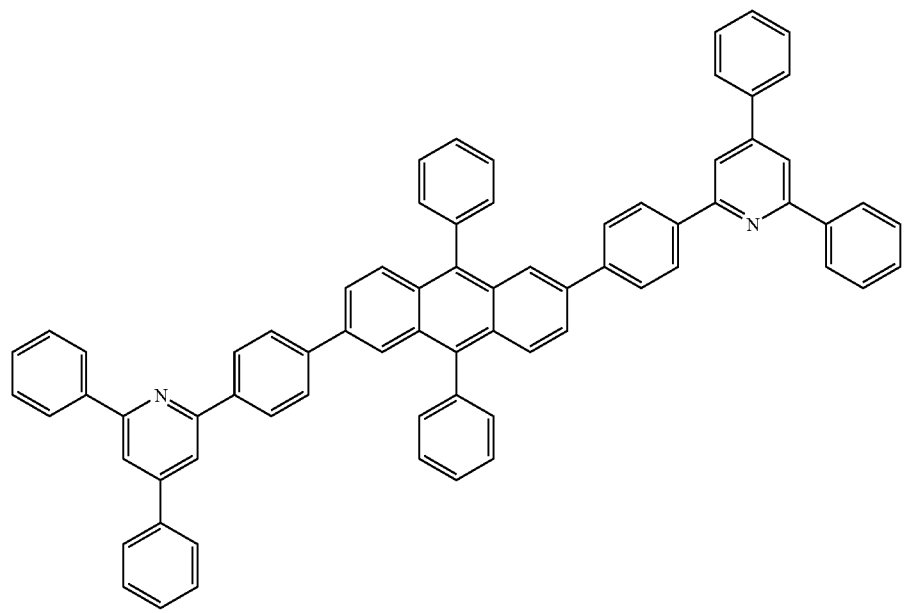
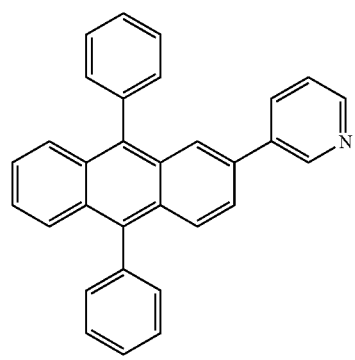
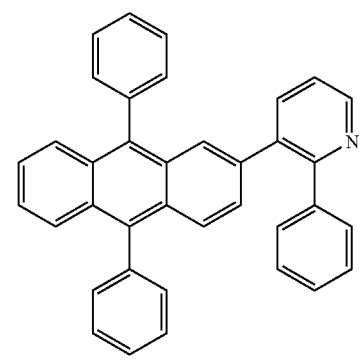
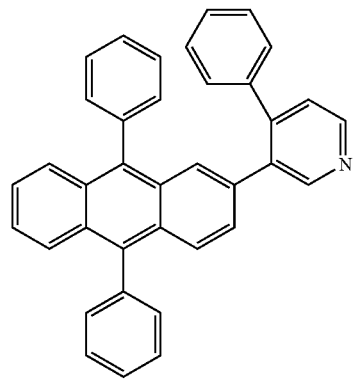
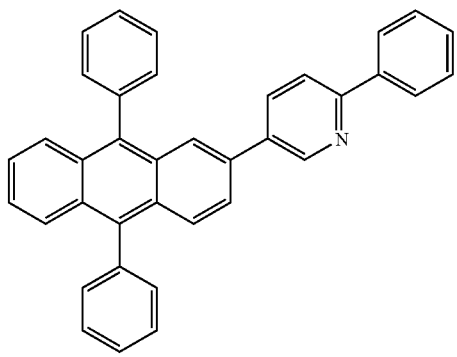

31
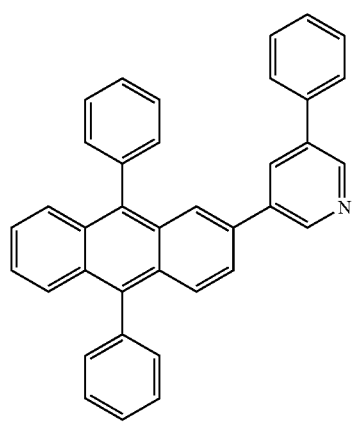
32
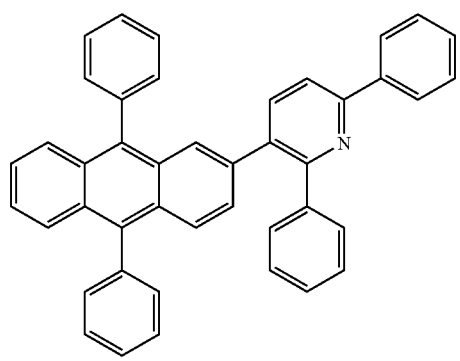
-continued
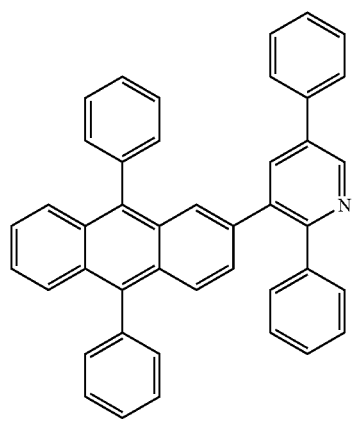
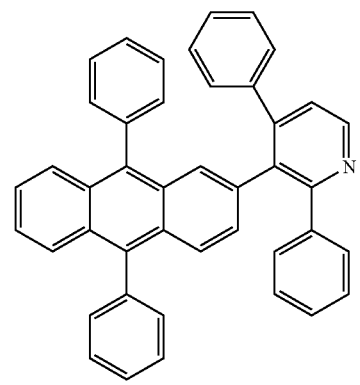
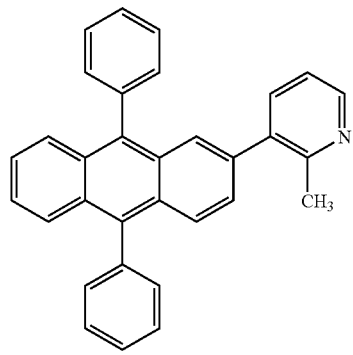
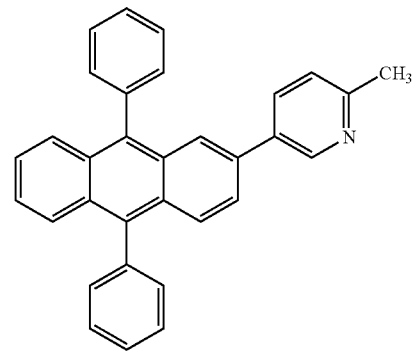
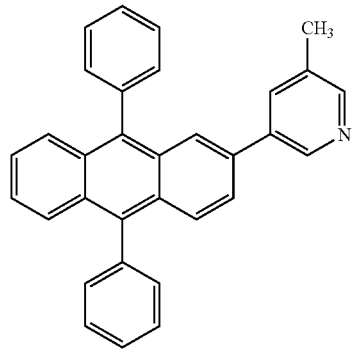
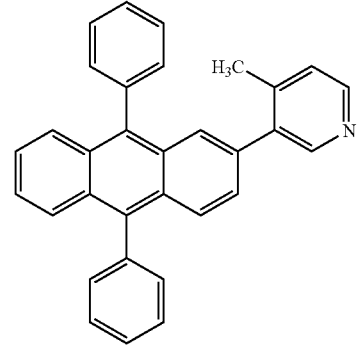

-continued
33
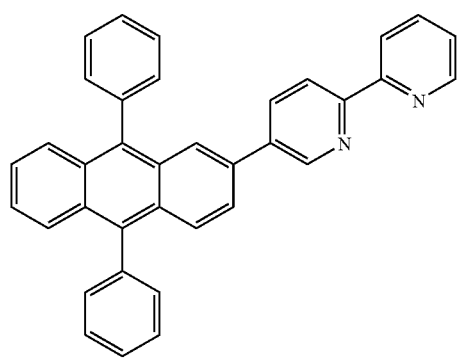
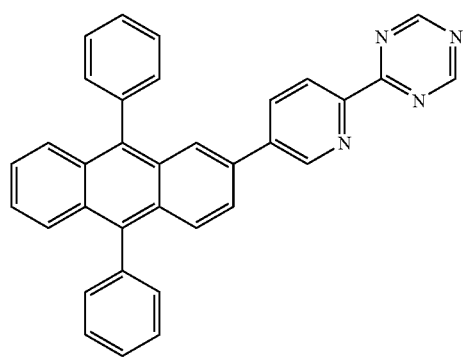
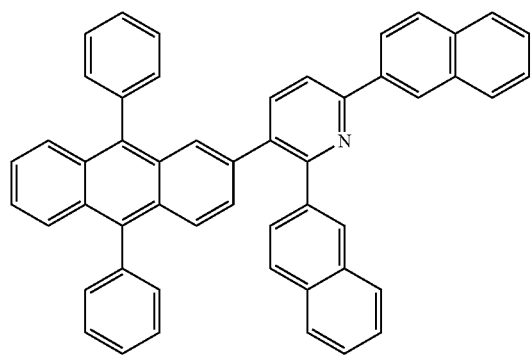
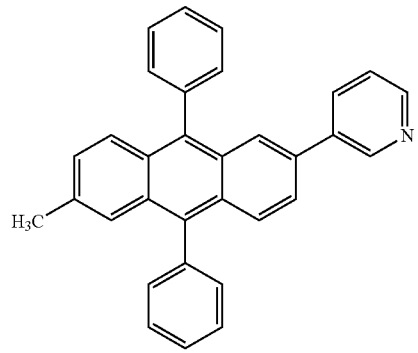
34
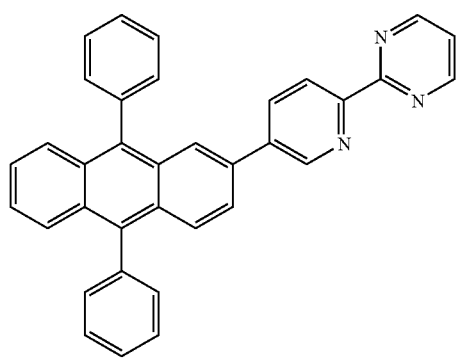
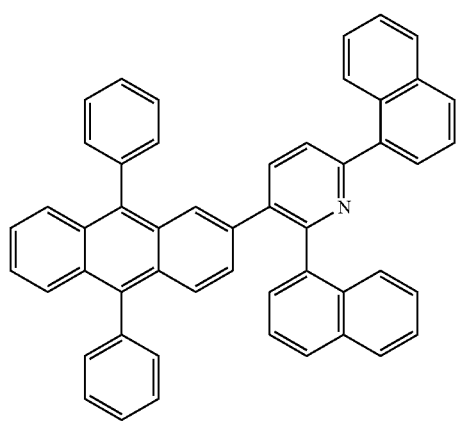
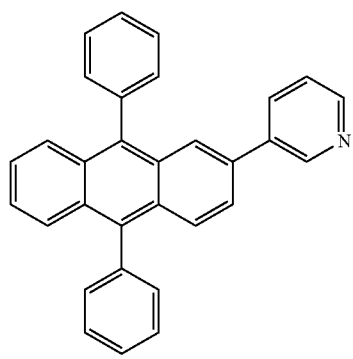
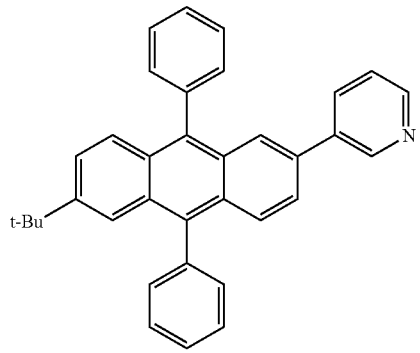

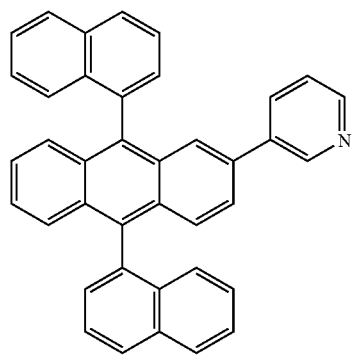
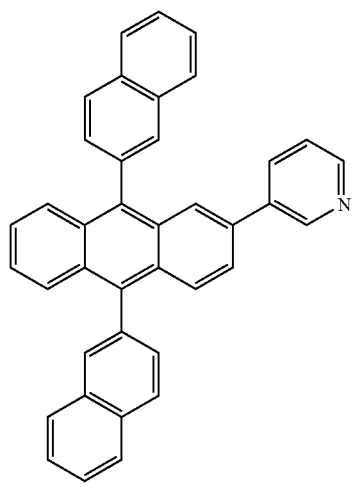
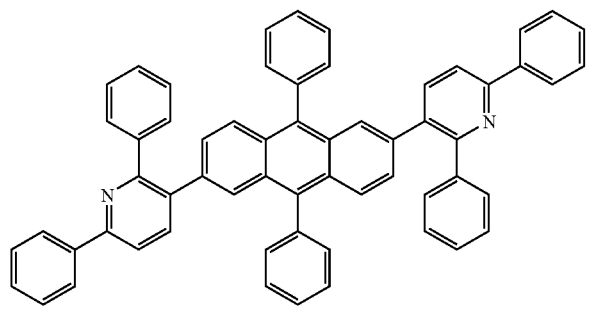
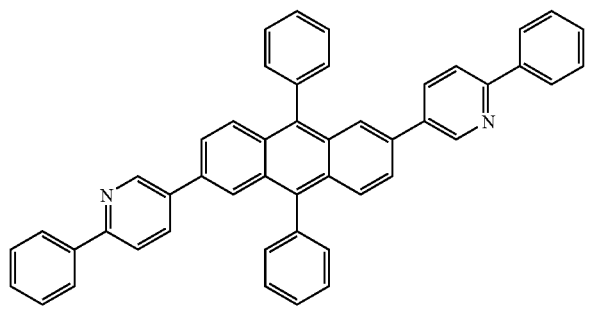
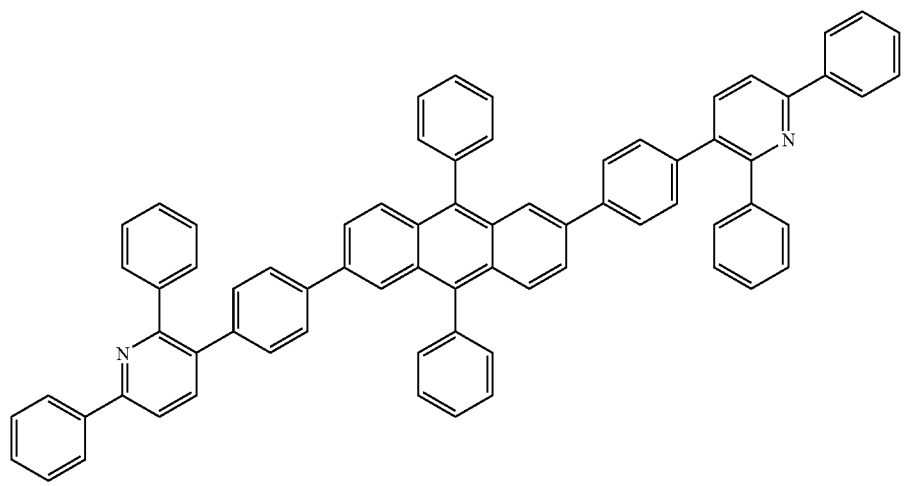

-continued
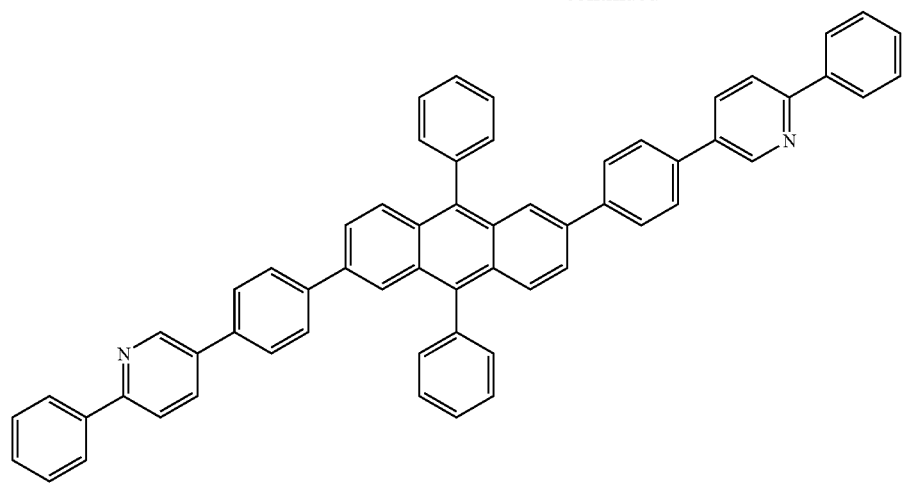
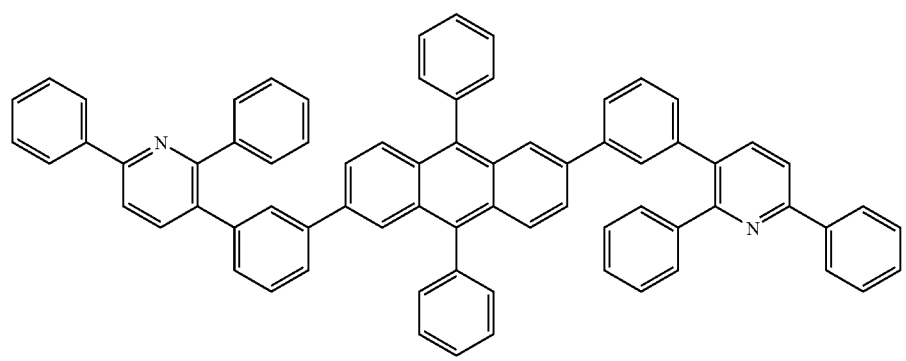
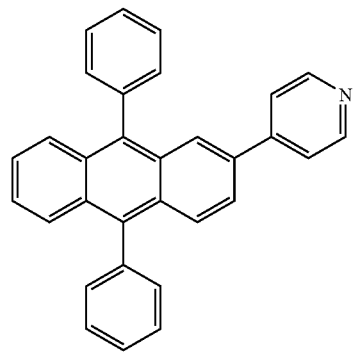
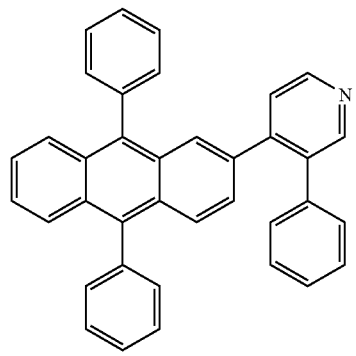
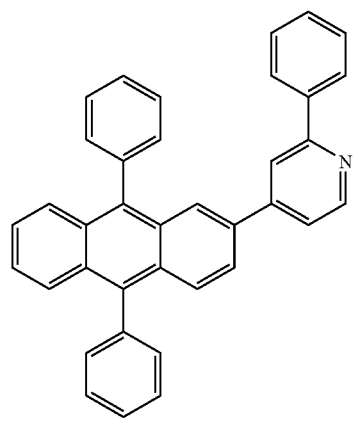

39
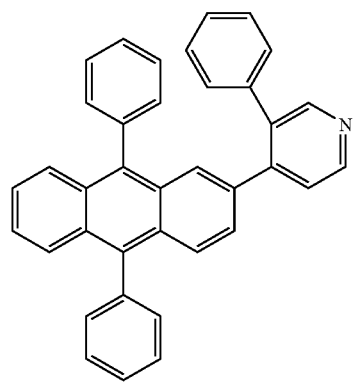
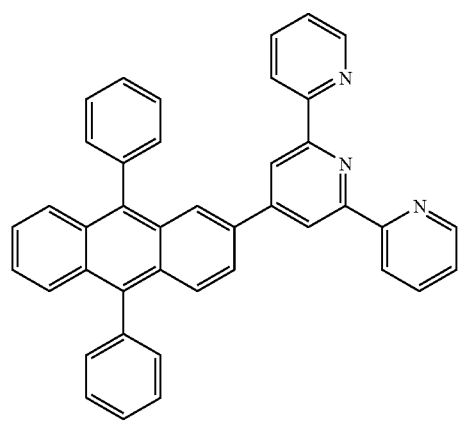
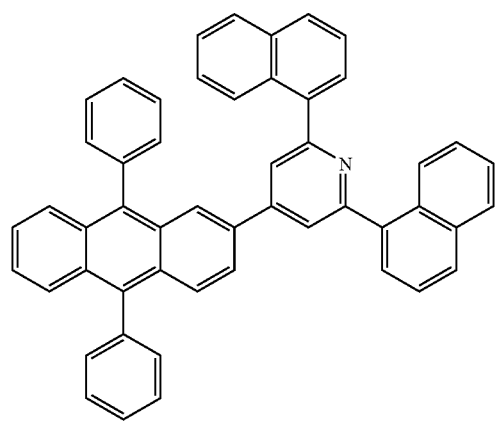
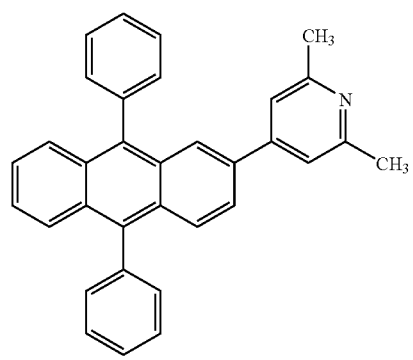
40
-continued
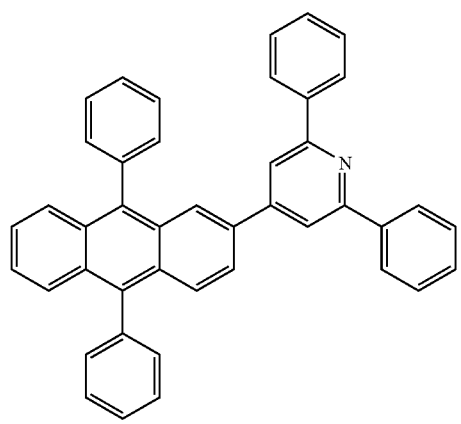
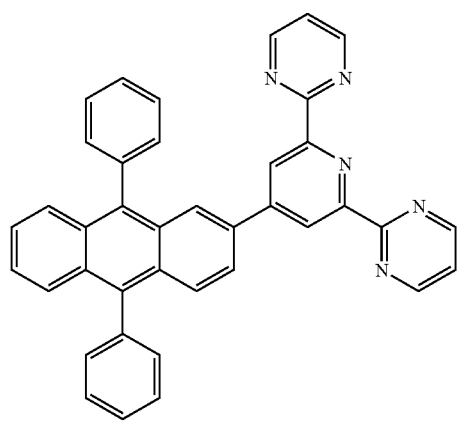
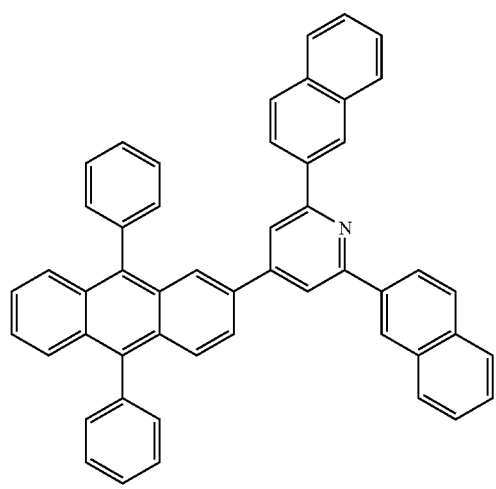
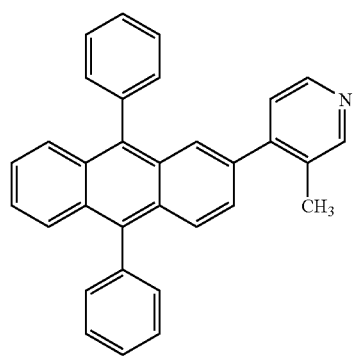

-continued
41
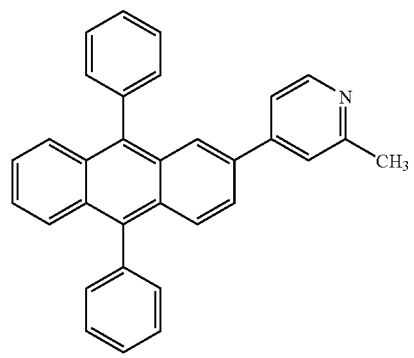
42
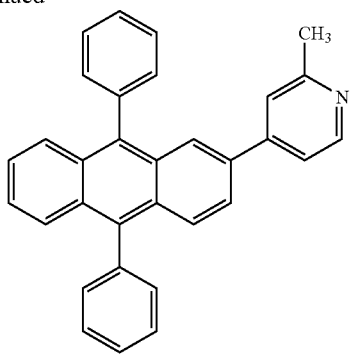
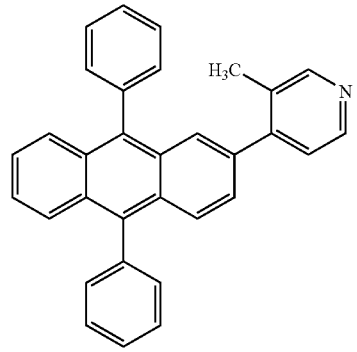
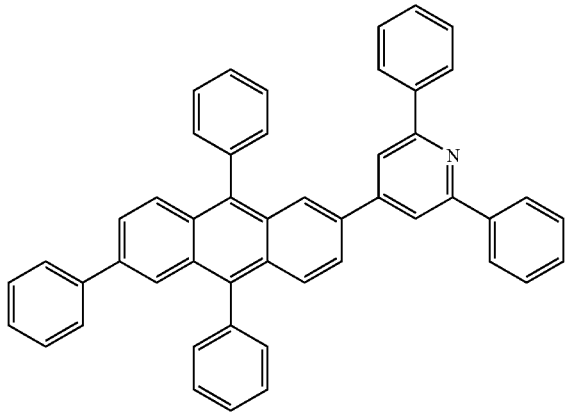
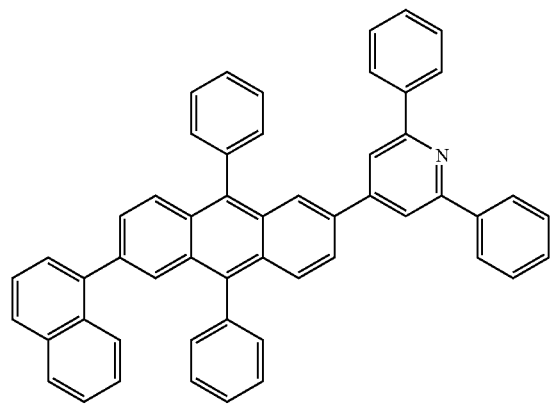
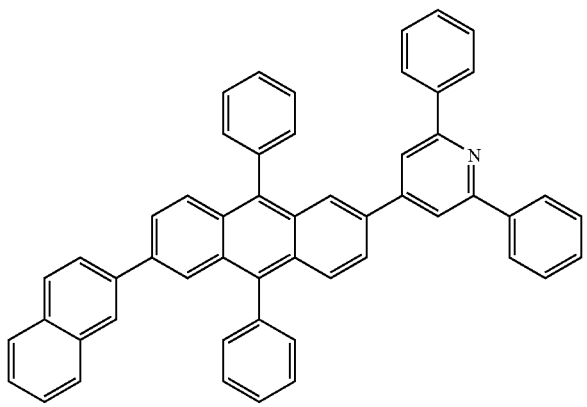
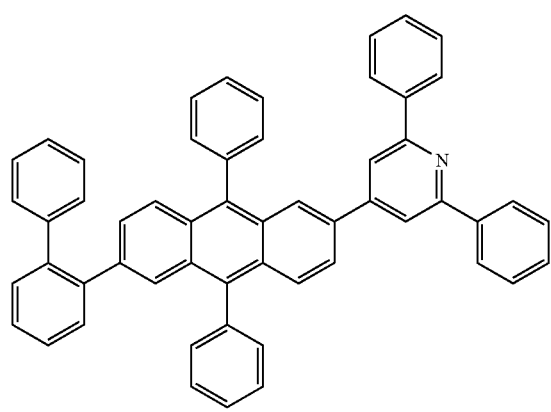
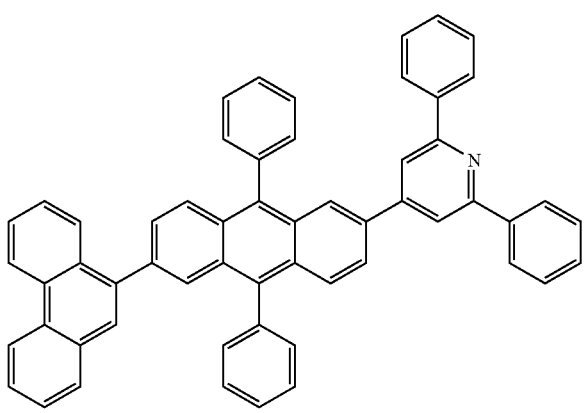

-continued
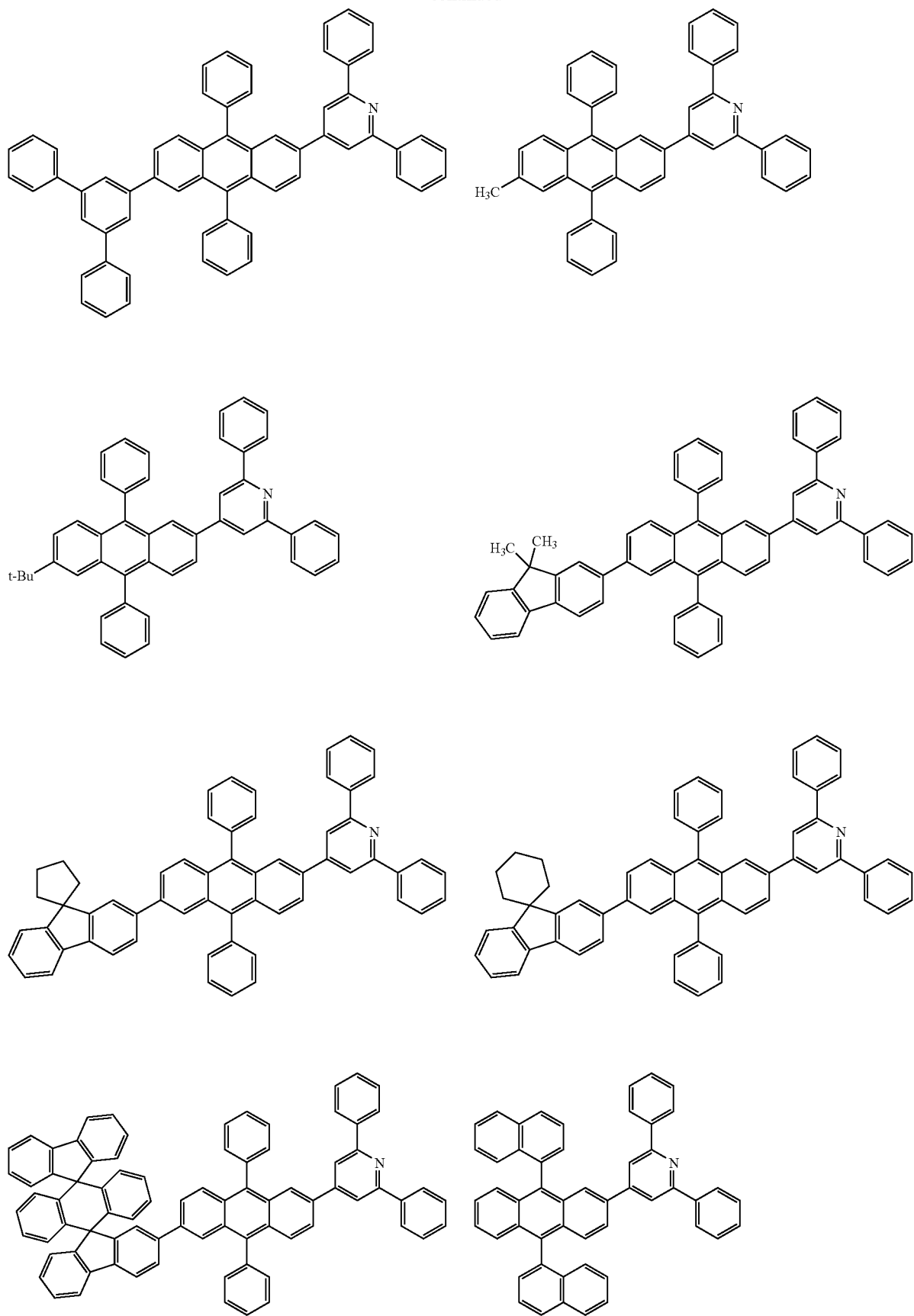

-continued
45
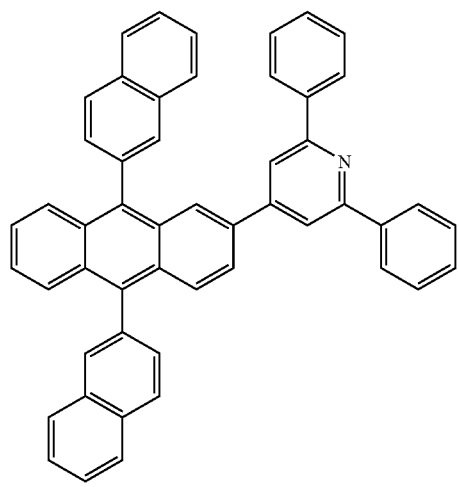
46
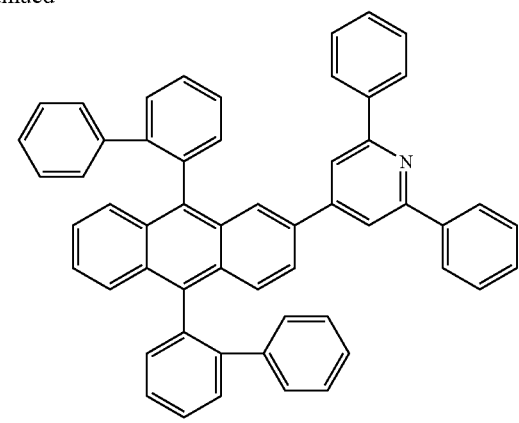
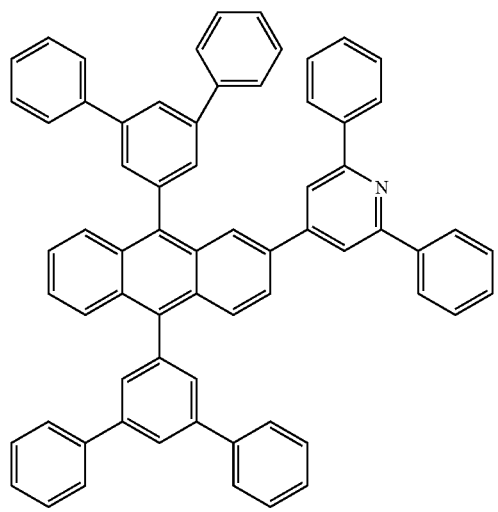
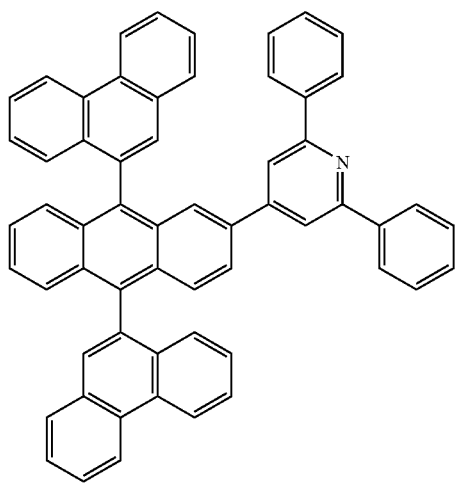
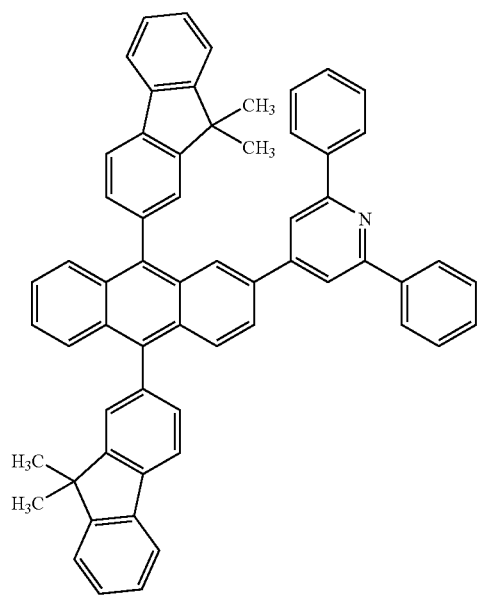
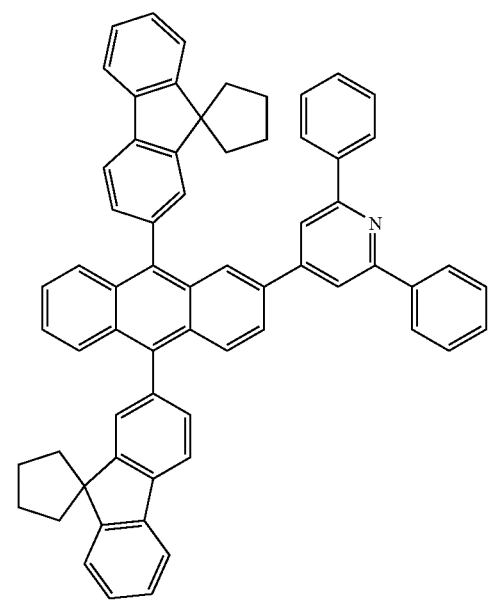

47
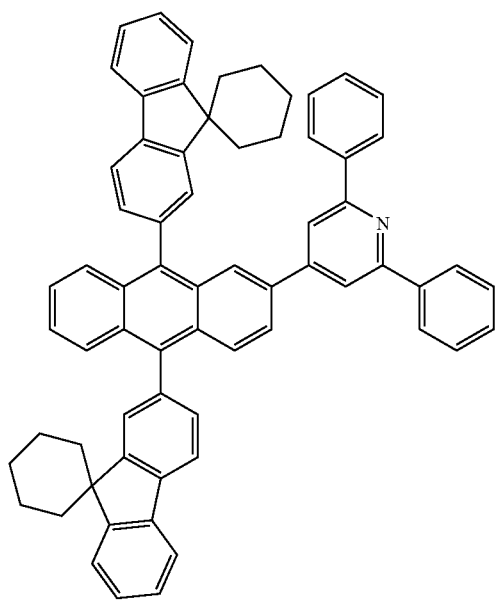
48
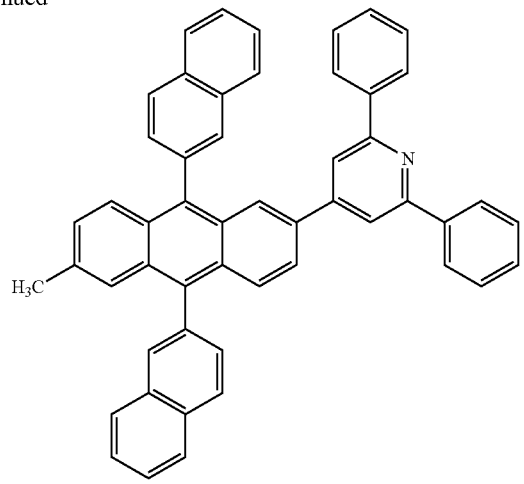
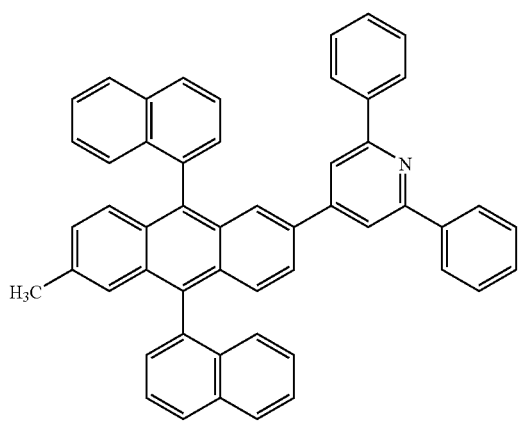
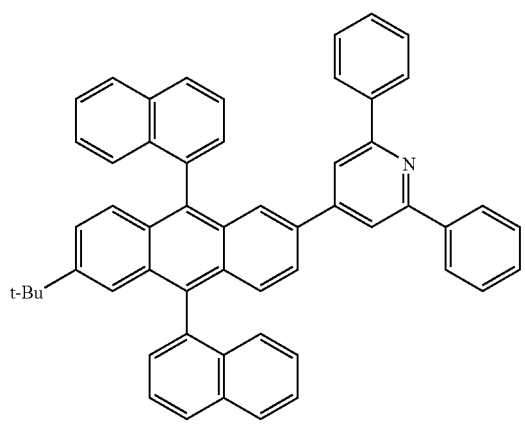
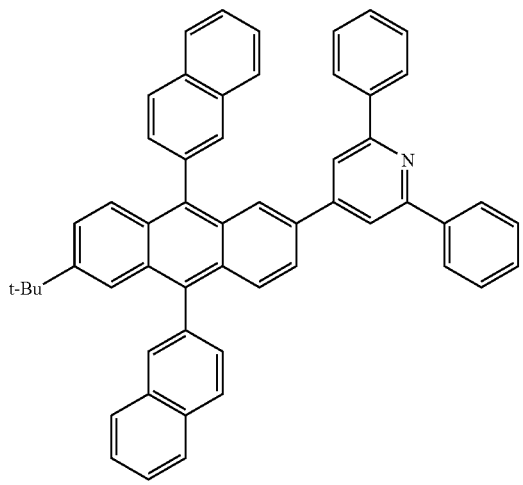
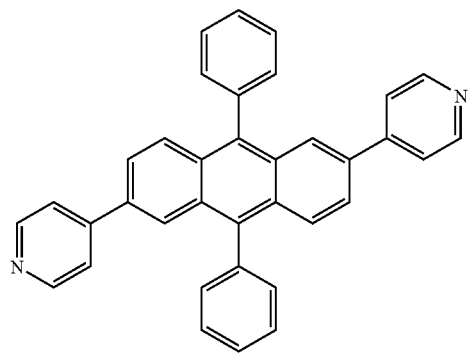

-continued
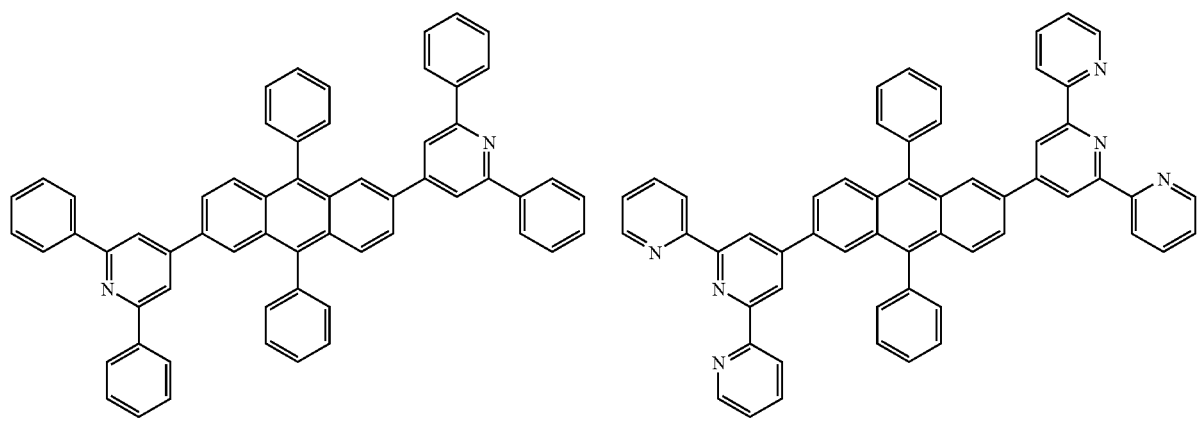
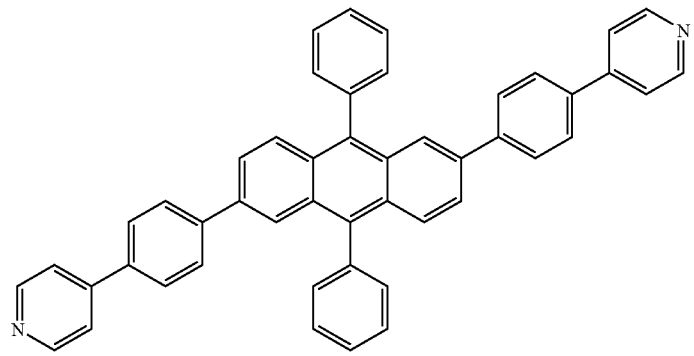
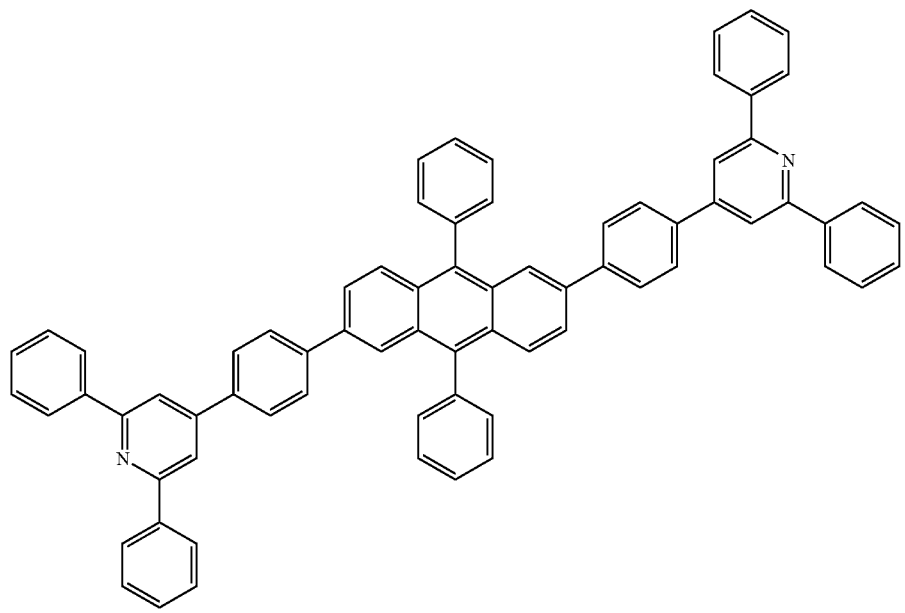

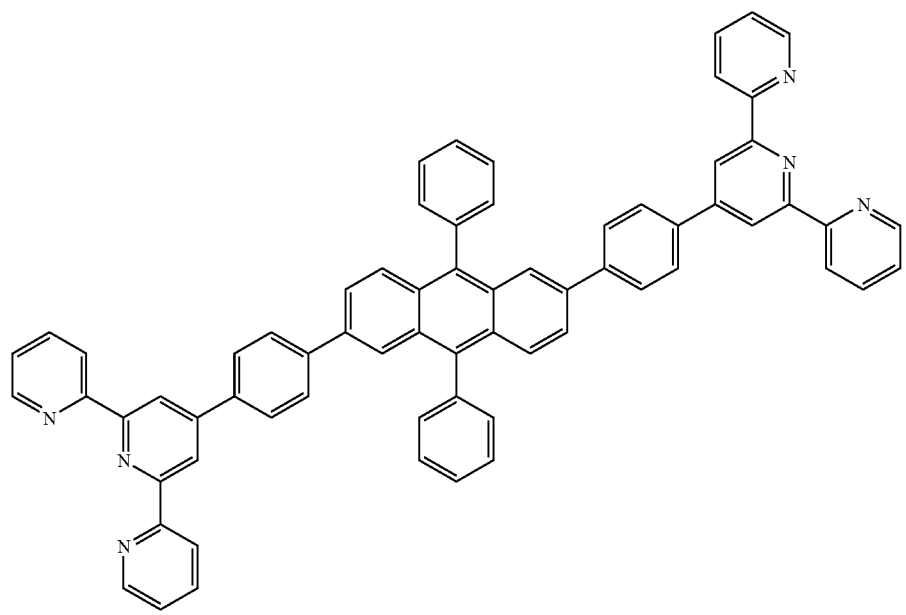
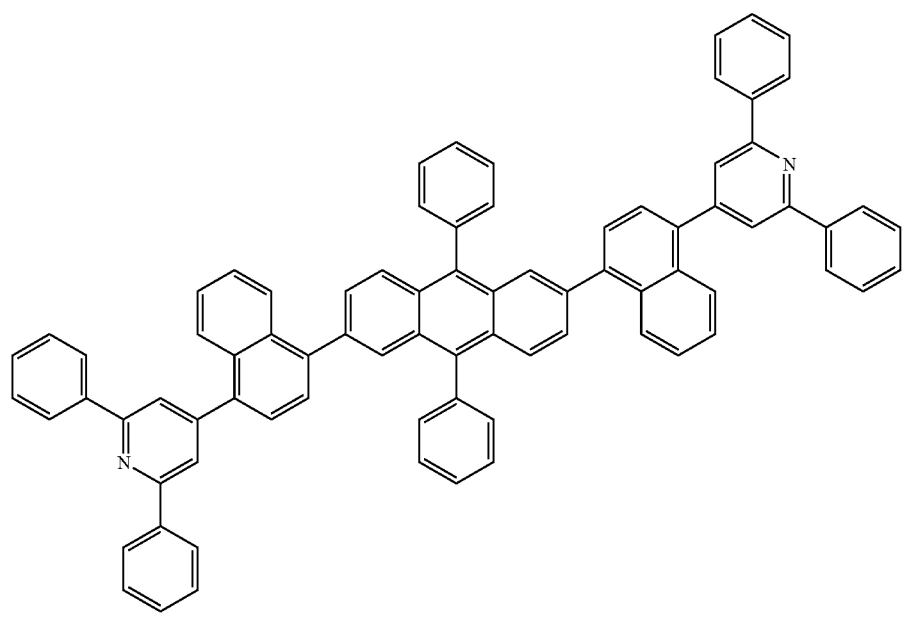

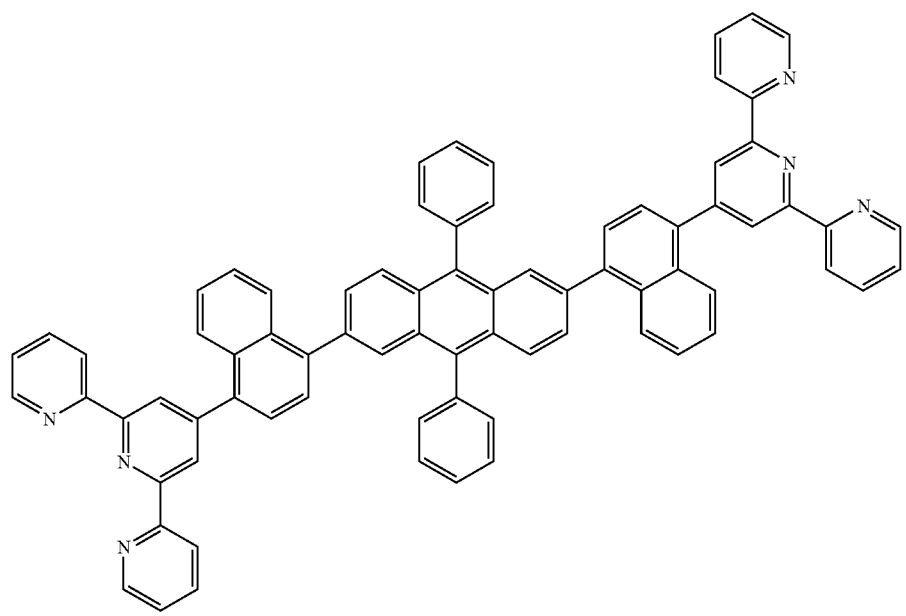
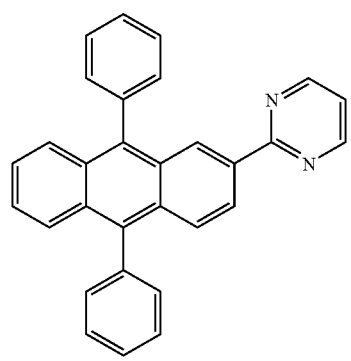
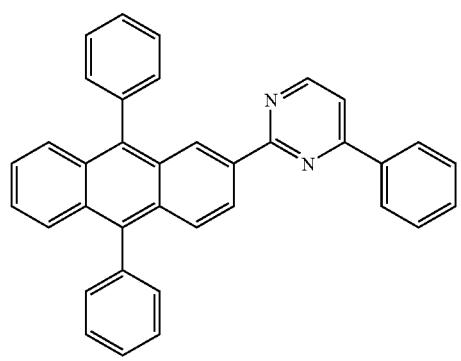
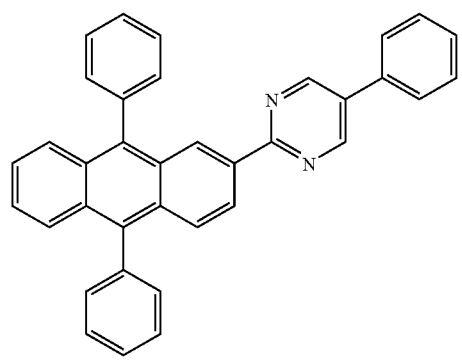
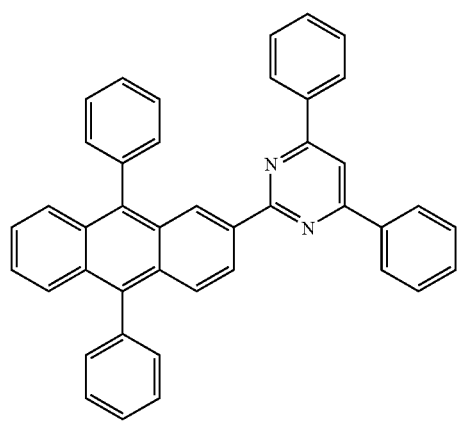

55
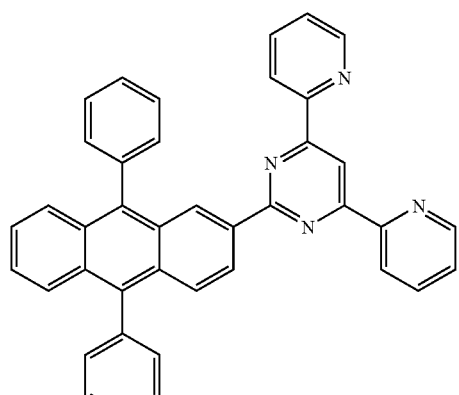
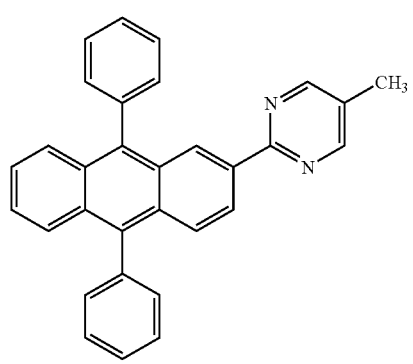
56
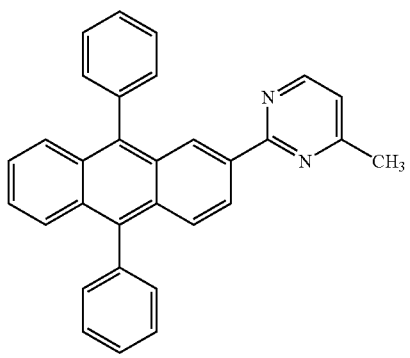
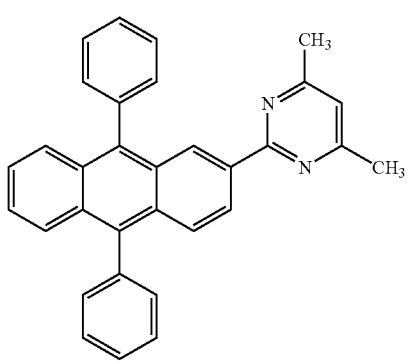
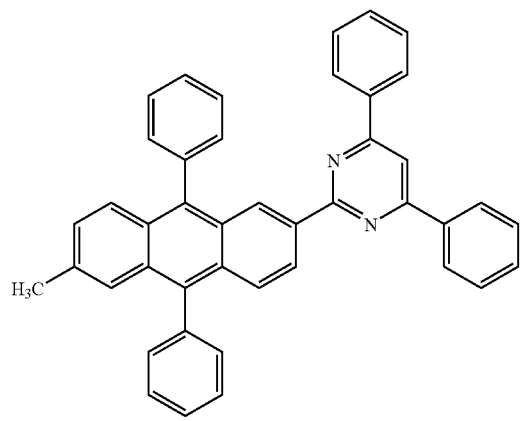
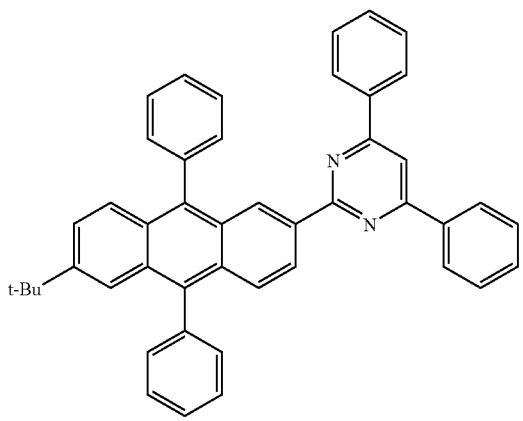
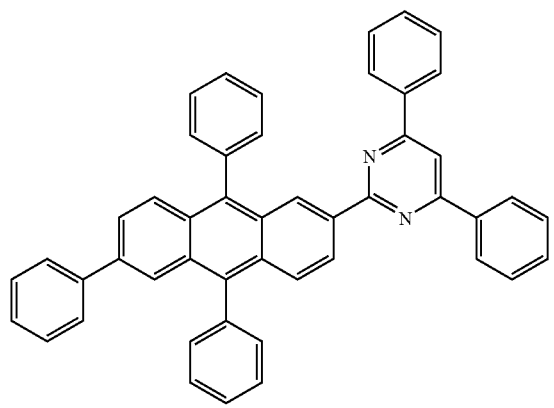
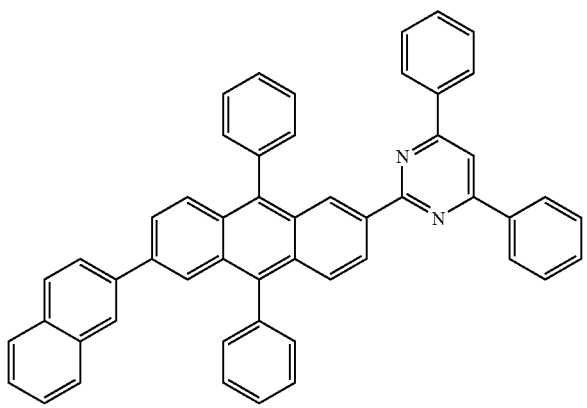

-continued
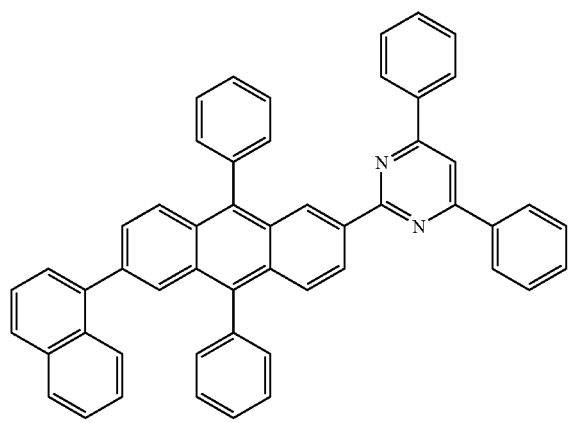
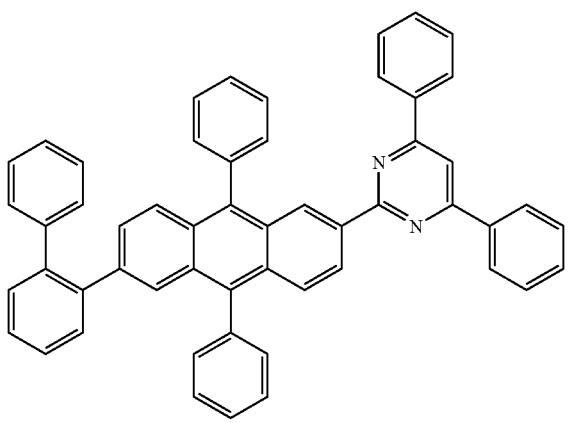
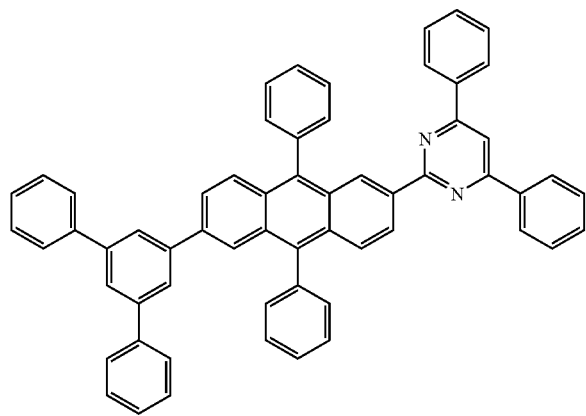
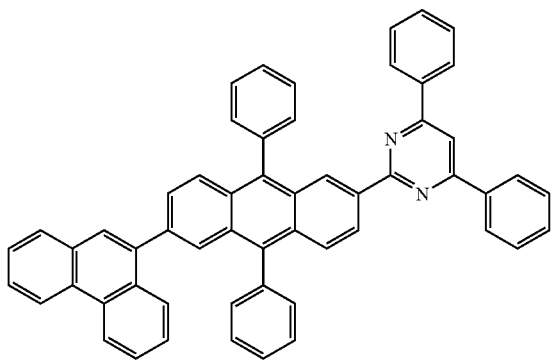
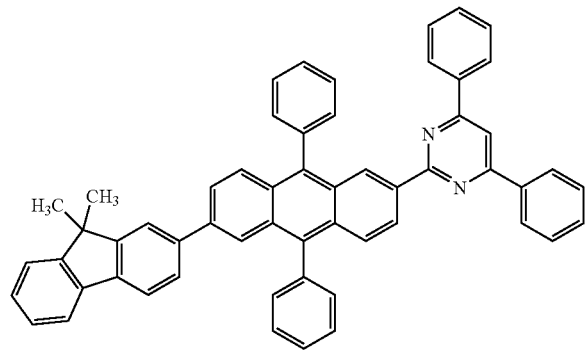
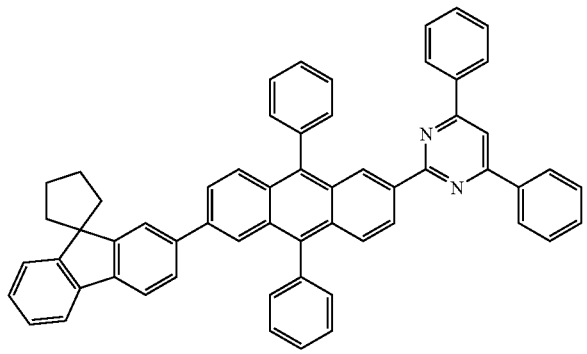
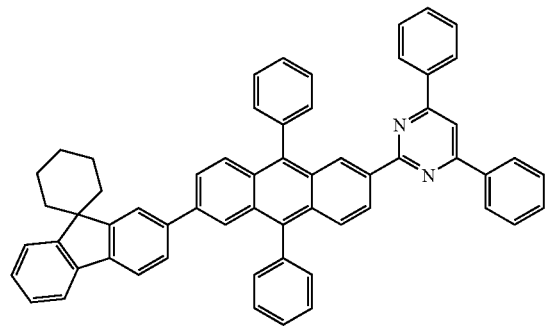
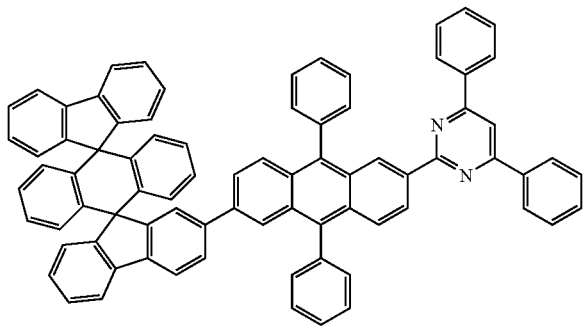

59
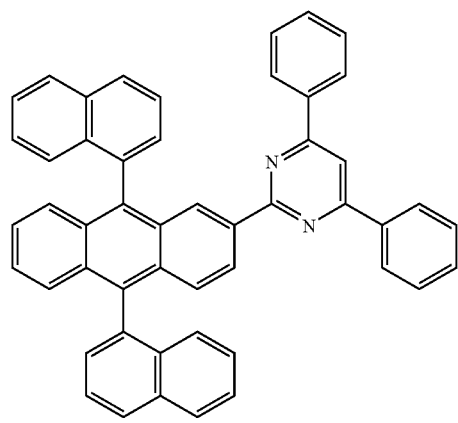
60
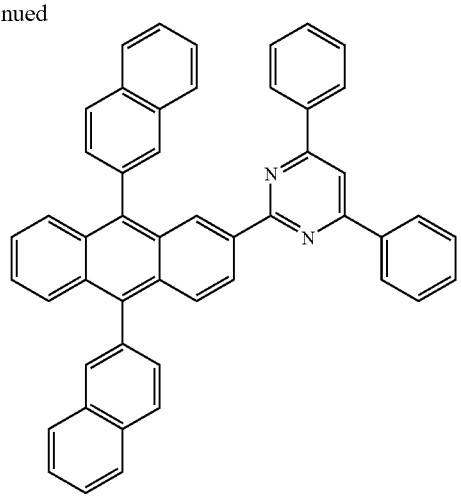
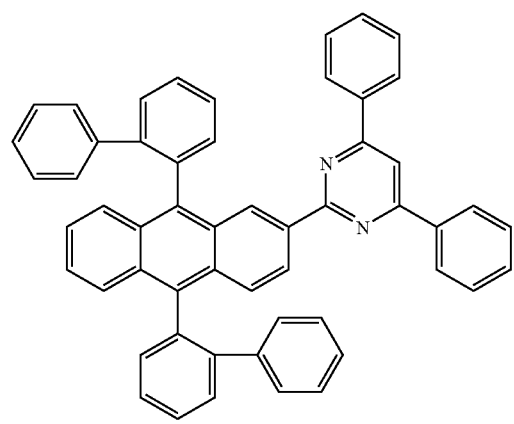
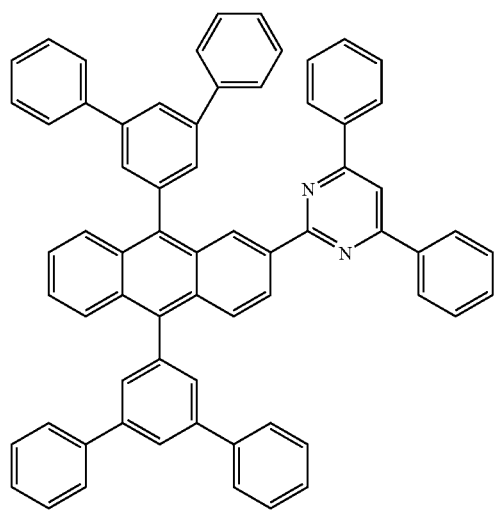
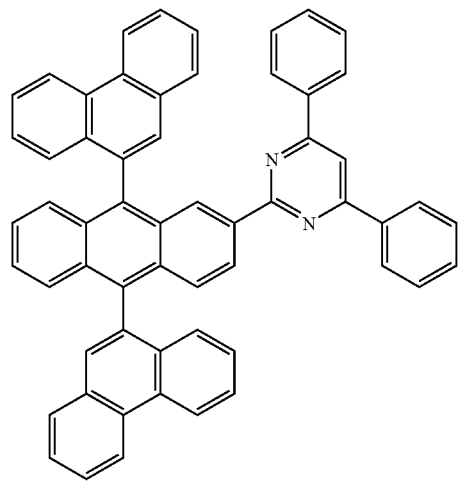
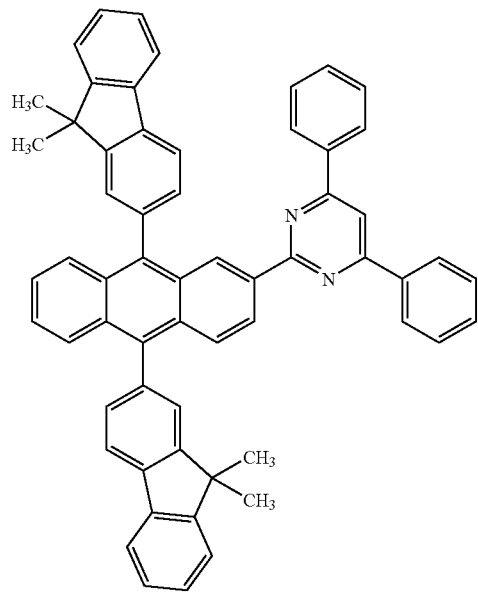

-continued
61
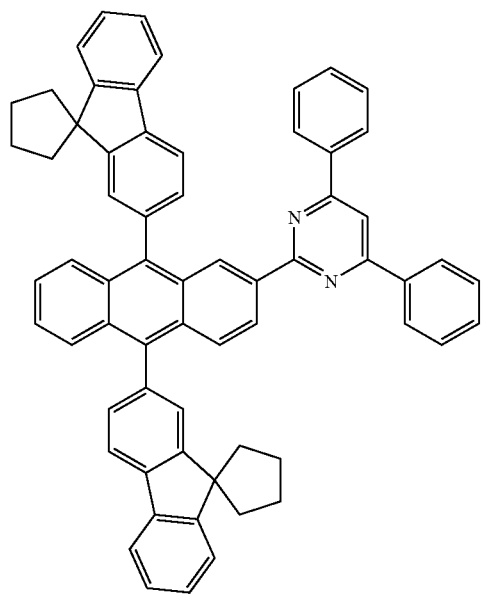
62
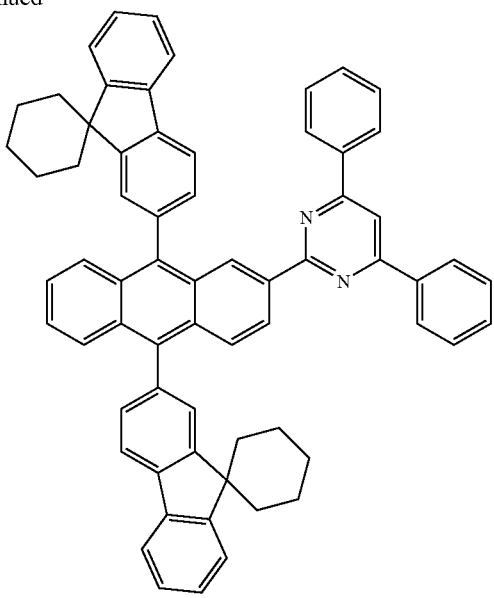
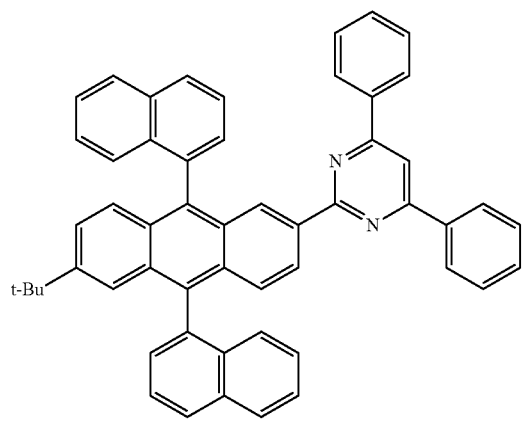
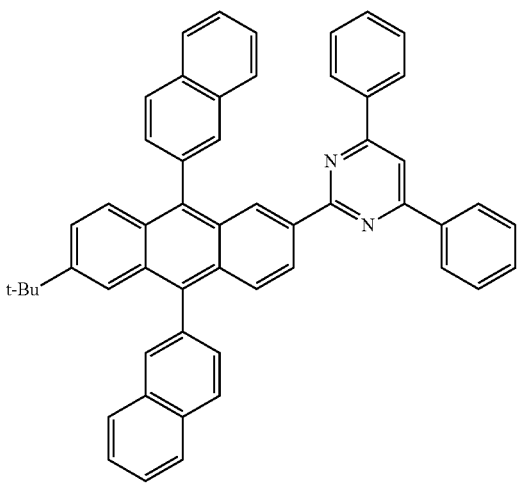
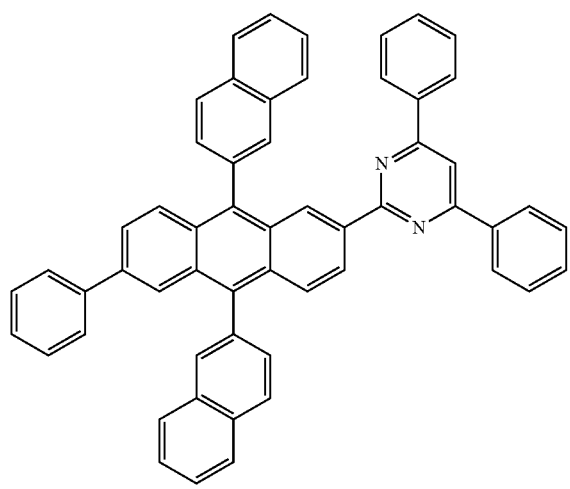
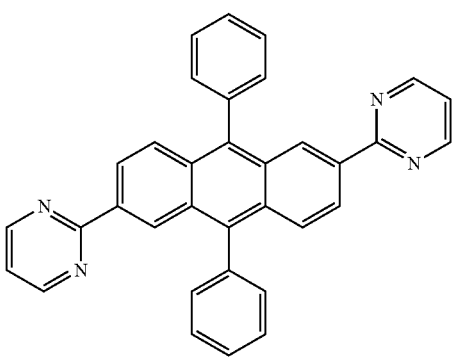

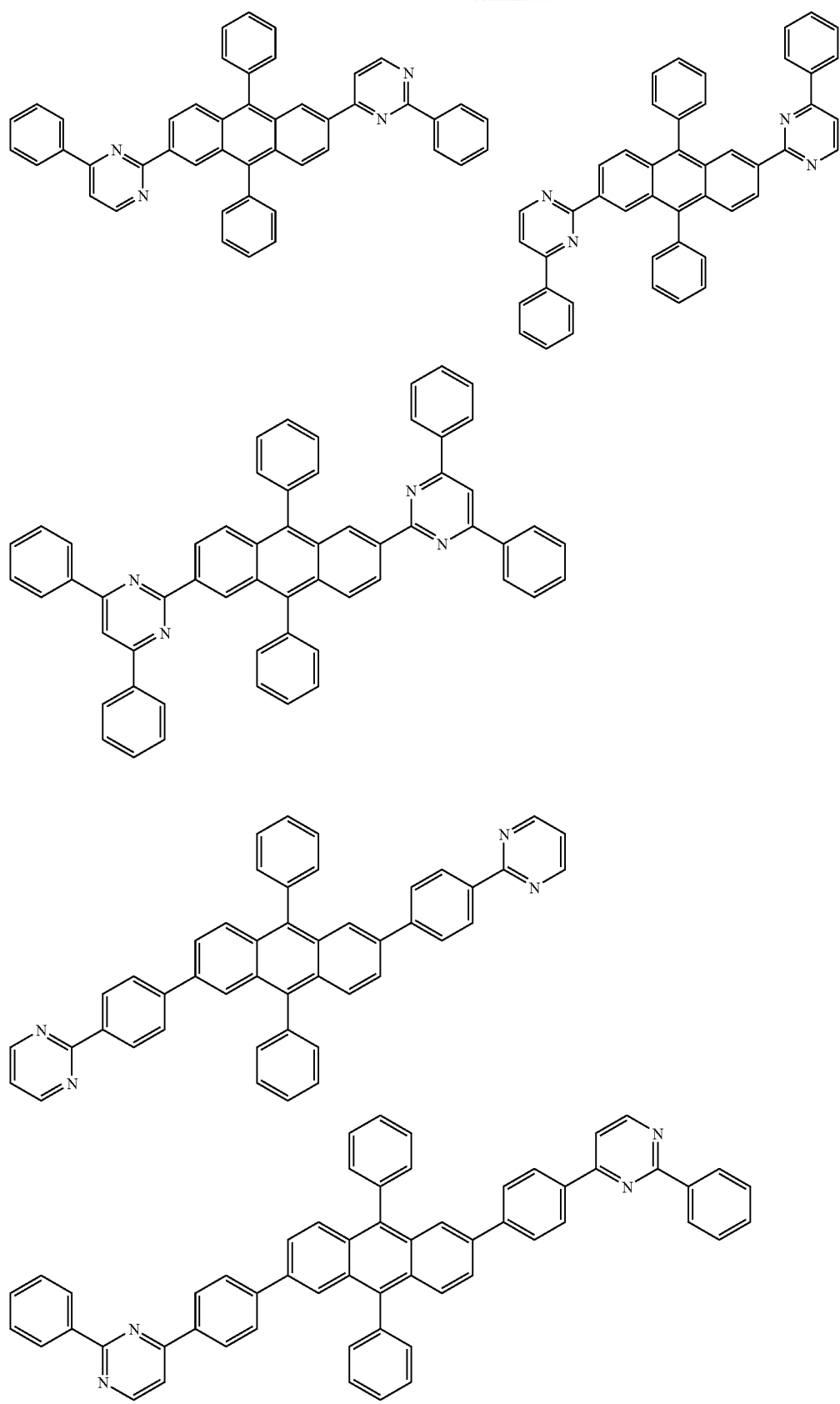

-continued
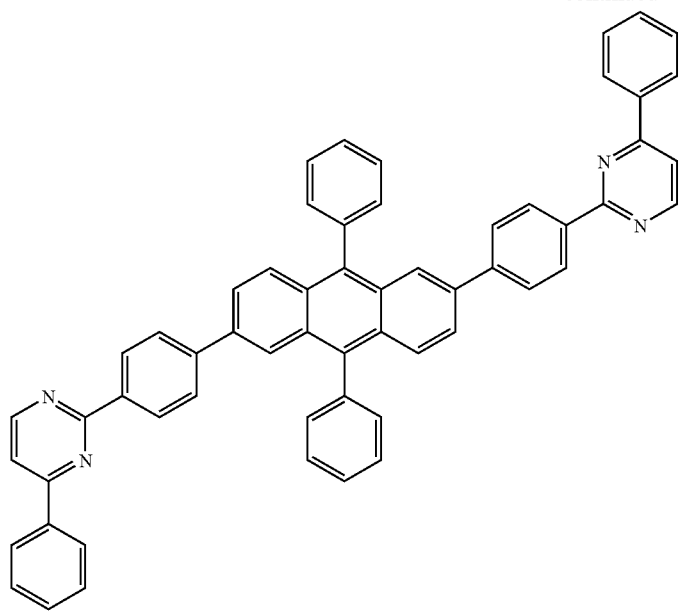
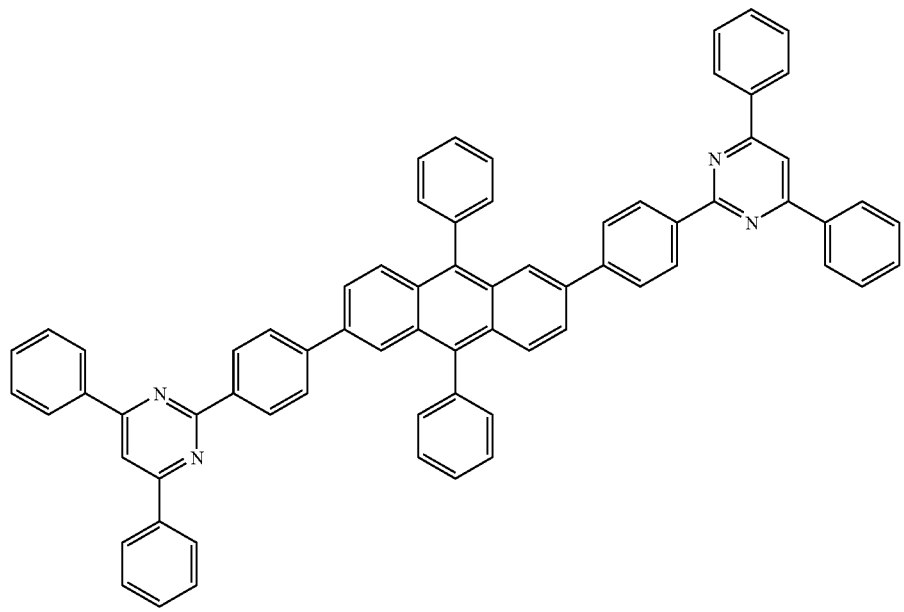
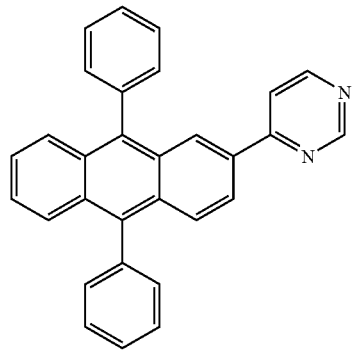
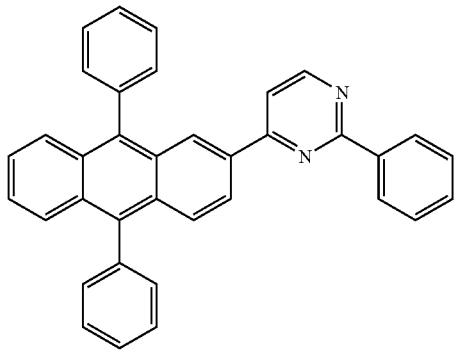

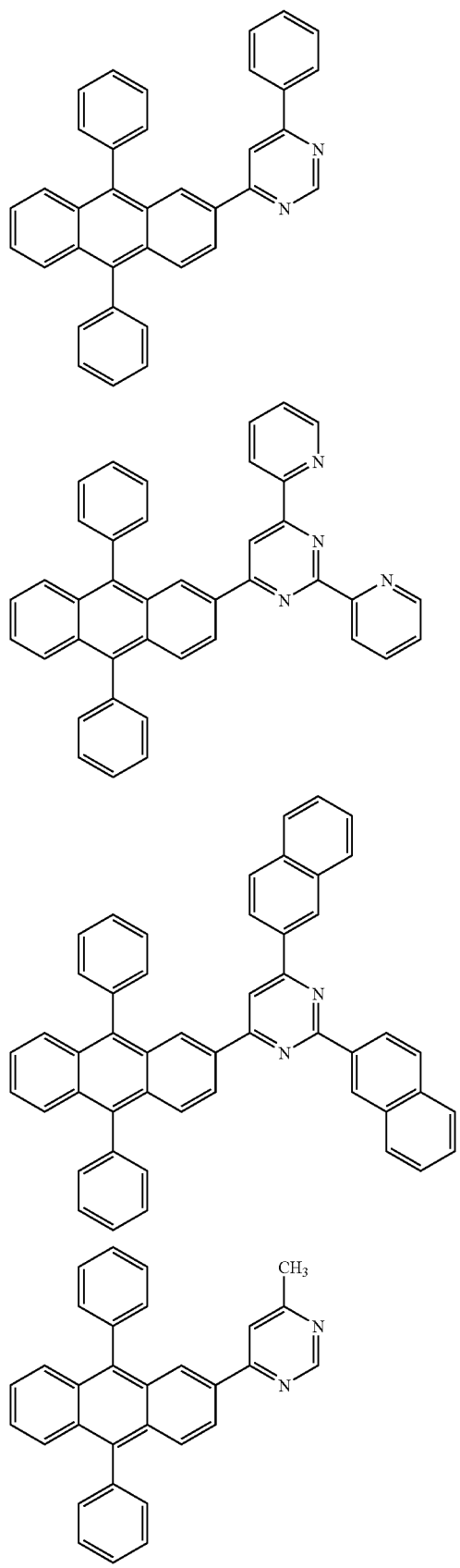

-continued
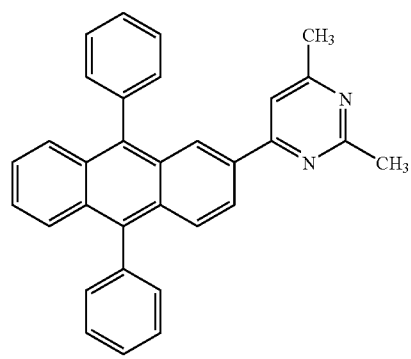
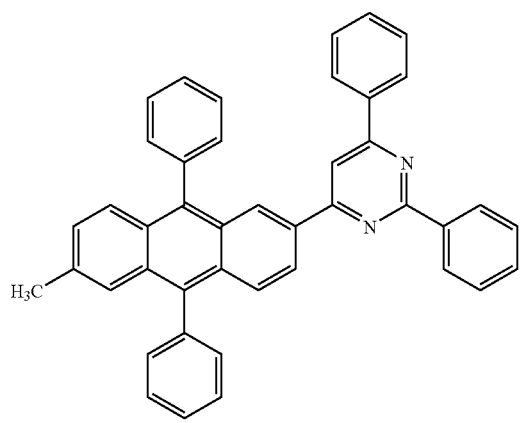
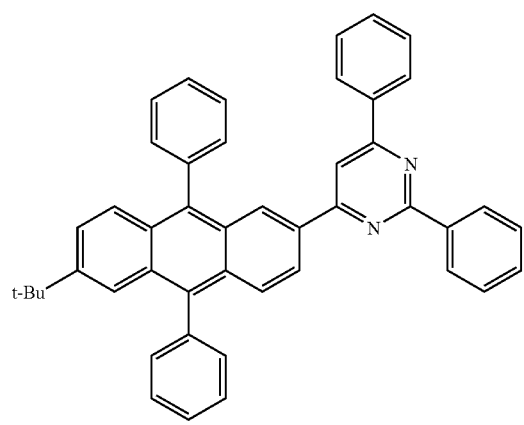
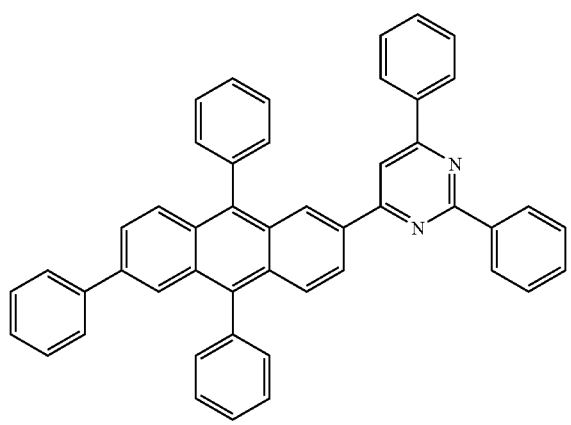
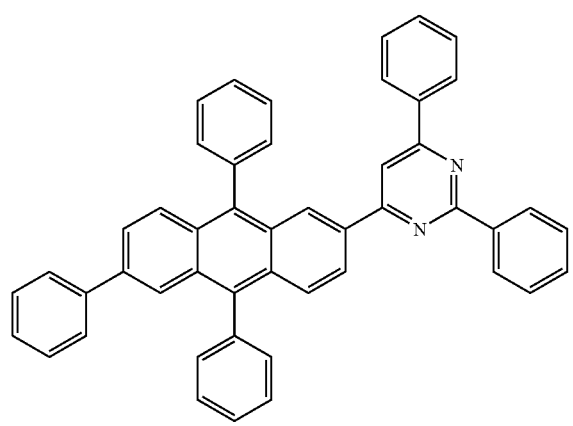
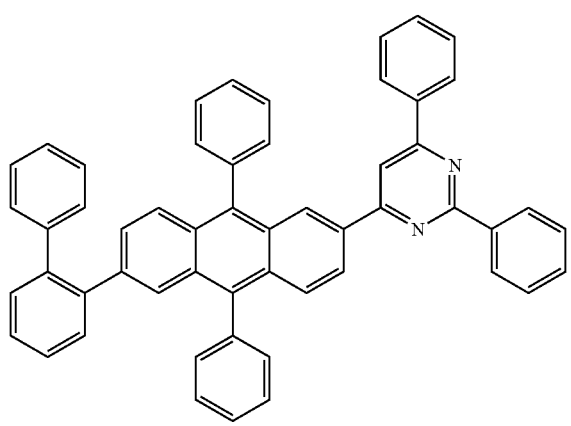
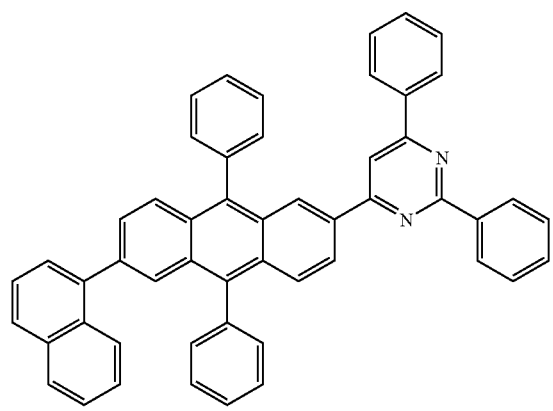
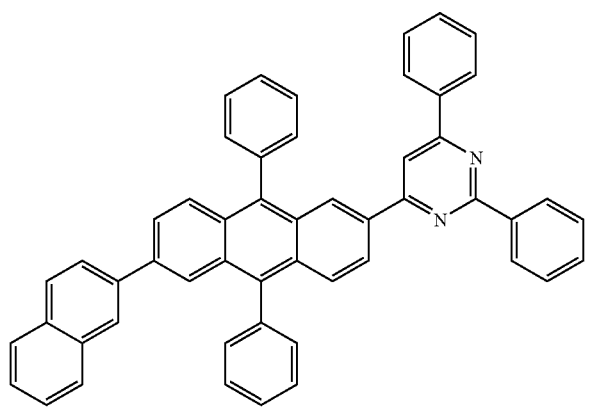

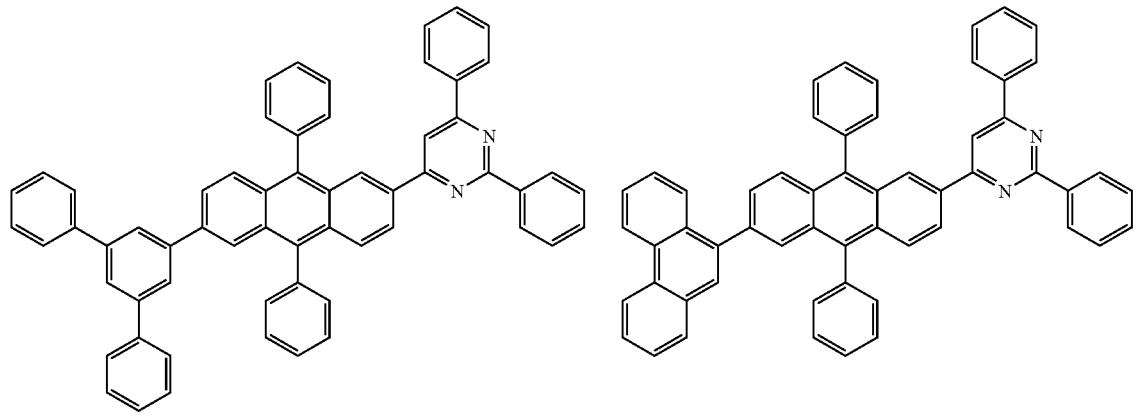
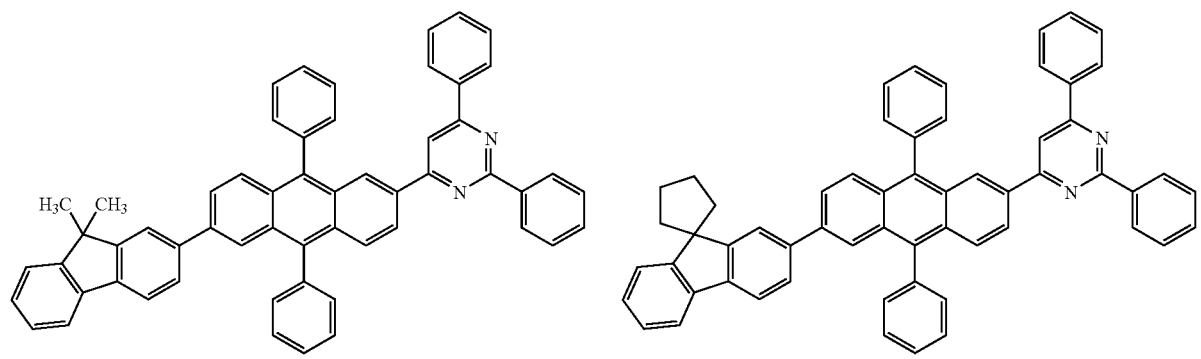
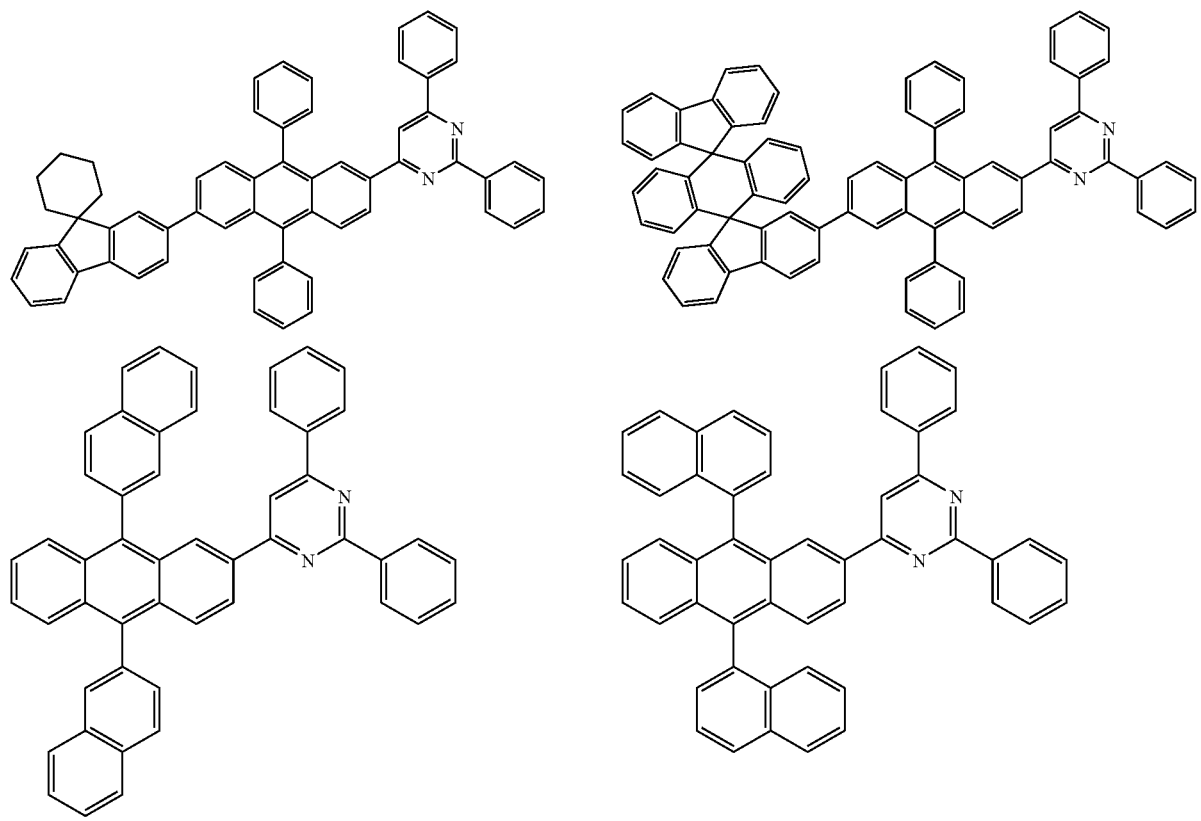

-continued
73
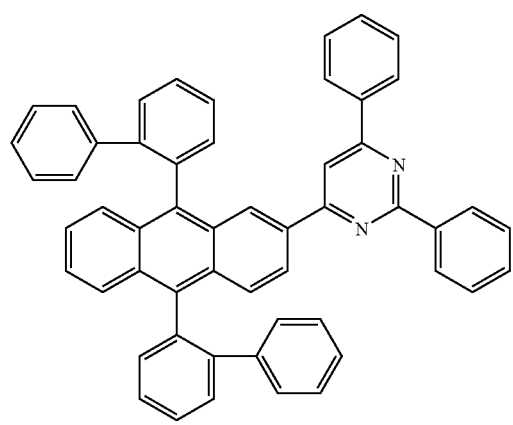
74
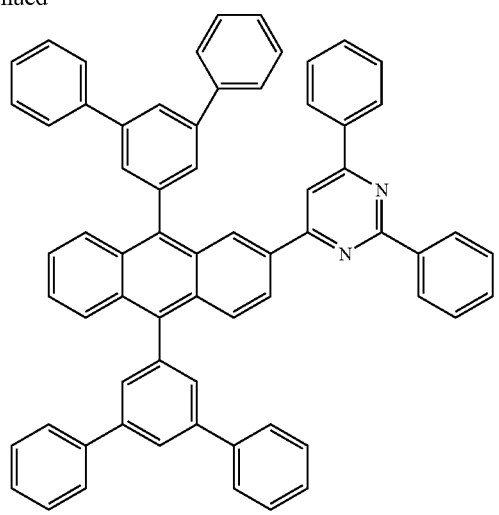
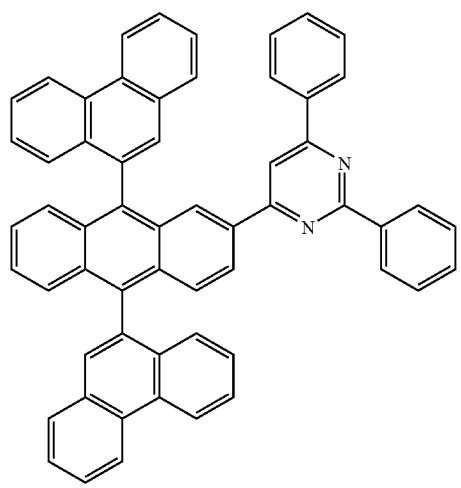
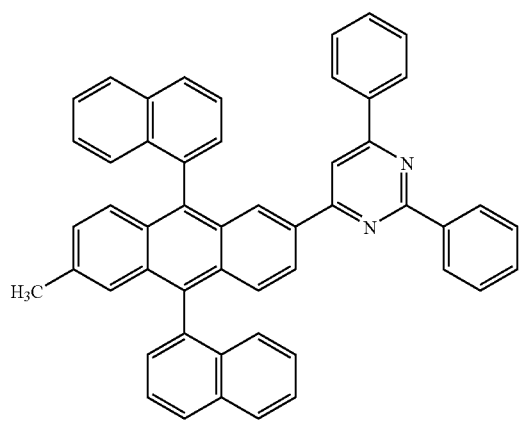
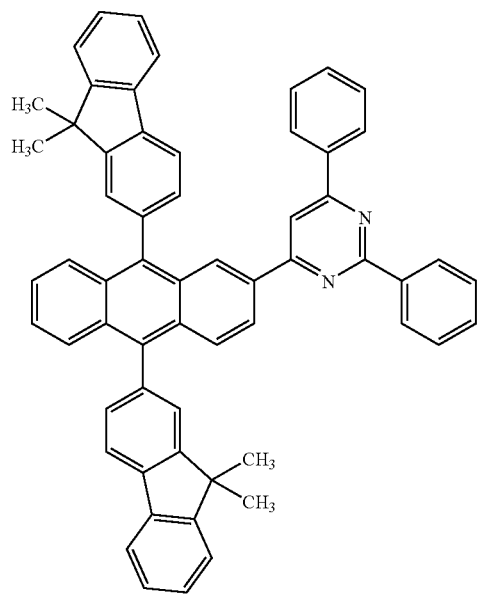
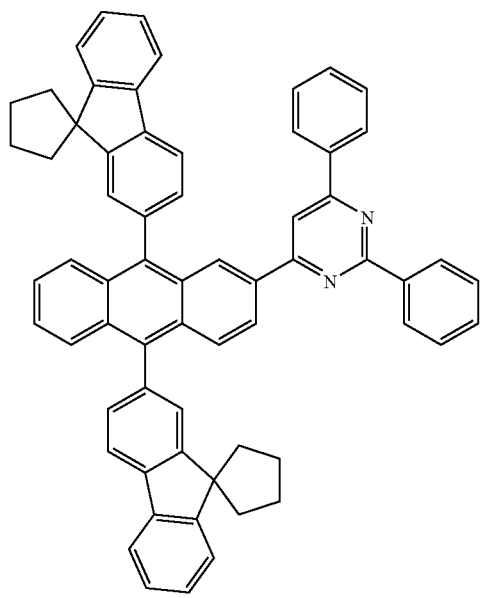

-continued
75
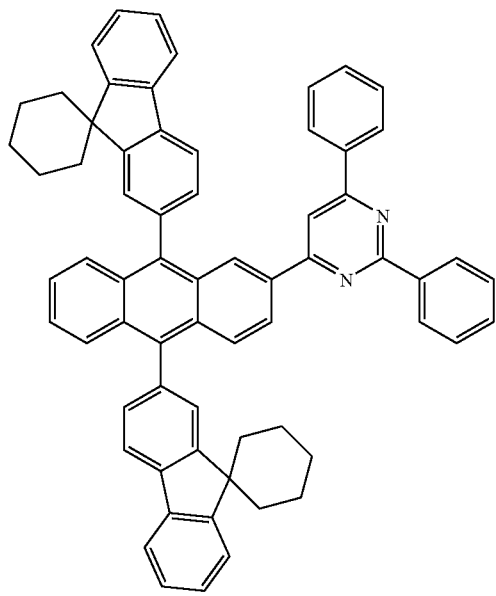
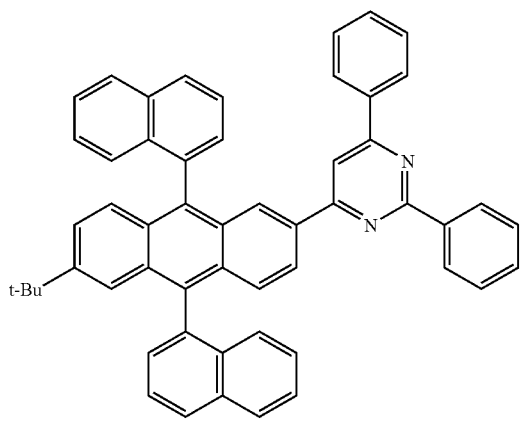
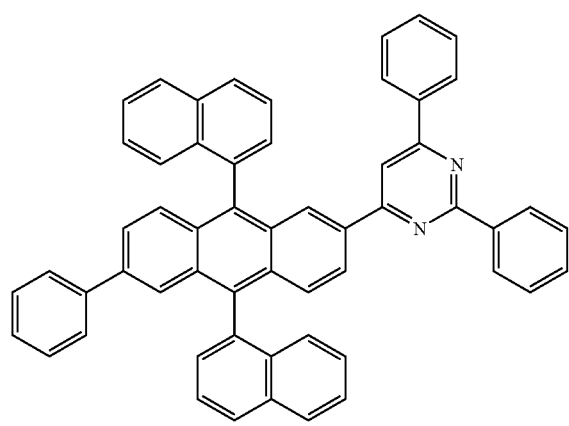
76
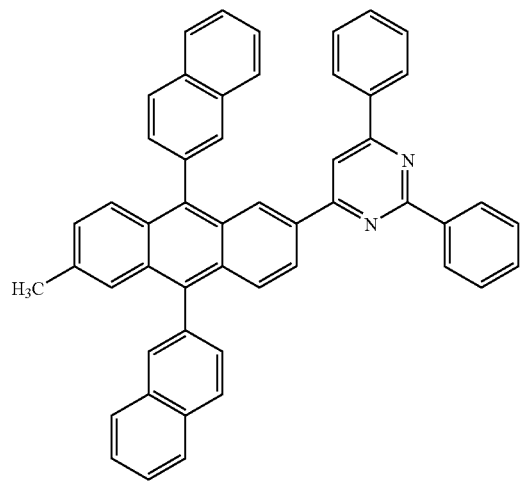
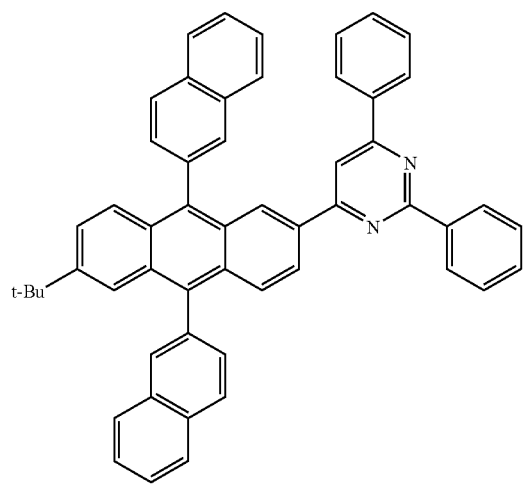
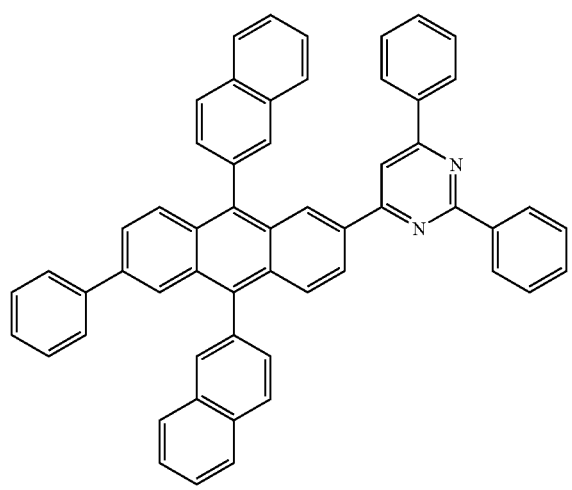

77
78
-continued
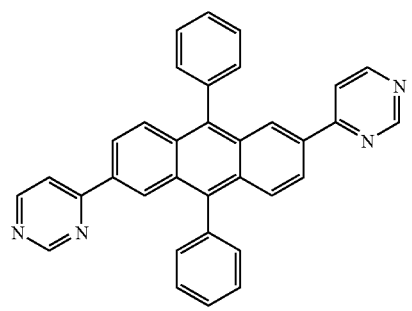
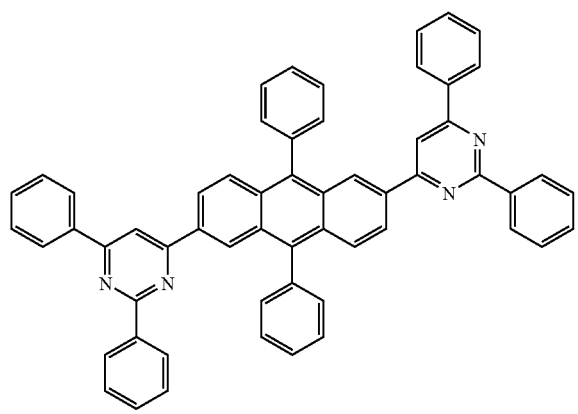
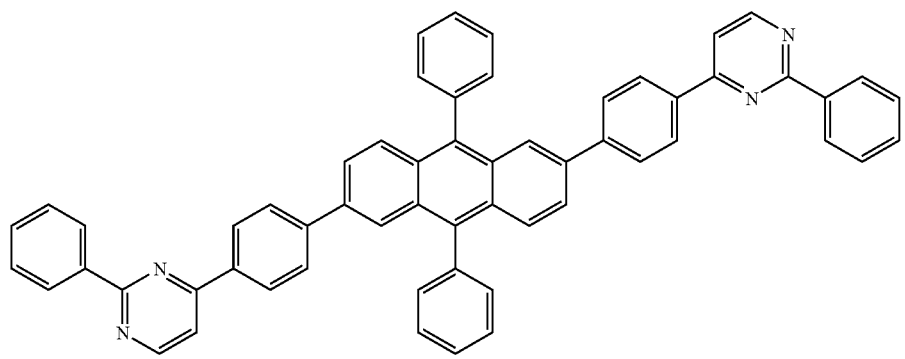
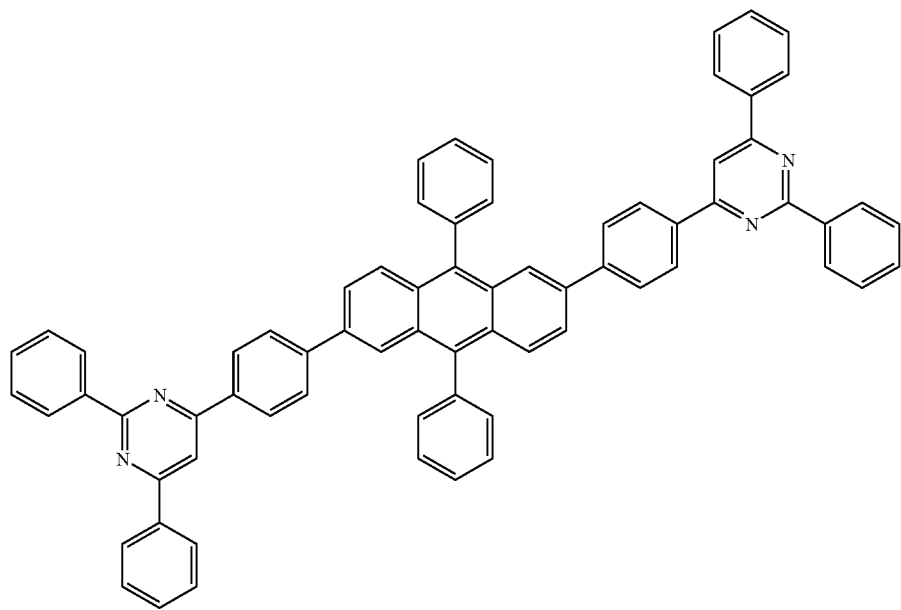

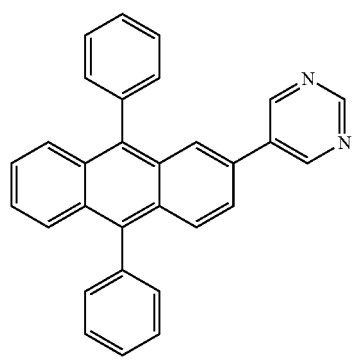
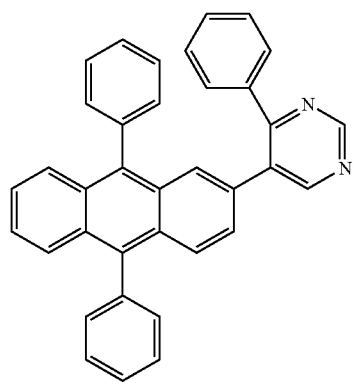
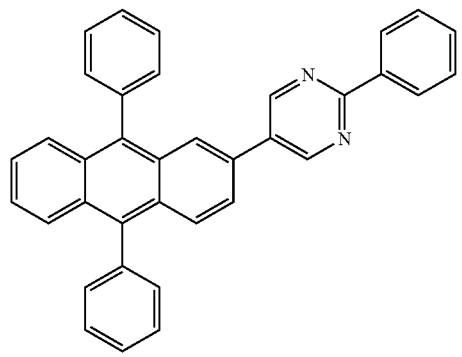
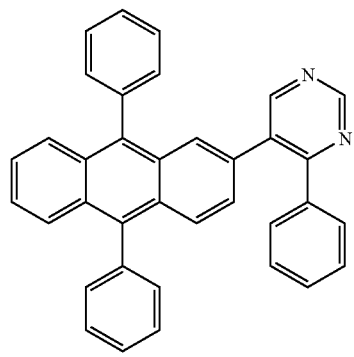
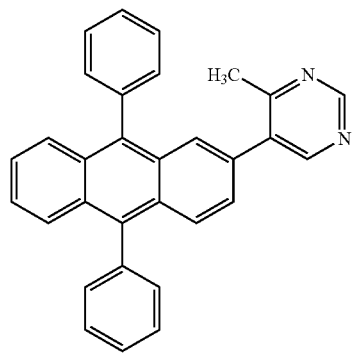
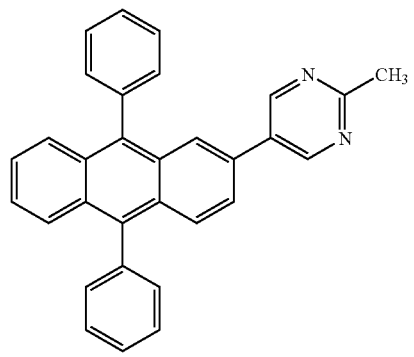
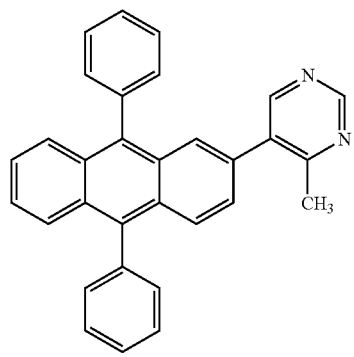
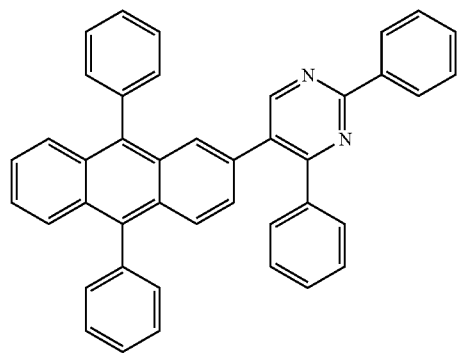

-continued
81
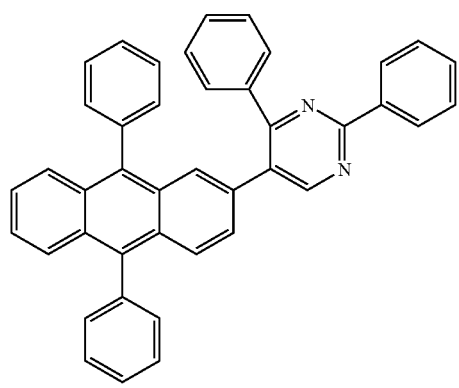
82
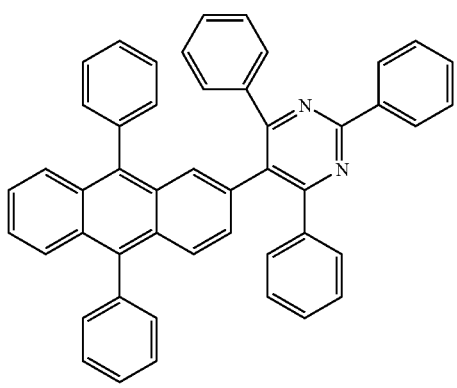
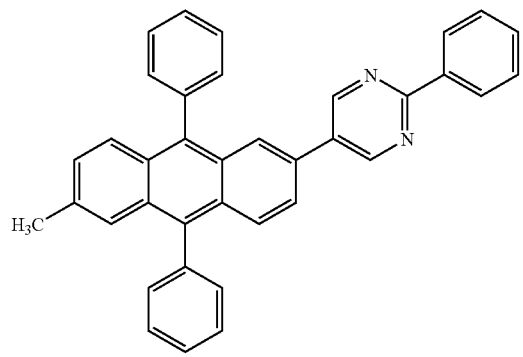
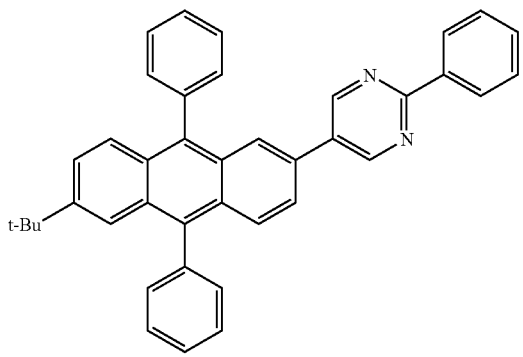
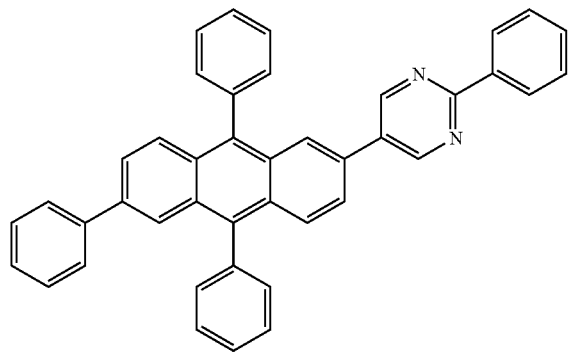
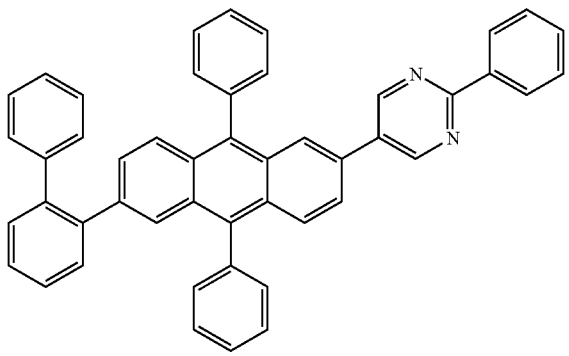
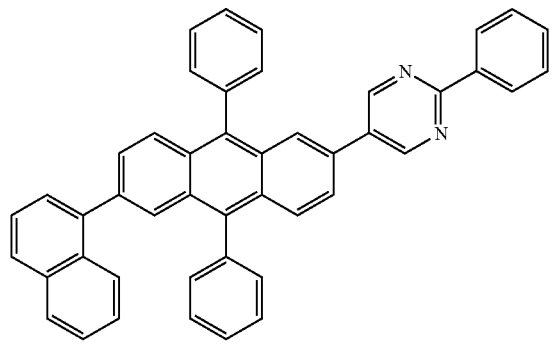
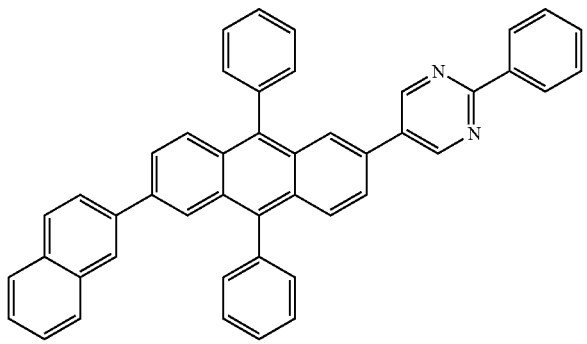

83
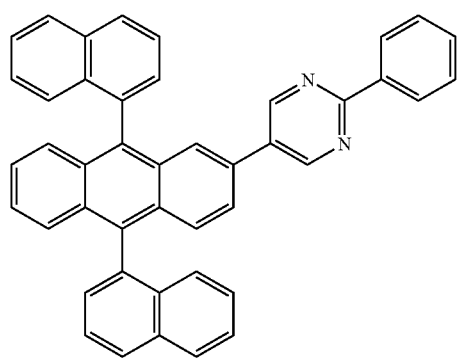
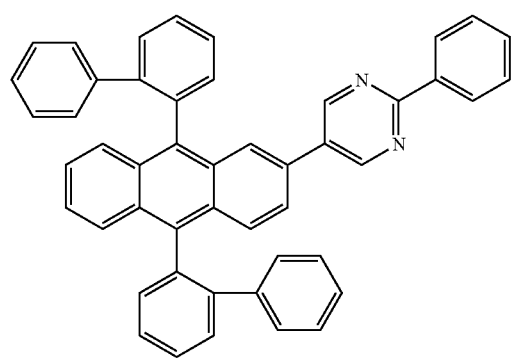
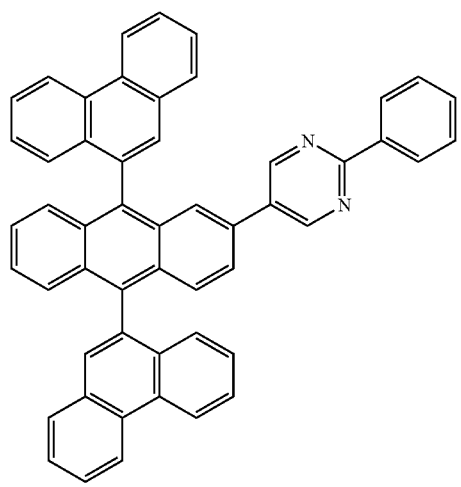
-continued
84
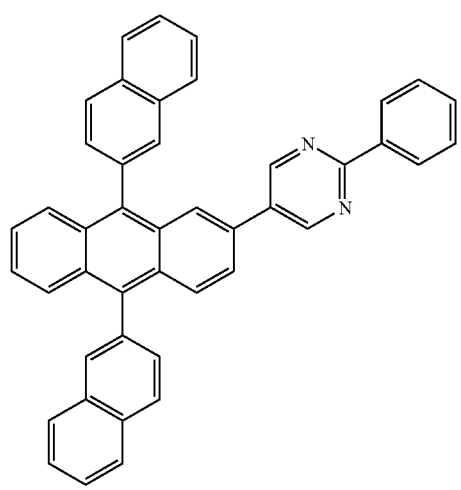
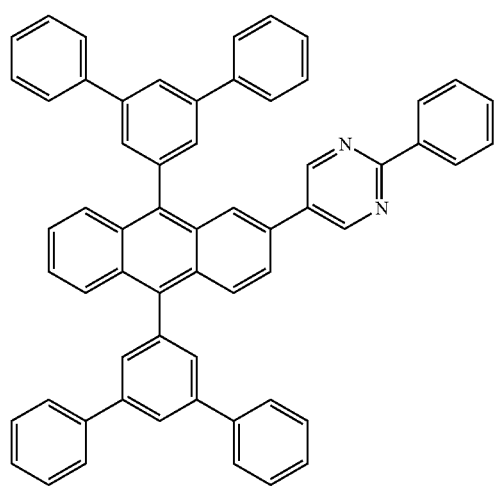
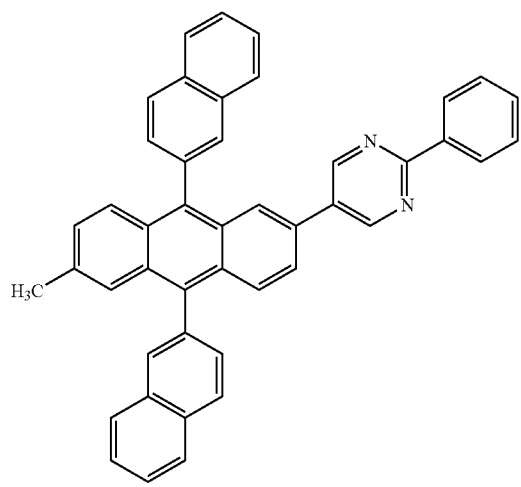

-continued
85
86
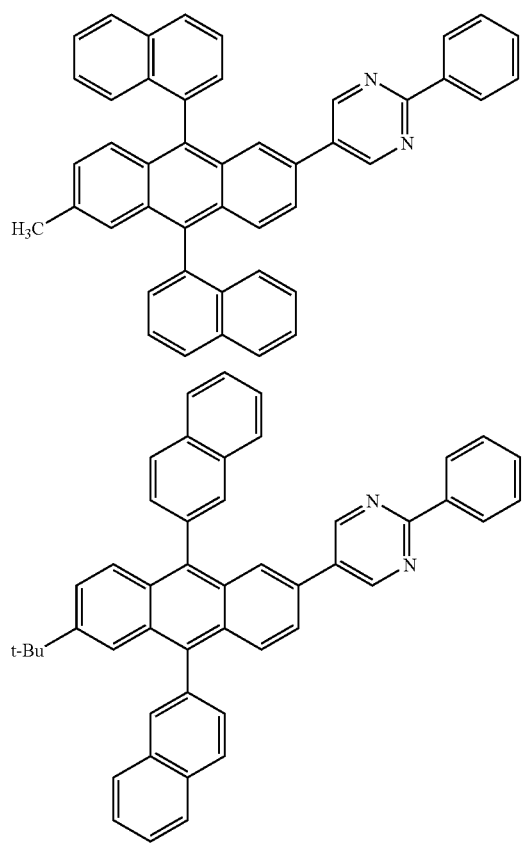
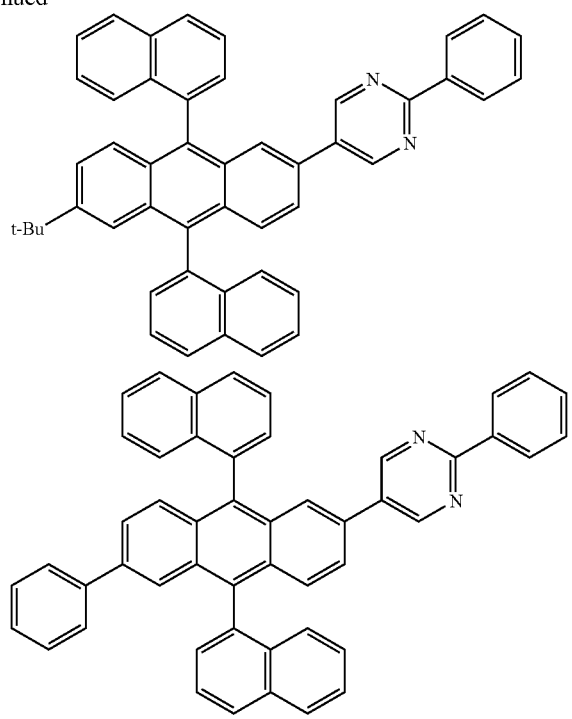
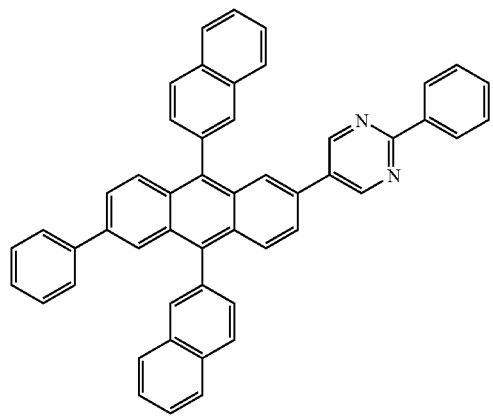
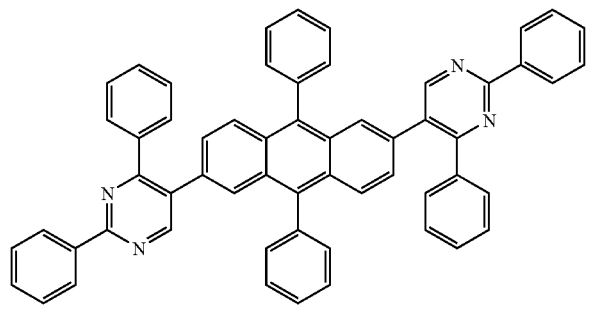
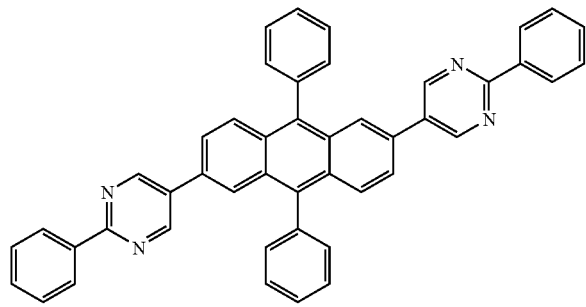
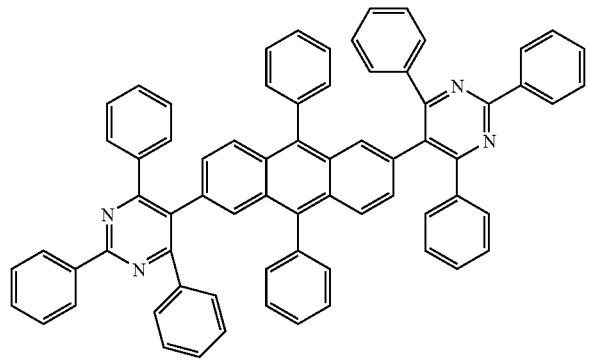

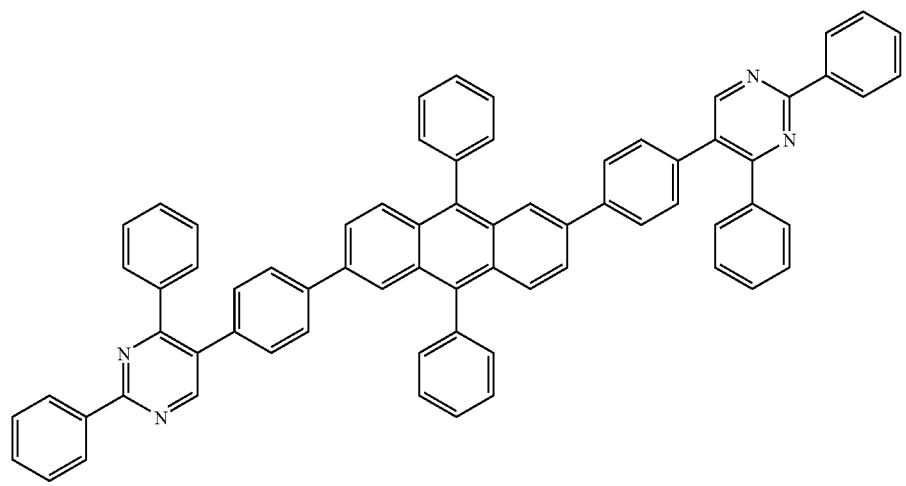
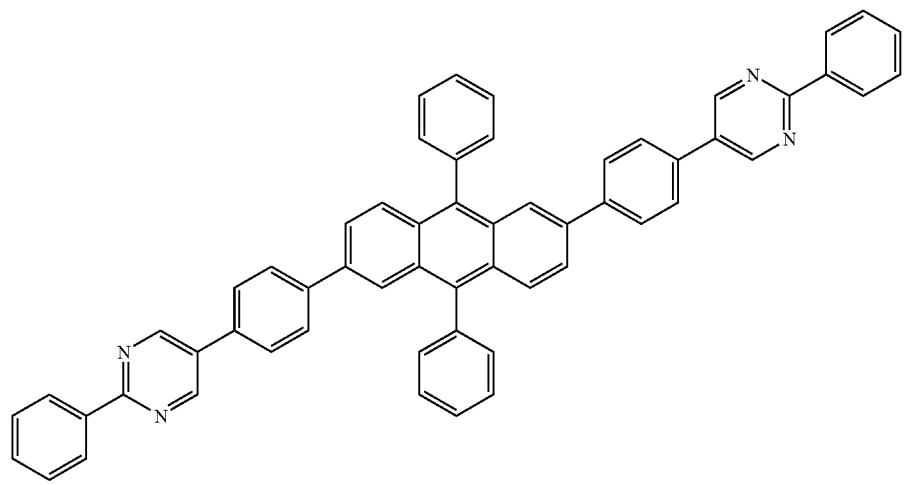
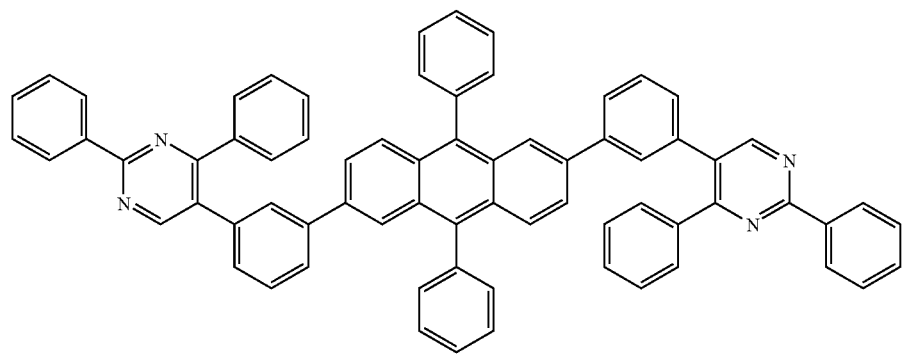

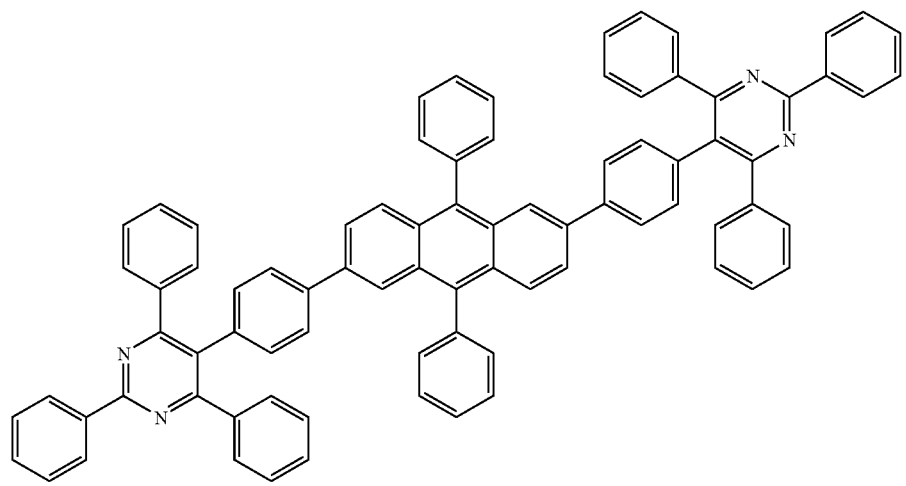
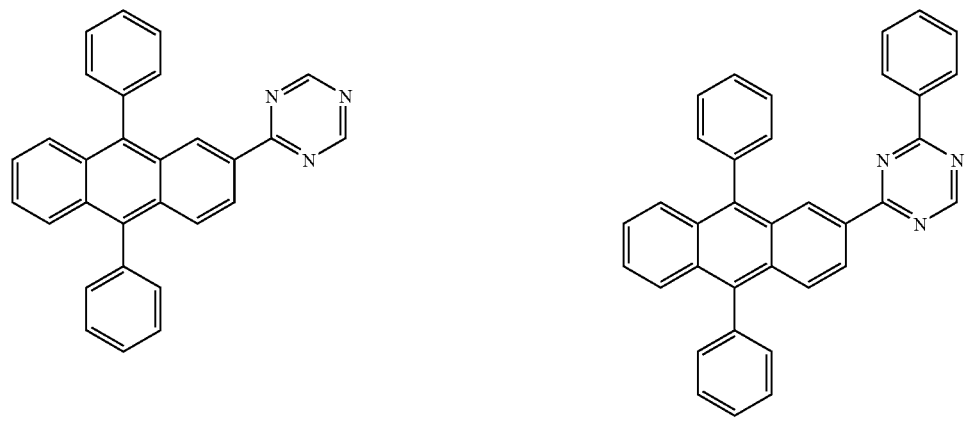
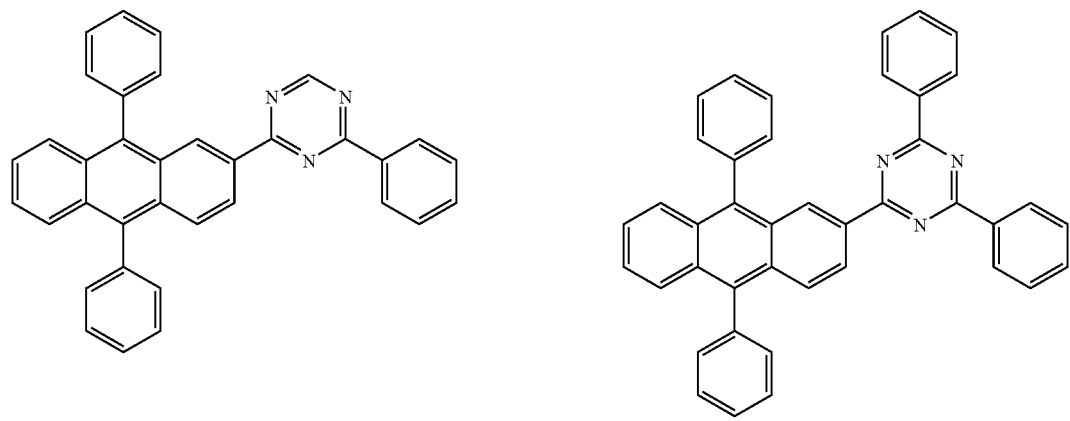

91
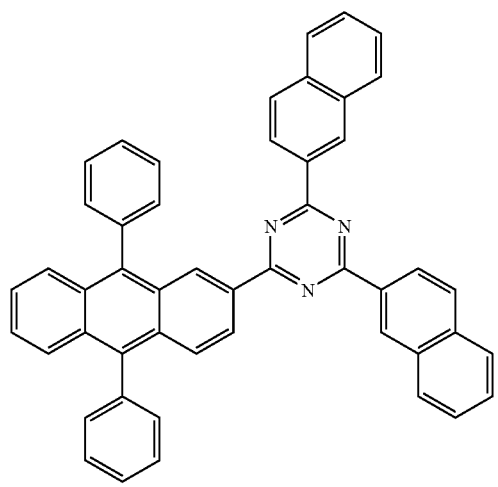
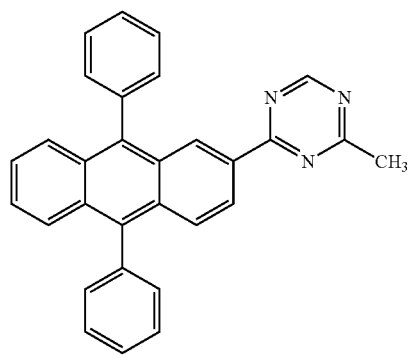
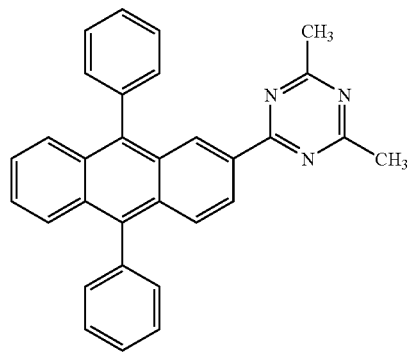
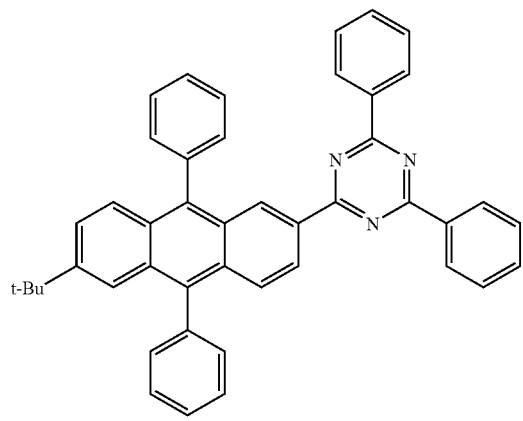
92
-continued
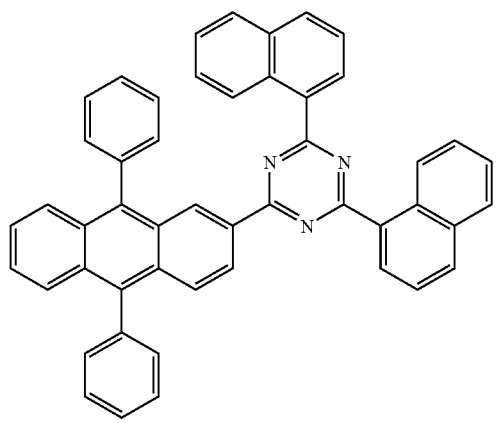
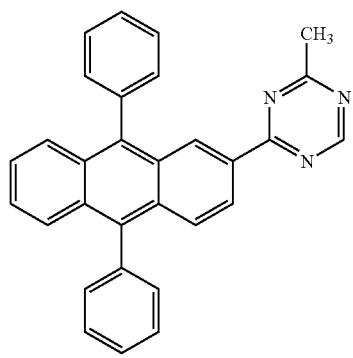
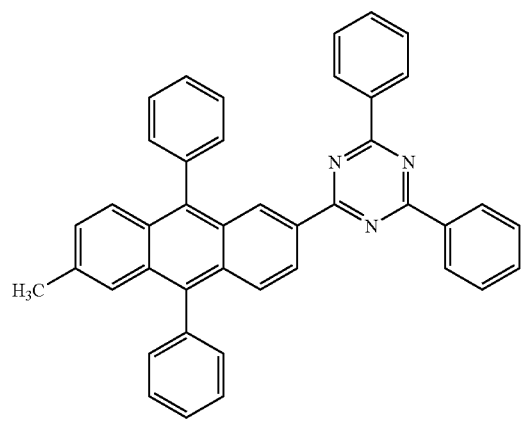
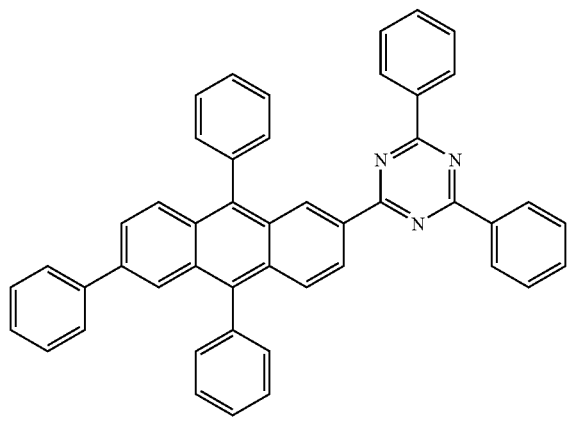

-continued
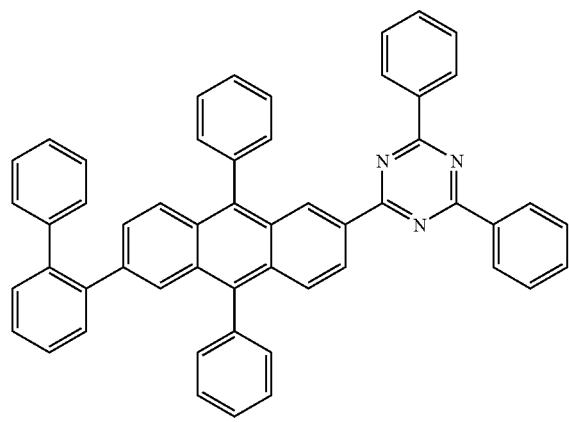
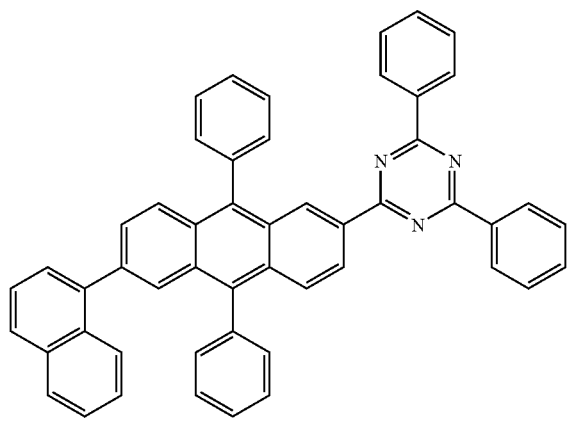
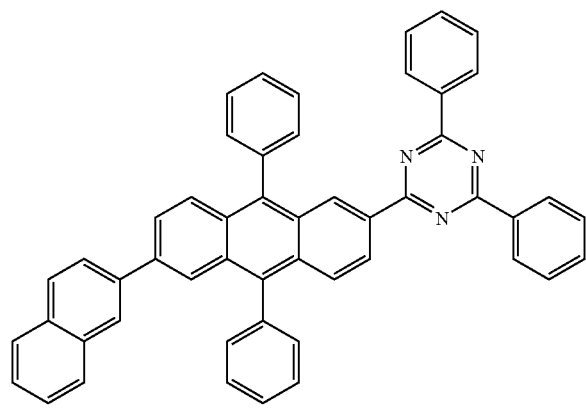
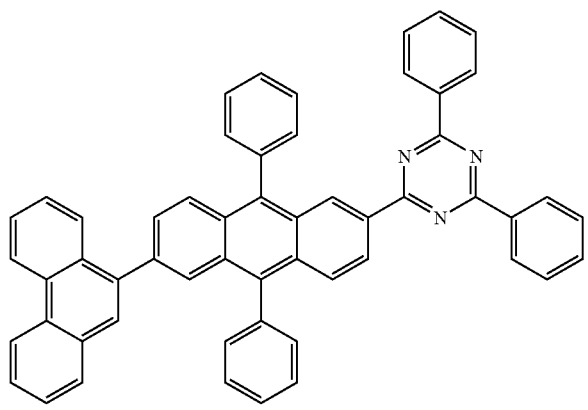
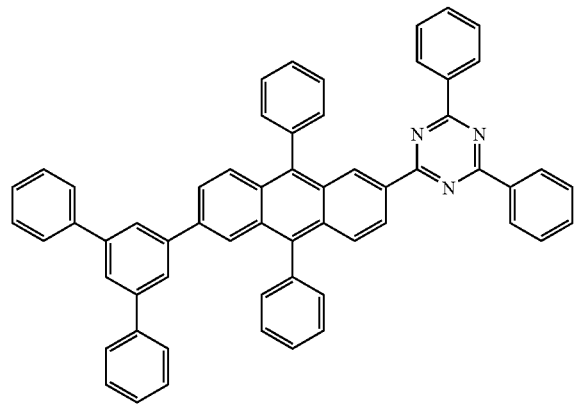
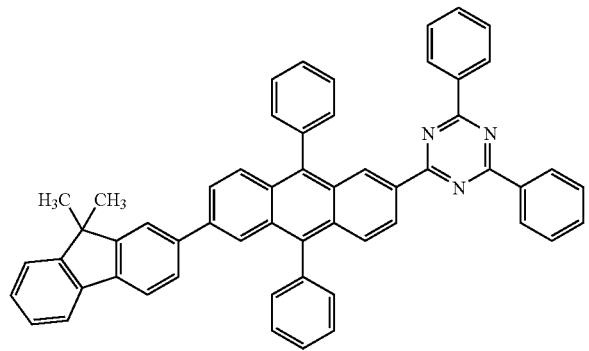
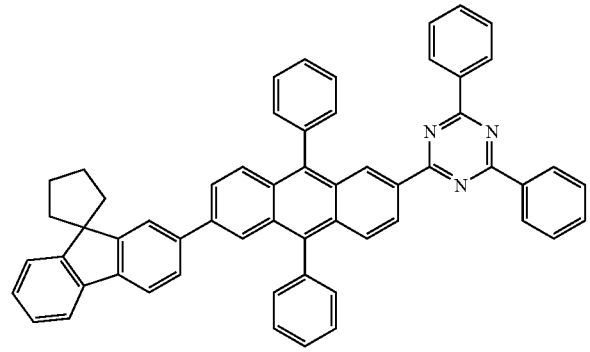
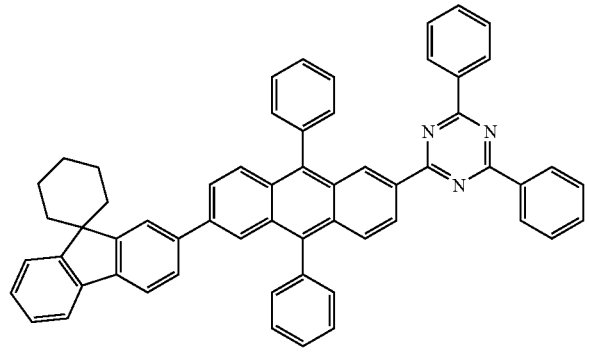

-continued
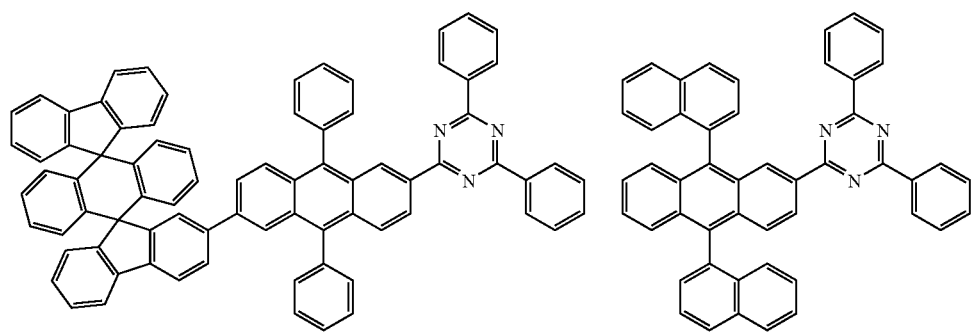
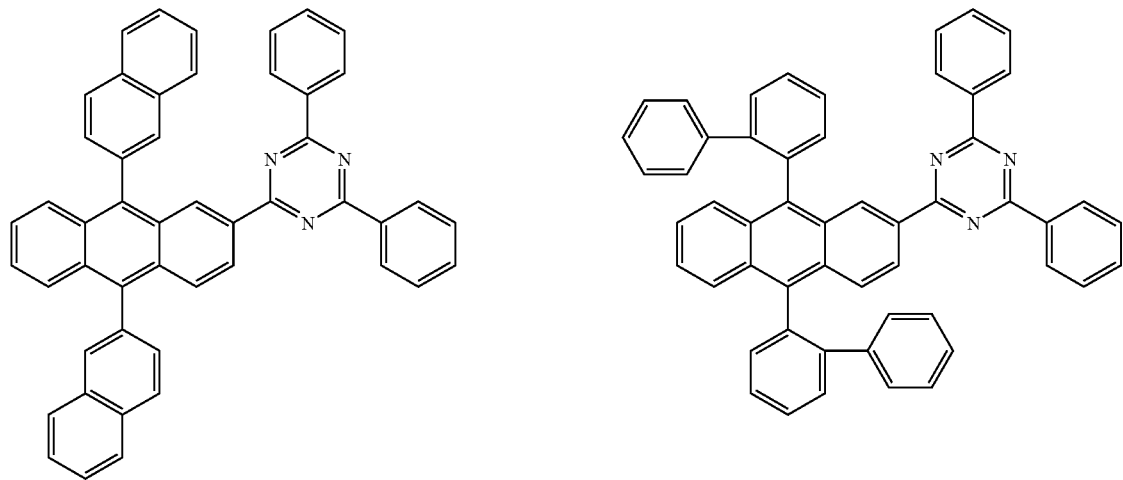
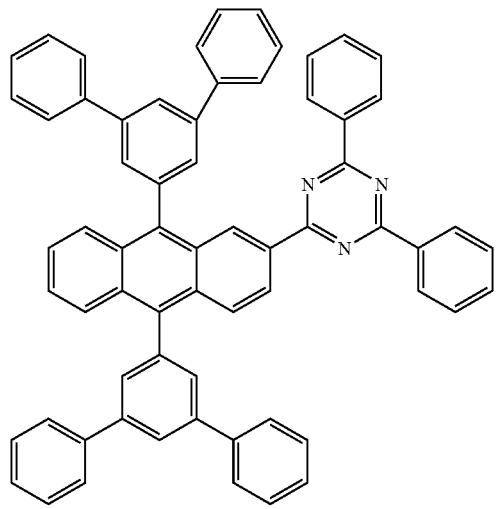
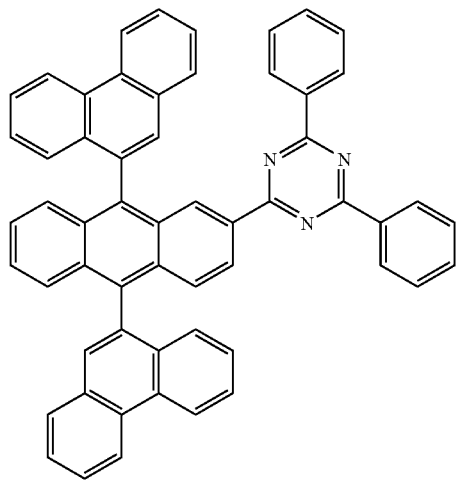

-continued
| 97 | 98 |
|---|---|
| 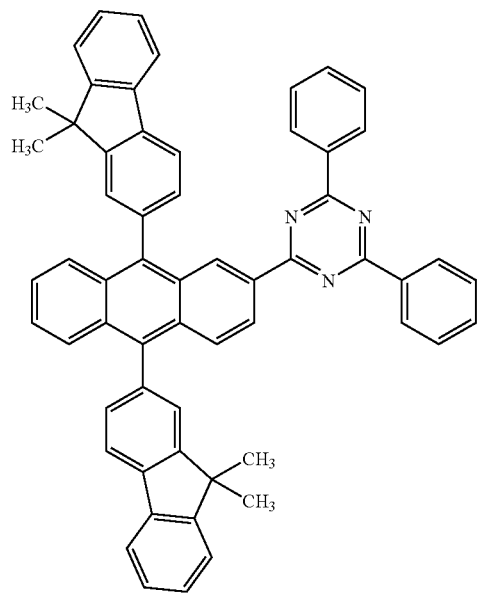 | 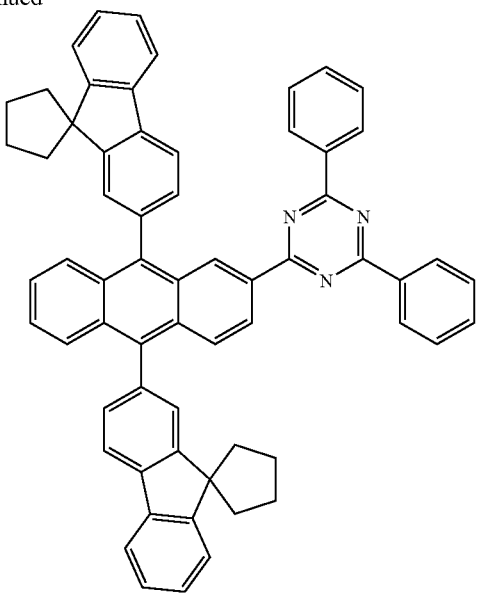 |
| 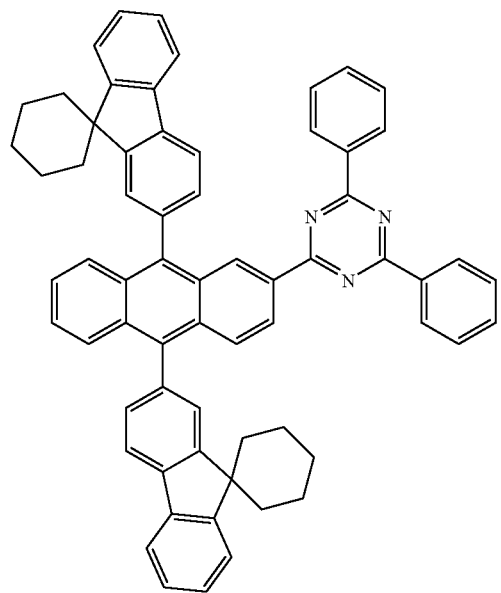 | 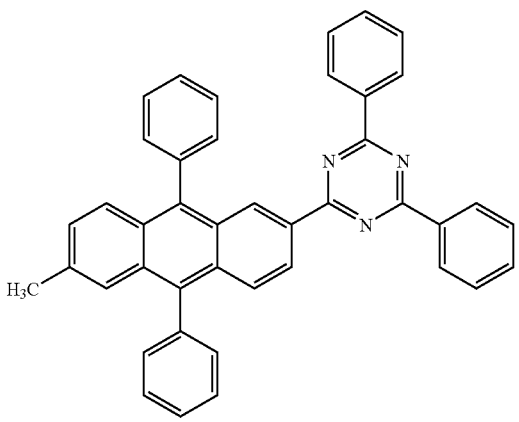 |
| 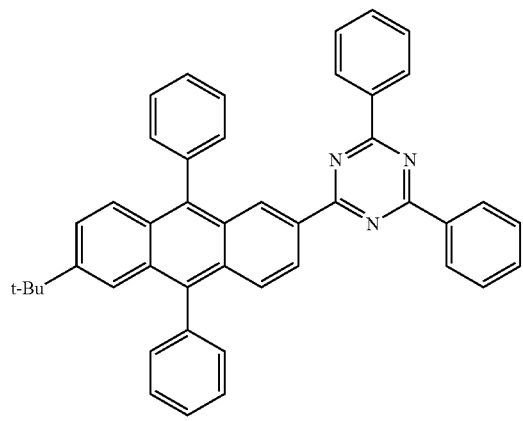 | 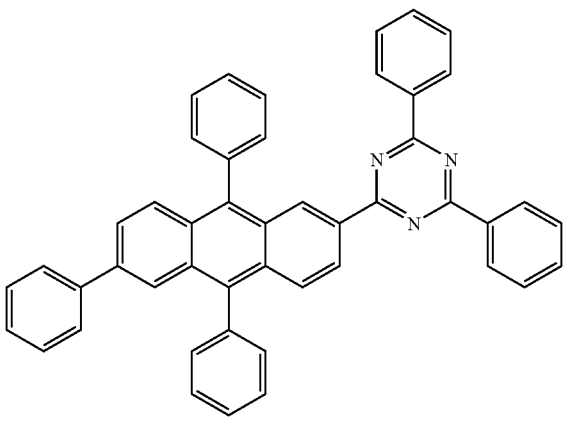 |

-continued
99
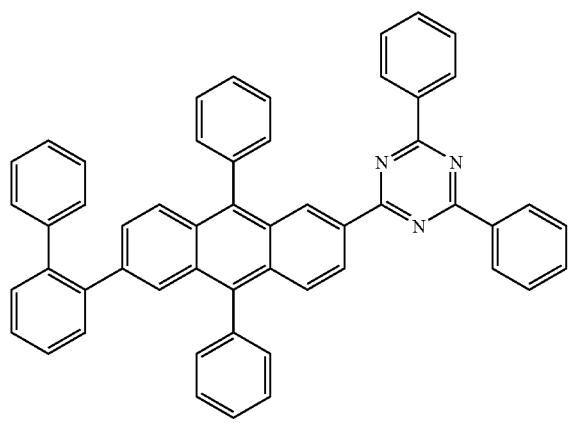
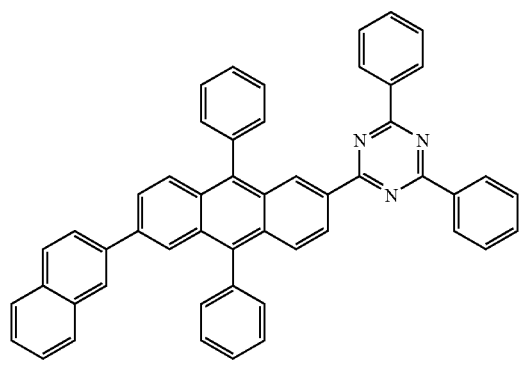
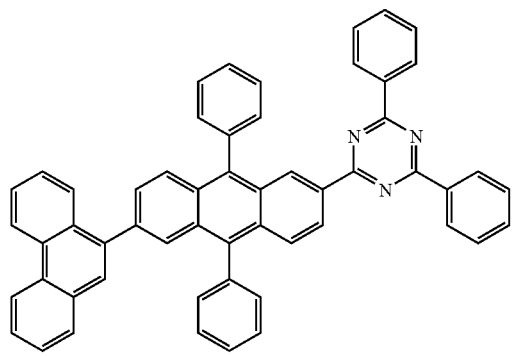
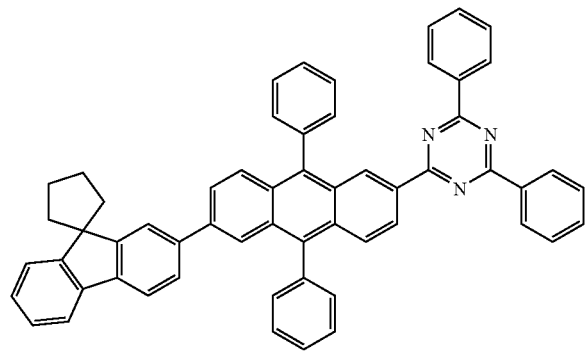
100
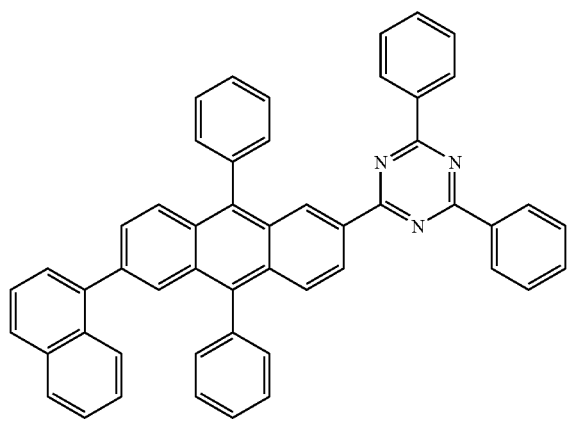
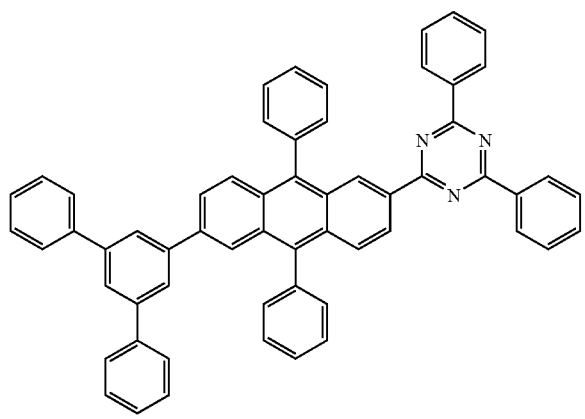
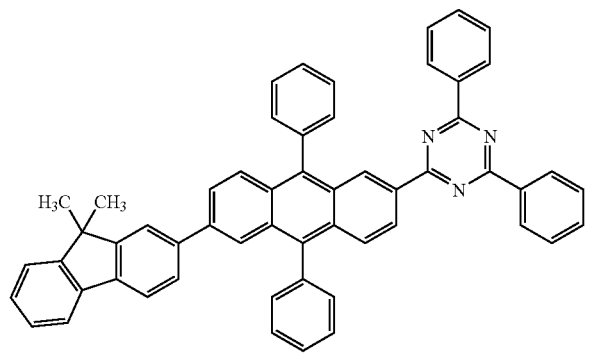
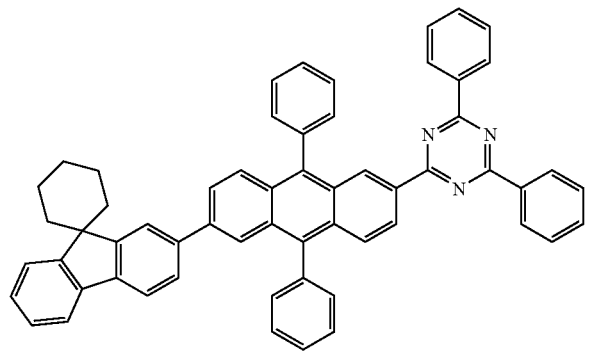

101
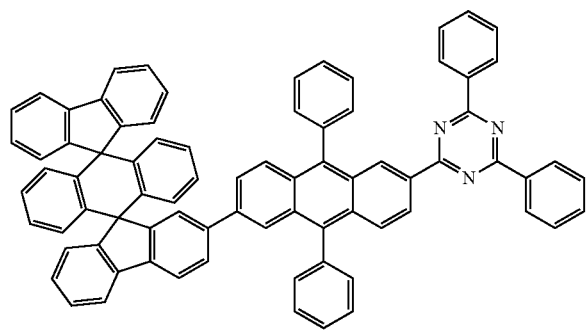
102
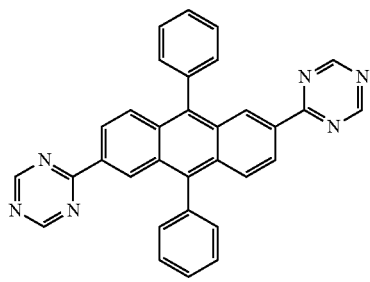
-continued
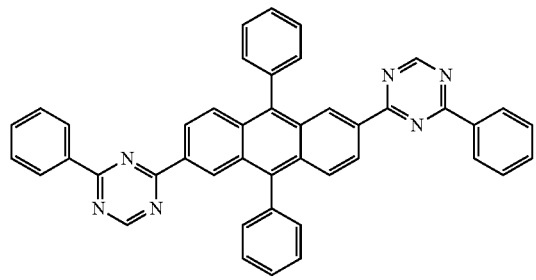
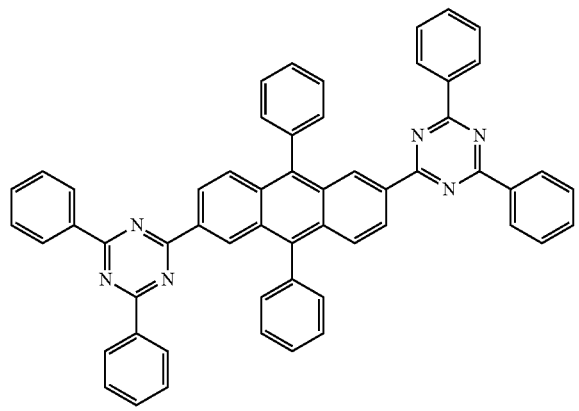
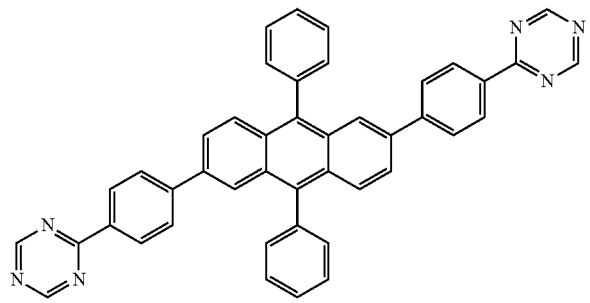
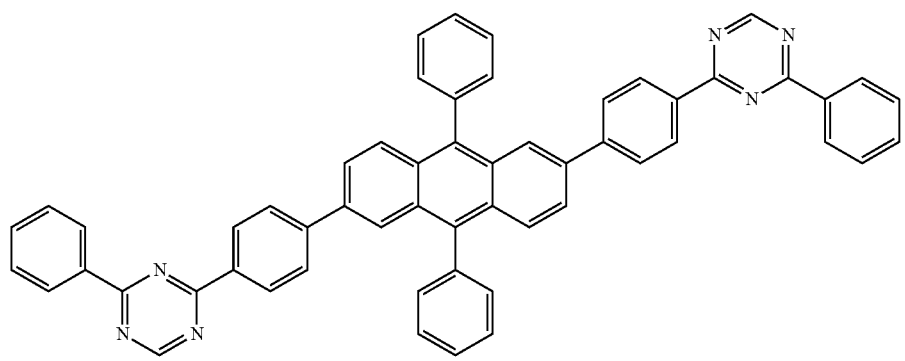

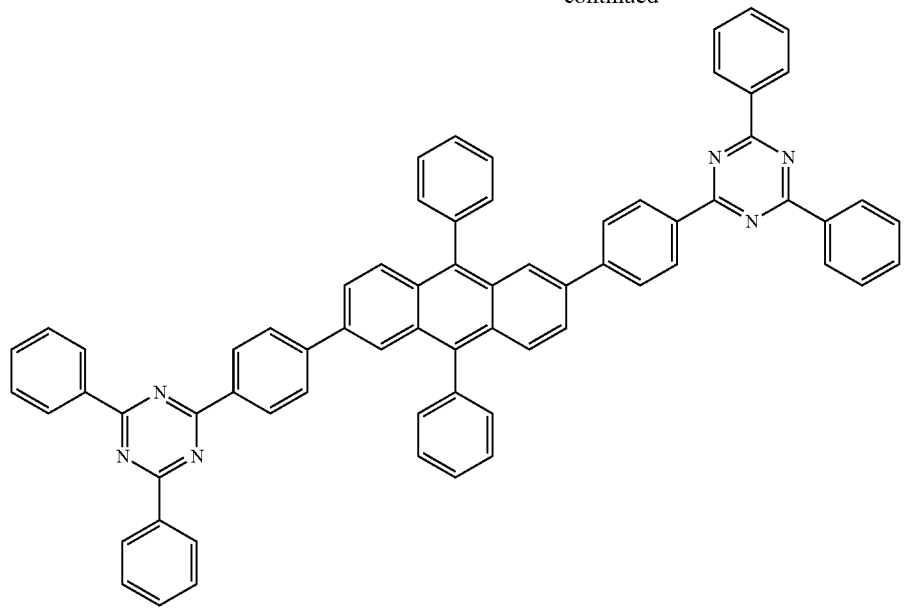

Next, the organic EL device of the present invention shall be explained.

In the organic EL device of the present invention in which an organic thin film layer comprising a single layer or plural layers including at least a light emitting layer is interposed between a cathode and an anode, at least one layer in the above organic thin film layer contains the anthracene derivative of the present invention described above in the form of a single component or a mixed component.

The organic EL device of the present invention contains preferably the anthracene derivative described above primarily in a light emitting zone and contains it more preferably in a light emitting layer.

Further, the organic EL device of the present invention may contain a fluorescent or phosphorescent dopant in addition to the anthracene derivative of the present invention in the light emitting layer described above.

The fluorescent dopant described above is preferably an arylamine compound and/or a styrylamine compound.

The styrylamine compound described above is preferably a compound represented by the following Formula (B):

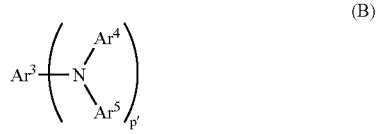

(wherein $Ar^3$ is a group selected from a phenyl group, a biphenyl group, a terphenyl group, a stilbene group and a distyrylaryl group; $Ar^4$ and $Ar^5$ each are a hydrogen atom or an aromatic group having 6 to 20 carbon atoms, and $Ar^3$ to $Ar^5$ may be substituted; p' is an integer of 1 to 4; and more preferably, at least one of $Ar^4$ and $Ar^5$ is substituted with a styryl group).

In this regard, the aromatic group having 6 to 20 carbon atoms includes phenyl, naphthyl, anthranyl, phenanthryl, terphenyl and the like.

The arylamine compound described above is preferably a compound represented by the following Formula (C):

(wherein $Ar^6$ to $Ar^8$ are a substituted or non-substituted aryl group having 5 to 40 ring carbon atoms; and q' is an integer of 1 to 4).

In this regard, the aryl group having 5 to 40 ring carbon atoms includes, for example, phenyl, naphthyl, chrysenyl, naphthacenyl, anthranyl, phenanthryl, pyrenyl, coronyl, biphenyl, terphenyl, pyrrolyl, furanyl, thiophenyl, benzothiophenyl, oxadiazolyl, diphenylanthranyl, indolyl, carbazolyl, pyridyl, benzoquinolyl, fluoroanthenyl, acenaphthofluoranthenyl, stilbene and the like. Preferred substituents for the above aryl group include an alkyl group having 1 to 6 carbon atoms (ethyl, methyl, i-propyl, n-propyl, s-butyl, t-butyl, pentyl, hexyl, cyclopentyl, cyclohexyl and the like) an alkoxy group having 1 to 6 carbon atoms (ethoxy, methoxy i-propoxy, n-propoxy, s-butoxy, t-butoxy, pentoxy, hexyloxy, cyclopentoxy, cyclohexyloxy and the like), an aryl group having 5 to 40 ring carbon atoms, an amino group substituted with an aryl group having 5 to 40 ring carbon atoms, an ester group having an aryl group having 5 to 40 ring carbon atoms, an ester group having an alkyl group having 1 to 6 carbon atoms, a cyano group, a nitro group, a halogen atom and the like.

The phosphorescent dopant includes metal complex compounds and is preferably a metal complex compound containing at least one metal selected from Ir, Ru, Pd, Pt, Os and Re, and a ligand has preferably at least one skeleton selected from a phenylpyridine skeleton, a bipyridyl skeleton and a phenanthroline skeleton. The specific examples of the above metal complex include tris(2-phenylpyridine)iridium, tris(2-phenylpyridine)-ruthenium, tris(2-phenylpyridine)palladium, bis(2-phenylpyridine)platinum, tris(2-phenylpyridine)osmium, tris(2-phenylpyridine)rhenium, octaethylplatinum porphyrin, octaphenylplatinum porphyrin, octaethylpalladium porphyrin, and octaphenylpalladium porphyrin and the like. However, they shall not be restricted to the above compounds, and the suited complexes are selected from the viewpoints of the luminescent color required, the device performances and relation with the host compound.

In the organic EL device of the present invention, the organic thin film layer described above has a hole injecting layer and/or a hole transporting layer, and the above hole injecting layer and/or hole transporting layer may contain the anthracene derivative of the present invention in the form of a single component or a mixed component. The organic thin film layer described above has an electron injecting layer and/or an electron transporting layer, and the above electron injecting layer and/or electron transporting layer may contain the anthracene derivative of the present invention in the form of a single component or a mixed component.

The device structure of the organic EL device of the present invention shall be explained below.

(1) Structure of the Organic EL Element

The typical examples of the device structure of the organic EL device of the present invention include structures such as:
(1) Anode/light emitting layer/cathode
(2) Anode/hole injecting layer/light emitting layer/cathode
(3) Anode/light emitting layer/electron injecting layer/cathode
(4) Anode/hole injecting layer/light emitting layer/electron injecting layer/cathode
(5) Anode/organic semiconductor layer/light emitting layer/cathode
(6) Anode/organic semiconductor layer/electron barrier layer/light emitting layer/cathode
(7) Anode/organic semiconductor layer/light emitting layer/adhesion improving layer/cathode
(8) Anode/hole injecting layer/hole transporting layer/light emitting layer/electron injecting layer/cathode
(9) Anode/insulating layer/light emitting layer/insulating layer/cathode
(10) Anode/inorganic semiconductor layer/insulating layer/light emitting layer/insulating layer/cathode
(11) Anode/organic semiconductor layer/insulating layer/light emitting layer/insulating layer/cathode
(12) Anode/insulating layer/hole injecting layer/hole transporting layer/light emitting layer/insulating layer/cathode
(13) Anode/insulating layer/hole injecting layer/hole transporting layer/light emitting layer/electron injecting layer/cathode Among them usually the structure of (8) is preferably used but it shall not be restricted to them.

The anthracene derivative of the present invention may be used in any organic thin film layer of the organic EL device and can be used in the light emitting zone or the electron transporting zone, and it is used preferably in the electron transporting zone, particularly preferably in the electron infecting and transporting layer, whereby the molecules are less liable to be crystallized, and a yield in producing the organic EL device is improved.

An amount of the anthracene derivative of the present invention which is added to the organic thin film layer is preferably 30 to 100 mole %

(2) Light Transmitting Substrate

The organic EL device of the present invention is prepared on a light transmitting substrate. The light transmitting substrate referred to in this case is a substrate for supporting the organic EL device, and it is preferably a flat substrate in which light in a visible region of 400 to 700 nm has a transmittance of 50% or more.

To be specific, it includes a glass plate, a polymer plate and the like. In particular, the glass plate includes soda lime glass, barium and strontium-containing glass, lead glass, aluminosilicate glass, borosilicate glass, barium borosilicate glass, quartz and the like. The polymer plate includes polycarbonate, acryl, polyethylene terephthalate, polyether sulfide, polysulfone and the like.

(3) Anode

An anode in the organic EL device of the present invention has a function to inject a hole into the hole transporting layer or the light emitting layer, and it is effective that the anode has a work function of 4.5 eV or more. The specific examples of a material for the anode used in the present invention include indium tin oxide alloy (ITO) indium zinc oxide alloy (IZO), zinc oxide (NESA), gold, silver, platinum, copper and the like.

The anode can be prepared by forming a thin film of the above electrode substances by a method such as a vapor deposition method, a sputtering method and the like.

When light emitted from the light emitting layer is taken out from the anode, a light transmittance of the anode based on the light emitted is preferably larger than 10%. A sheet resistance of the anode is preferably several hundred $\Omega$/square or less. A film thickness of the anode is selected, though depending on the material, in a range of usually 10 nm to 1 μm, preferably 10 to 200 nm.

(4) Light Emitting Layer

The light emitting layer in the organic EL device has the following functions of (1) to (3) in combination.
(1) Injecting function: a function in which a hole can be injected from an anode or a hole injecting layer and an electron can be infected from a cathode or an electron injecting layer when an electric field is applied.
(2) Transporting function: a function in which a charge (electron and hole) injected is transferred by virtue of a force of an electric field.
(3) Light emitting function: a function in which a field for recombination of an electron and a hole is provided and in which this is connected to light emission.

Provided that a difference between an easiness in injection of a hole and an easiness in injection of an electron may be present and that a difference may be present in a transporting ability shown by the mobilities of a hole and an electron, and any one of the charges is preferably transferred.

A publicly known method such as, for example, a vapor deposition method, a spin coating method, an LB method and the like can be applied as a method for forming the above light emitting layer. In particular, the light emitting layer is preferably a molecular deposit film. In this case, the molecular deposit film means a thin film formed by depositing a material compound staying in a gas phase state and a film formed by solidifying a material compound staying in a solution state or a liquid phase state, and the above molecular deposit film can usually be distinguished from a thin film (molecular deposit film) formed by the LB method by a difference in an aggregation structure and a higher order structure and a functional difference originating in it.

Further, as disclosed in Japanese Patent Application Laid-Open No. 5178/1982, the light emitting layer can be formed as well by dissolving a binding agent such as a resin and a material compound in a solvent to prepare a solution and then forming a thin film from the solution by a spin coating method and the like.

In the present invention, publicly known light emitting materials other than the anthracene derivative of the present invention may be added if necessary to the light emitting layer as long as the object of the present invention is not damaged. Further, a light emitting layer containing a different publicly known light emitting material may be laminated on the light emitting layer containing the anthracene derivative of the present invention.

(5) Hole Injecting and Transporting Layer

The hole injecting and transporting layer is a layer for assisting injection of a hole into the light emitting layer to transport it to the light emitting region, and it has a large hole mobility and shows a small ionization energy of usually 5.5 eV or less. A material which transports a hole to the light emitting layer by a lower electric field strength is preferred for the above hole injecting and transporting layer, and more preferred is a material in which a mobility of a hole is at least $10^{-4}$ cm$^2$/V·second in applying an electric field of, for example, $10^4$ to $10^6$ V/cm.

When the anthracene derivative of the resent invention is used in the hole transporting zone, the hole injecting and transporting layer may be formed from the anthracene derivative of the present invention alone or it may be used in a mixture with other materials.

The materials for forming the hole injecting and transporting layer by mixing with the anthracene derivative of the present invention shall not specifically be restricted as long as they have the preferred properties described above, and capable of being used are optional materials selected from materials which have so far conventionally been used as charge transporting materials of holes in photoconductive materials and publicly known materials which are used for a hole injecting and transporting layer in an organic EL device.

The specific examples thereof include triazole derivatives (refer to U.S. Pat. No. 3,112,197 and the like), oxadiazole derivatives (refer to U.S. Pat. No. 3,189,447 and the like), imidazole derivatives (refer to Japanese Patent Publication No 16096/1962 and the like) polyarylalkane derivatives (refer to U.S. Pat. No. 3,615,402, ditto U.S. Pat. No. 3,820,989 and ditto U.S. Pat. No. 3,542,544, Japanese Patent Publication No. 555/1970 and ditto 10983/1976 and Japanese Patent Application Laid-Open No. 93224/1976, ditto 17105/1980, ditto 4148/1981, ditto 108667/1980, ditto 156953/1980 and ditto 36656/1981 and the like), pyrazoline derivatives and pyrazolone derivatives (refer to U.S. Pat. No. 3,180,729 and U.S. Pat. No. 4,278,746 and Japanese Patent Application Laid-Open No. 88064/1980, ditto 88065/1980, ditto 105537/1974, ditto 51086/1980, ditto 80051/1981, ditto 88141/1981/ ditto 45545/1982, ditto 112637/1979 and ditto 74546/1980 and the like), phenylenediamine derivatives (refer to U.S. Pat. No. 3,615,404, Japanese Patent Publication No. 10105/1976, ditto 3712/1971 and ditto 25336/1972 and Japanese Patent Application Laid-Open No. 53435/1979, ditto 110536/1979 and ditto 119925/1979 and the like), arylamine derivatives (refer to U.S. Pat. No. 3,567,450, ditto U.S. Pat. No. 3,180, 703, ditto U.S. Pat. No. 3,240,597, ditto U.S. Pat. No. 3,658, 520, ditto U.S. Pat. No. 4,232,103, ditto U.S. Pat. No. 4,175, 961 and ditto U.S. Pat. No. 4,012,376, Japanese Patent Publication No 35702/1974 and ditto 27577/1964, Japanese Patent Application Laid-Open No. 144250/1980, ditto 119132/1981 and ditto 22437/1981 and German Patent 1,110,518 and the like), amino-substituted chalcone derivatives (refer to U.S. Pat. No. 3,526,501 and the like), oxazole derivatives (disclosed in U.S. Pat. No. 3,257,203 and the like), styrylanthracene derivatives (refer to Japanese Patent Application Laid-Open No. 46234/1981 and the like), fluorenone derivatives (refer to Japanese Patent Application Laid-Open No. 110837/1979 and the like), hydrazone derivatives (refer to U.S. Pat. No. 3,717,462, Japanese Patent Application Laid-Open No. 59143/1979, ditto 52063/1980, ditto 52064/1980, ditto 46760/1980, ditto 85495/1980, ditto 11350/1982 and ditto 148749/1982, Japanese Patent Application Laid-Open No. 311591/1990 and the like), stilbene derivatives (Japanese Patent Application Laid-Open No. 210363/1986, ditto 228451/1986, ditto 14642/1986, ditto 72255/1986, ditto 47646/1987, ditto 36674/1987, ditto 10652/1987, ditto 30255/1987, ditto 93455/1985, ditto 94462/1985, ditto 174749/1985 and ditto 175052/1985 and the like), silazane derivatives (U.S. Pat. No. 4,950,950), polysilane base (Japanese Patent Application Laid-Open No. 204996/1990), aniline base copolymers (Japanese Patent Application Laid-Open No. 282263/1990) and electroconductive high molecular oligomers (particularly thiophene oligomers) disclosed in Japanese Patent Application Laid-Open No. 211399/1989.

The compounds described above can be used as the material for the hole injecting and transporting layer, and preferably used are porphyrin compounds (disclosed in Japanese Patent Application Laid-Open No. 295695/1988 and the like), aromatic tertiary amine compounds and styrylamine compounds (refer to U.S. Pat. No. 4,127,412 and Japanese Patent Application Laid-Open No. 27033/1978, ditto 58445/1979, ditto 149634/1979, ditto 64299/1979, ditto 79450/1980, ditto 144250/1980, ditto 119132/1981, ditto 295558/1986, ditto 98353/1986 and ditto 295695/1988 and the like), and the aromatic tertiary amine compounds are particularly preferably used.

Further, capable of being given are compounds having two fused aromatic rings in a molecule described in U.S. Pat. No. 5,061,569, for example, 4,4'-bis(N-(1-naphthyl)-N-phenylamino)biphenyl (hereinafter abbreviated as NPD) and 4,4', 4"-tris(N-(3-methylphenyl)-N-phenylamino)triphenylamine (hereinafter abbreviated as MTDATA) in which three triphenylamine units are combined in the form of a star burst type disclosed in Japanese Patent Application Laid-open No. 308688/1992.

Further, inorganic compounds such as p type Si, p type SiC and the like can also be used as the material for the hole injecting and transporting layer in addition to the aromatic dimethylidene base compounds described above shown as the material for the light emitting layer.

The hole injecting and transporting layer can be formed by making a thin film from the anthracene derivative of the present invention and the compounds described above by a publicly known method such as, for example, a vacuum vapor deposition method, a spin coating method, a casting method, an LB method and the like. A film thickness of the hole injecting and transporting layer shall not specifically be restricted, and it is usually 5 nm to 5 μm. The above hole injecting and transporting layer may be constituted from a single layer comprising at least one of the materials described above as long as the anthracene derivative of the resent invention is contained in the hole transporting zone, and a hole injecting and transporting layer comprising a compound which is different from the compound used in the hole injecting and transporting layer described above may be laminated thereon.

Further, an organic semiconductor layer may be provided as a layer for assisting injection of a hole or injection of an electron into the light emitting layer, and the layer having a conductance of $10^{-10}$ S/cm or more is suited Capable of being used as a material for the above organic semiconductor layer are conductive oligomers such as thiophene-containing oligomers and aryl amine-containing oligomers disclosed in Japanese Patent Application Laid-Open No. 193191/1996 and conductive dendrimers such as arylamine-containing dendrimers.

(6) Electron Injecting and Transporting Layer

The electron injecting and transporting layer is a layer for assisting injection of an electron into the light emitting layer to transport it to the light emitting region, and it has a large electron mobility. Also, the adhesion improving layer is a layer comprising particularly a material having a good adhesive property with the cathode in the above electron injecting layer. The materials used for the electron injecting and transporting layer are suitably metal complexes of 8-hyroxyquinoline or derivatives thereof.

The specific examples of the above metal complexes of 8-hyroxyquinoline or the derivatives thereof include metal chelate oxynoid compounds containing chelates of oxine (in general, 8-quinolinol or 8-hyroxyquinoline), and, for examples tris(8-quinolinol)aluminum (Alq) can be used as the electron injecting material.

Also, the oxadiazole derivative includes electron transmitting compounds represented by the following formulas:

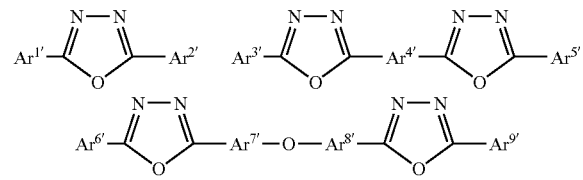

(wherein $Ar^{1'}$, $Ar^{2'}$, $Ar^{3'}$, $Ar^{5'}$, $Ar^{6'}$ and $Ar^{9'}$ each represent a substituted or non-substituted aryl group, and they may be the same as or different from each other; $Ar^{4'}$, $Ar^{7'}$ and $Ar^{8'}$ each represent a substituted or non-substituted arylene group, and they may be the same as or different from each other).

In this connection, the aryl group includes phenyl, biphenyl, anthranyl, perylenyl and pyrenyl, and the arylene group includes phenylene, naphthylene, biphenylene, anthranylene, perylenylene and pyrenylene. Substituents therefor include an alkyl group having 1 to 10 carbon atoms, an alkoxy group having 1 to 10 carbon atoms and a cyano group. The above electron transmitting compounds have preferably a thin film-forming property.

The following compounds can be given as the specific examples of the above electron transmitting compounds:

The organic EL device of the present invention contains preferably a reducing dopant in the electron injecting layer and/or the electron transporting layer, and the reducing dopant may be contained in a region which transports an electron or an interfacial region between the cathode and the organic thin film layer. In this case, the reducing dopant is defined by a substance which can reduce an electron transporting compound. Accordingly, various compounds can be used as long as they have a reducing property of some extent, and capable of being suitably used is at least one substance selected from the group cons-sting of, for example, alkali metals, alkaline earth metals, rare earth metals, oxides of alkali metals, halides of alkali metals, oxides of alkaline earth metals halides of alkaline earth metals, oxides of rare earth metals, halides of rare earth metals, organic complexes of alkali metals, organic complexes of alkaline earth metals and organic complexes of rare earth metals.

The specific examples of the reducing dopant include at least one alkali metal selected from the group consisting of Na (work function: 2.36 eV), K (work function: 2.28 eV), Rb (work function: 2.16 eV) and Cs (work function: 1.95 eV) and at least one alkaline earth metal selected from the group consisting of Ca (work function: 2.9 eV), Sr (work function: 2.0 to 2.5 eV) and Ba (work function: 2.52 eV), and the substances having a work function of 2.9 eV or less are particularly preferred. Among them the more preferred reducing dopant is at least one alkali metal selected from the group consisting of K, Rb and Cs and it is more preferably Rb or Cs. It is most preferably Cs. The above alkali metals have a particularly high reducing ability, and addition of a relatively small amount thereof to the electron injecting zone makes it possible to raise a light emitting luminance in the organic EL device and extend a lifetime thereof. The combination of two or more kinds of the above alkali metals is preferred as the reducing dopant having a work function of 2.9 eV or less, and particularly preferred is the combination containing Cs, for example the combination of Cs with Na, Cs with K, Cs with Rb or Cs with Na and K. Containing Cs in combination makes it possible to efficiently exhibit the reducing ability, and addition thereof to the electron injecting zone makes it possible to enhance a light emitting luminance in the organic EL device and extend a lifetime thereof.

In the organic EL device of the present invention, an electron injecting layer constituted from an insulator and a semiconductor may further be provided between the cathode and the organic layer. This makes it possible to effectively prevent

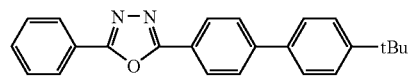

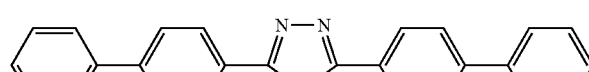

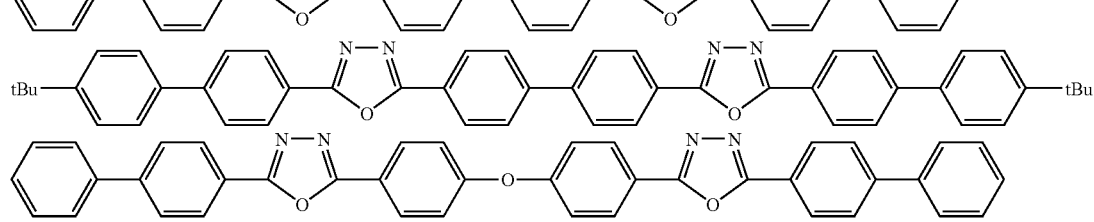

an electric current from leaking to enhance the electron injecting property. Preferably used as the above insulator is at least one metal compound selected from the group consisting of alkali metal chalcogenides, alkaline earth metal chalcogenides, halides of alkali metals and halides of alkaline earth metals. The electron injecting layer is preferably constituted from the above alkali metal chalcogenides and the like because the electron injecting property can further be enhanced. To be specific, the preferred alkali metal chalcogenides include, for example, $Li_2O$, TiO, $Na_2S$, $Na_2Se$ and NaO, and the preferred alkaline earth metal chalcogenides include, for example, CaO, BaO, SrO, Bee, BaS and CaSe. Also, the preferred halides of alkali metals include, for example, LiF, NaF, KF, LiCl, KCl and NaCl. Further, the preferred halides of alkaline earth metals include, for example, fluorides such as $CaF_2$, $BaF_2$, $SrF_2$, $MgF_2$ and $BeF_2$ and halides other than the fluorides.

The semiconductor constituting the electron injecting layer includes one kind alone of oxides, nitrides or nitride oxides containing at least one element of Bag Ca, Sr, Yb, Al, Ga, In, Li, Na, Cd, Mg, Si, Ta, Sb and Zn or combinations of two or more kinds thereof. The inorganic compound constituting the electron injecting layer is preferably a microcrystalline or amorphous insulating thin film. If the electron injecting layer is constituted from the above insulating thin film the more homogeneous thin film is formed, and therefore pixel defects such as dark spots can be reduced. The above inorganic compound includes the alkali metal chalcogenides, the alkaline earth metal chalcogenides, the halides of alkali metals and the halides of alkaline earth metals each described above.

(7) Cathode

Cathodes prepared by using metals, alloys, electroconductive compounds and mixtures thereof each having a small work function (4 eV or less) for electrode materials are used as the cathode in order to inject electrons into the electron injecting and transporting layer or the light emitting layer. The specific examples of the above electrode materials include sodium, sodium-potassium alloys, magnesium, lithium magnesium-silver alloys, aluminum/aluminum oxide, aluminum lithium alloys, indium and rare earth metals.

The above cathode can be prepared by forming a thin film from the above electrode materials by a method such as vapor deposition, sputtering and the like.

In this respect, when light emitted from the light emitting layer is taken out from the cathode, a light transmittance of the cathode based on the light emitted is preferably larger than 10%

A sheet resistance of the cathode is preferably several hundred Ω/square or less, and a film thickness thereof is usually 10 nm to 1 μm, preferably 50 to 200 nm.

(8) Insulating Layer

The organic EL device is liable to cause pixel defects by leak and short. In order to prevent this, an insulating thin film layer is preferably interposed between a pair of the electrodes.

A material used for the insulating layer includes, for example, aluminum oxide, lithium fluoride, lithium oxide, cesium fluoride, cesium oxide, magnesium oxide, magnesium fluoride, calcium oxide, calcium fluoride, aluminum nitride, titanium oxide, silicon oxide, germanium oxide, silicon nitride, boron nitride, molybdenum oxide, ruthenium oxide, vanadium oxide and the like, and mixtures and laminates thereof may be used as well.

(9) Production Process for Organic EL Device

According to the materials and the forming methods which have been shown above as the examples, the anode, the light emitting layer, if necessary, the hole injecting and transporting layer and, if necessary, the electron injecting and transporting layer are formed, and further the cathode is formed, whereby the organic EL device can be prepared. Also, the organic EL device can be prepared as well in an order of from the cathode to the anode which is reverse to the order described above.

A preparation example of an organic EL device having a structure in which an anode/a hole injecting layer/a light emitting layer/an electron injecting layer a cathode are provided in order on a light transmitting substrate shall be described below.

First, a thin film comprising an anode material is formed on a suitable light transmitting substrate by a method such as vapor deposition, sputtering and the like so that a film thickness falling in a range of 1 μm or less, preferably 10 to 200 nm is obtained, whereby an anode is prepared. Next, a hole injecting layer is provided on the above anode. The hole injecting layer can be formed, as described above, by a method such as a vacuum vapor deposition method, a spin coating method, a casting method, an LB method and the like, and it is formed preferably by the vacuum vapor deposition method from the viewpoints that the homogeneous film is liable to be obtained and that pinholes are less liable to be produced. When forming the hole Infecting layer by the vacuum vapor deposition method, the depositing conditions thereof are varied according to the compounds used (materials for the hole injecting layer), the crystal structure of the targeted hole injecting layer and the recombination structure, and in general, they are suitably selected preferably in the ranges of a depositing source temperature of 50 to 450° C., a vacuum degree of $10^{-7}$ to $10^{-3}$ torr, a depositing speed of 0.01 to 50 nm/seconds a substrate temperature of −50 to 300° C. and a film thickness of 5 nm to 5 μm.

Next, a light emitting layer can be formed on the hole injecting layer by making a thin film from the desired organic light emitting material by a method such as a vacuum vapor deposition method, sputtering, a spin coating method, a casting method and the like, and it is formed preferably by the vacuum vapor deposition method from the viewpoints that the homogeneous film is liable to be obtained and that pinholes are less liable to be produced. When forming the light emitting layer by the vacuum vapor deposition method, the depositing conditions thereof are varied according to the compounds used, and in general, they can be selected from the same condition ranges as in the hole injecting layer.

Next, an electron injecting layer is provided on the above light emitting layer. It is formed preferably by the vacuum vapor deposition method as is the case with the hole injecting layer and the light emitting layer since the homogeneous film has to be obtained. The depositing conditions thereof can be selected from the same condition ranges as in the hole injecting layer and the light emitting layer.

If the vacuum vapor deposit-on method is employed, the anthracene derivative of the present invention can be codeposited together with the other materials, though it depends on which layer, in the light emitting zone and the hole transporting zone, contains the anthracene derivative of the present invention. When using the spin coating method, it can be added by mixing with the other materials.

Lastly, a cathode is laminated whereby an organic EL device can be obtained.

The cathode is constituted from metal, and therefore the vapor deposition method and the sputtering method can be used. However, the vacuum vapor deposition method is preferred in order to protect the organic substance layer of the base from being damaged in making the film.

The above organic EL device is preferably prepared serially from the anode up to the cathode in one vacuuming.

The forming methods of the respective layers in the organic EL device of the present invention shall not specifically be restricted, and forming methods carried out by a vacuum vapor deposition method and a spin coating method which have so far publicly been known can be used. The organic thin film layer containing the anthracene derivative of the present invention which is used for the organic EL device of the present invention can be formed by a publicly known method carried out by a coating method such as a vacuum vapor deposition method, a molecular beam evaporation method (MBE method), a dipping method using a solution prepared by dissolving the compound in a solvent, a spin coating method, a casting method, a bar coating method and a roll coating method.

The film thicknesses of the respective organic layers in the organic EL device of the present invention shall not specifically be restricted, and in general, if the film thicknesses are too small defects such as pinholes are liable to be caused. On the other hand, if they are too large, high voltage has to be applied, and the efficiency is deteriorated, so that they fall preferably in a range of several nm to 1 μm.

When applying a direct voltage to the organic EL device, light emission can be observed by applying a voltage of 5 to 40 V setting a polarity of the anode to plus and that of the cathode to minus. An electric current does not flow by applying a voltage at a reverse polarity, and light emission is not caused at all. Further, when applying an AC voltage, uniform light emission can be observed only when the anode has a plus polarity and the cathode has a minus polarity. A waveform of an alternating current applied may be optional.

EXAMPLES

Next, the present invention shall be explained in further details with reference to examples.

Synthetic Example 1 synthesis of 9,10-diphenyl-2-(6-phenylpyridine-2-yl)anthracene (compound 1)

A compound 1 shown below was synthesized by the following reaction process:

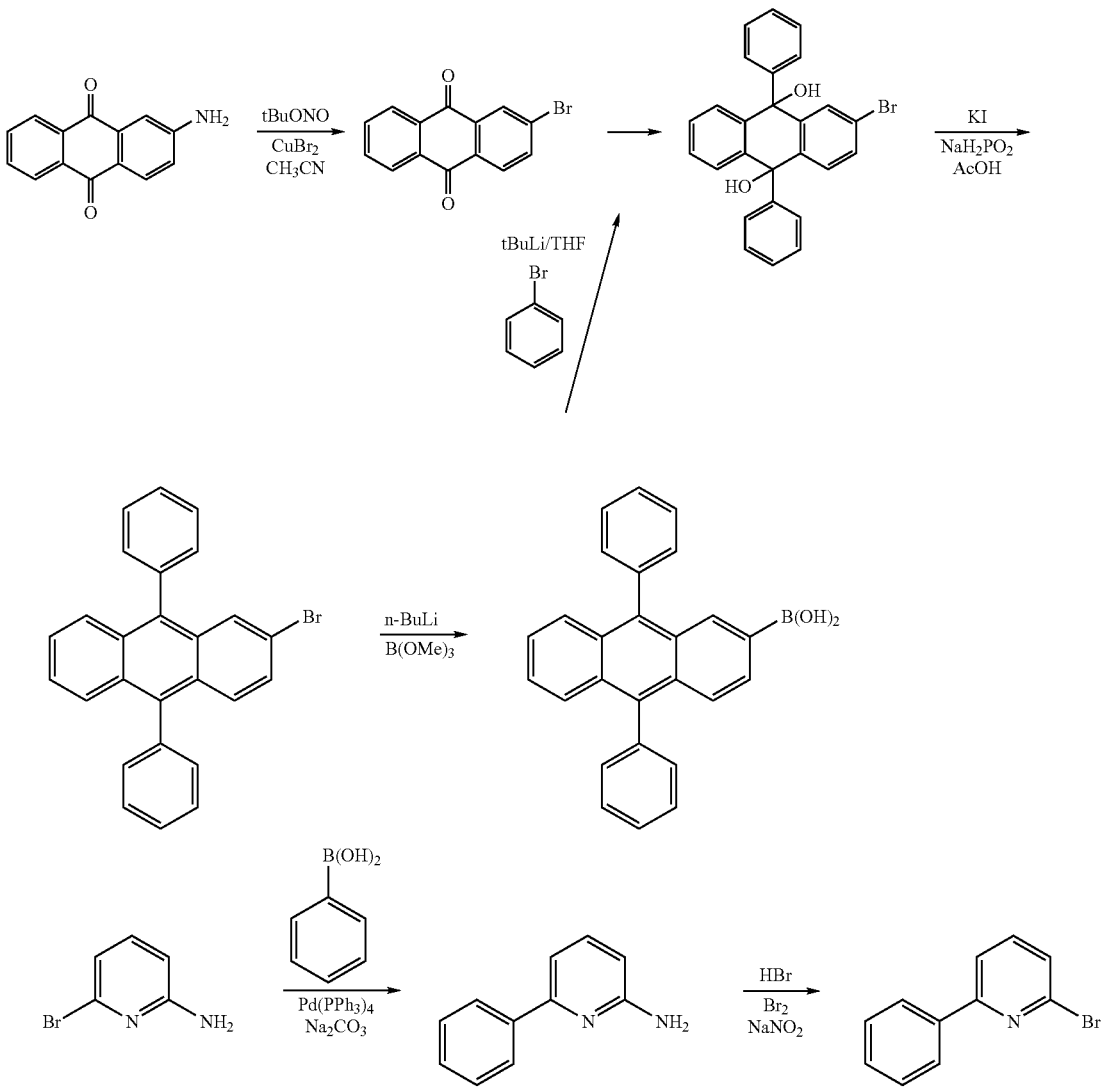

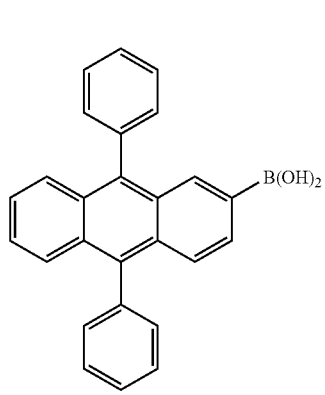 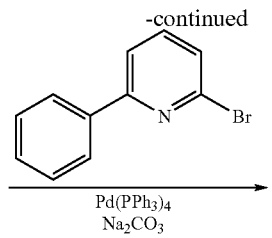 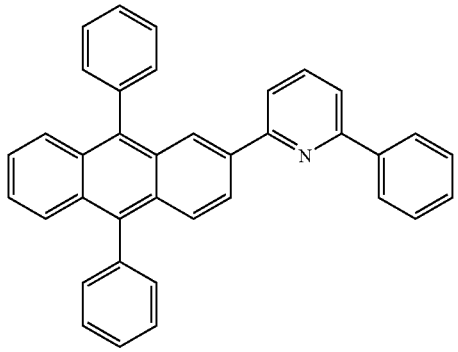

Compound 1

(1-a) Synthesis of 2-bromoanthraquinone

Copper bromide 18 g (81 mmol) and t-butyl nitrite 12 mL (101 mmol) were dispersed in acetonitrile of 65° C., and 15 g (67 mmol) of 2-aminoanthraquinone was dropwise added thereto while vigorously stirring. The solution was stirred until gas was not discharged and cooled down to room temperature, and 20% hydrochloric acid (1 L) was added thereto, followed by extracting the solution with dichloromethane. The organic layer was dried on magnesium sulfate, and the solvent was removed by distillation under reduced pressure. The residue was refined by silica gel chromatography to obtain 14 g (yield 75%) of 2-bromoanthraquinone.

(1-b) Synthesis of 2-bromo-9,10-diphenyl-9,9,10,10-tetrahydroanthracene-9,10-diol Bromobenzene 5.4 mL (52 mmol) was dissolved in 100 mL of dehydrated tetrahydrofuran under argon atmosphere and cooled down to −78° C., and 45 mL of t-butyllithium (in 1.5M pentane) was dropwise added thereto. After stirring at −78° C. for one hour, 4.9 g (17 mmol) of 2-bromoanthraquinone was added thereto. An ammonium chloride aqueous solution was added thereto, and then the solution was extracted with dichloromethane. The organic layer was dried on magnesium sulfate, and the solvent was removed by distillation under reduced pressure. A solid matter thus obtained was washed with ethanol to obtain 6.8 g (yield: 90%) of 2-bromo-9,10-diphenyl-9,9,10,10-tetrahydroanthracene-9,10-diol.

(1-c) Synthesis of 2-bromo-9,10-diphenylanthracene

2-Bromo-9,10-diphenyl-9,9,10,10-tetrahydroanthracene-9,10-diol 4.5 g (10 mmol) was dissolved in acetic acid under argon atmosphere, and 17 g (102 mmol) of potassium iodide and 18 g (167 mmol) of $NaH_2PO_2$ were added thereto. The mixture was refluxed for 3 hours by heating while stirring vigorously. It was cooled down to room temperature and then filtered. A solid matter thus obtained was washed with water and ethanol and then dried under reduced pressure to obtain 3.5 g (yield: 85%) of 2-bromo-9,10-diphenylanthracene.

(1-d) Synthesis of 9,10-diphenylanthracene-2-boronic acid

Dehydrated THF 50 mL was added to 3.5 g (8.6 mmol) of 2-bromo-9,10-diphenylanthracene under argon atmosphere and cooled down to −78° C., and 6.0 mL of n-butyllithium (in 1.6M hexane) was dropwise added thereto. After stirring at −78° C. for one hour, the temperature was elevated up to 0° C. The solution was cooled down again to −78° C., and 2.9 mL (26 mmol) of trimethoxyborane was dropwise added thereto. The solution was stirred at −78° C. for one hour and then stirred at room temperature for 2 hours. 10% HCl 50 mL was added thereto, and the solution was stirred for one hour and then filtered. The solid matter thus obtained was washed with toluene to obtain 2.6 g (yield: 80%) of 9,10-diphenylanthracene-2-boronic acid.

(1-e) Synthesis of 2-amino-6-phenylpyridine

2-Amino-6-bromopyridine 10 g (58 mmol), phenylboronic acid 8.5 g (70 mmol) and tetrakis(triphenylphosphine)palladium 1.3 g (1.2 mmol) were dissolved in 60 mL of 1,2-dimethoxyethane. A 2.0M sodium carbonate aqueous solution 30 mL was added thereto, and the solution was refluxed for 8 hours under argon atmosphere by heating. After finishing the reaction, the aqueous layer was removed. The organic layer was dried on anhydrous magnesium sulfate, and the solvent was removed by distillation under reduced pressure. The residue was refined by silica gel chromatography to obtain 6.9 g (yield: 70%) of 2-amino-6-phenylpyridine.

(1-f) Synthesis of 2-bromo-6-phenylpyridine

48% HBr 50 mL was added to 6.9 g (40 mmol) of 2-amino-6-phenylpyridine and stirred. The solution was cooled down to −20° C., and 7.7 g (48 mmol) of bromine was dropwise added thereto. Further, 2.8 g (40 mmol) of sodium nitrite was dropwise added thereto. The solution was stirred for 3 hours while elevating the temperature up to room temperature. After finishing the reaction, the solution was extracted with ethyl acetate, and the aqueous layer was removed. The organic layer was dried on anhydrous magnesium sulfate, and the solvent was removed by distillation under reduced pressure. The residue was refined by silica gel chromatography to obtain 7.5 g (yield: 80%) of 2-bromo-6-phenylpyridine.

(1-g) Synthesis of 9,10-diphenyl-2-(6-phenylpyridine-2-yl)anthracene (compound 1)

2-Bromo-6-phenylpyridine 2.5 g (11 mmol), 9,10-diphenylanthracene-2-boronic acid 4.9 g (13 mmol) and tetrakis(triphenylphosphine)palladium 0.25 g (0.22 mmol) were dissolved in 60 mL of 12-dimethoxyethane. A 2.0M sodium carbonate aqueous solution 30 mL was added thereto, and the solution was refluxed for 8 hours under argon atmosphere by heating. After finishing the reaction, the solution was filtered, and a solid matter obtained was washed with water, methanol and toluene to obtain 4.5 g (yield: 84%) of a greenish white solid matter. Mass spectral analysis of the above solid matter resulted in confirming that the measured value m/e was 483 versus a molecular weight of 483.20 and that it was the aimed compound 1

Synthetic Example 2 synthesis of 9,0-diphenyl-2-(4,6-diphenylpyrimidine-2-yl)anthracene (compound 2)

A compound 2 shown below was synthesized by the following reaction process:

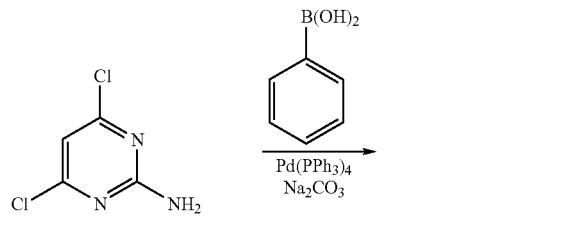

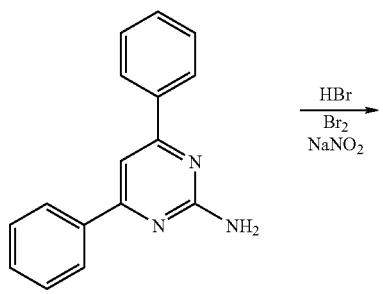

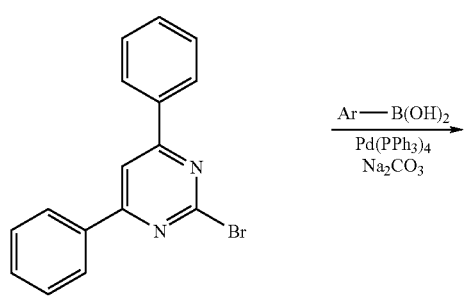

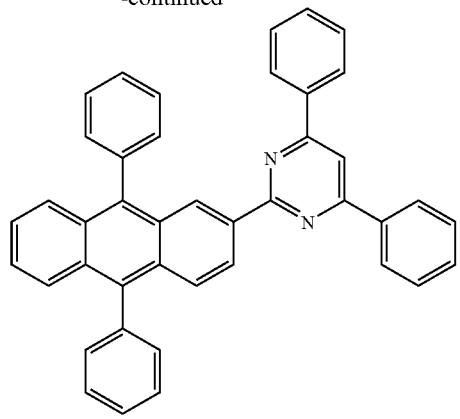

Compound 2

(2-a) Synthesis of 2-amino-4,6-diphenylpyrimidine

2-Amino-4,6-dichloropyrimidine 9.5 g (58 mmol), phenylboronic acid 17 g (140 mmol) and tetrakis(triphenylphosphine)palladium 2.7 g (2.3 mmol) were dissolved in 120 mL of 1,2-dimethoxyethane. A 2.0M sodium carbonate aqueous solution 60 mL was added thereto, and the solution was refluxed for 8 hours under argon atmosphere by heating. After finishing the reaction, the aqueous layer was removed. The organic layer was dried on anhydrous magnesium sulfate, and the solvent was removed by distillation under reduced pressure. The residue was refined by silica gel chromatography to obtain 11 g (yield: 77%) of 2-amino-4,6-diphenylpyrimidine.

(2-b) Synthesis of 2-bromo-4,6-diphenylpyrimidine

48% HBr 50 mL was added to 11 g (44 mmol) of 2-amino-4,6-diphenylpyrimidine and stirred. The solution was cooled down to −20° C., and 8.5 g (53 mmol) of bromine was dropwise added thereto. Further, 3.1 g (44 mmol) of sodium nitrite was dropwise added thereto. The solution was stirred for 3 hours while elevating the temperature up to room temperature. After finishing the reaction, the solution was extracted with ethyl acetate, and the aqueous layer was removed. The organic layer was dried on anhydrous magnesium sulfate, and the solvent was removed by distillation under reduced pressure. The residue was refined by silica gel chromatography to obtain 11 g (yield: 82%) of 2-bromo-4,6-diphenylpyrimidine.

(2-c) Synthesis of 9,10-diphenyl-2-(4,6-diphenylpyrimidine-2-yl)anthracene (compound 2)

2-Bromo-4,6-diphenylpyrimidine 3.4 g (11 mmol), 9,10-diphenylanthracene-2-boronic acid 4.9 g (13 mmol) and tetrakis(triphenylphosphine)palladium 0.25 g (0.22 mmol) were dissolved in 60 mL of 1,2-dimethoxyethane. A 2.0M sodium carbonate aqueous solution 30 mL was added thereto, and the solution was refluxed for 8 hours under argon atmosphere by heating. After finishing the reaction, the solution was filtered, and a solid matter obtained was washed with water, methanol and toluene to obtain 5.3 g (yield: 86%) of a greenish white solid matter. Mass spectral analysis of the above solid matter resulted in confirming that m/e was 560 versus a molecular weight of 560.23 and that it was the aimed compound 2.

Synthetic Example 3 synthesis of 9,10-diphenyl-2-(4,6-diphenyltriazine-2-yl)anthracene (compound 3)

A compound 3 shown below was synthesized by the following reaction step:

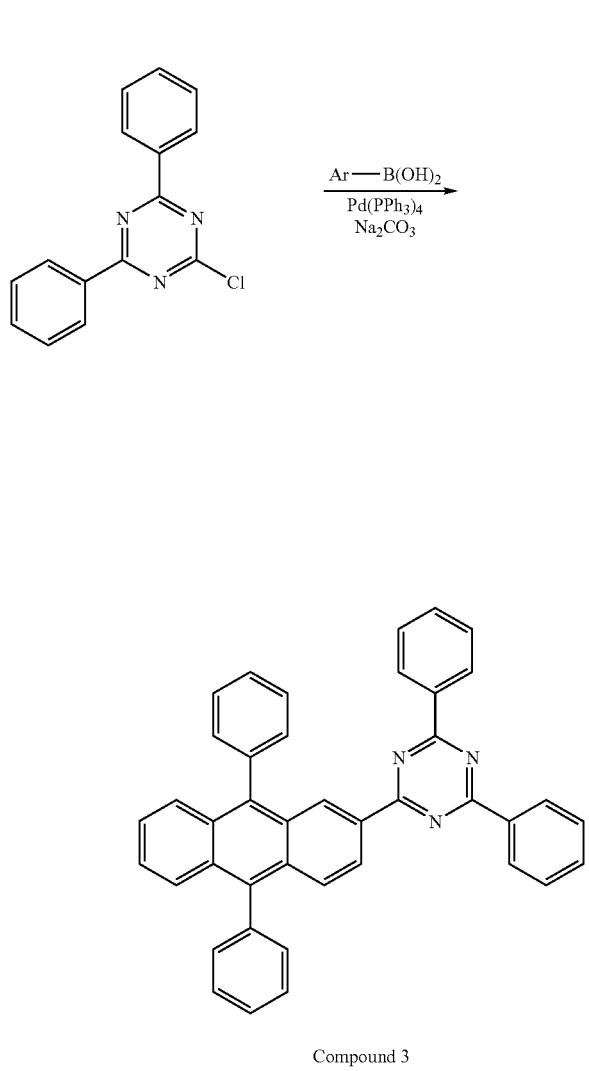

Compound 3

2-Chloro-4,6-diphenyl-1,3,5-triazine was synthesized by a publicly known synthetic process described in Japanese Patent No. 3067878. 2-Chloro-4,6-diphenyl-1,3,5-triazine 2.9 g (11 mmol), 9,10-diphenylanthracene-2-boronic acid 4.9 g (13 mmol) and tetrakis(triphenylphosphine)palladium 0.25 g (0.22 mmol) were dissolved in 60 mL of 1,2-dimethoxyethane. A 2.0M sodium carbonate aqueous solution 30 mL was added thereto, and the solution was refluxed for 8 hours under argon atmosphere by heating. After finishing the reaction, the solution was filtered, and a solid matter obtained was washed with water, methanol and toluene to obtain 5.3 g (yield: 86%) of a greenish white solid matter. Mass spectral analysis of the above solid matter resulted in confirming that m/e was 560 versus a molecular weight of 560.23 and that it was the aimed compound 3.

Synthetic Example 4 synthesis of 9,10-diphenyl-2-[4-(2,6-diphenylpyridine-4-yl)phenyl]anthracene (compound 4)

A compound 4 shown below was synthesized by the following reaction process:

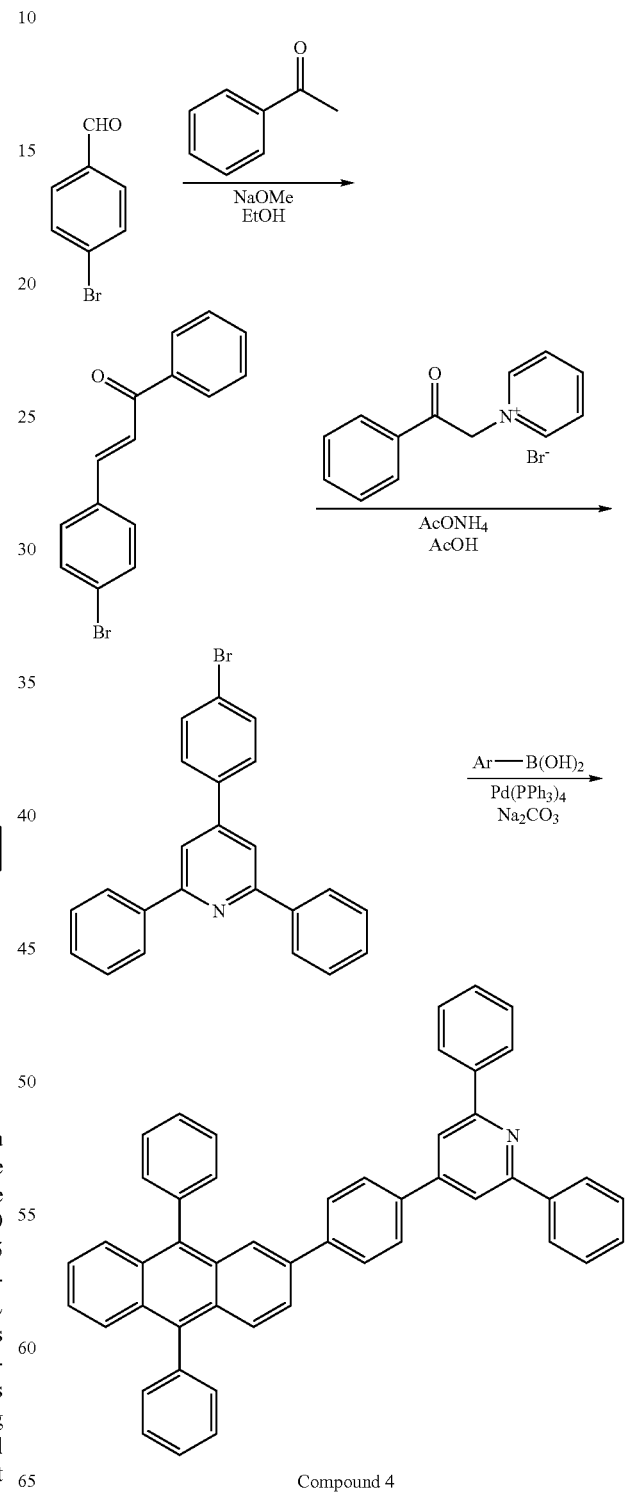

Compound 4

(4-a) Synthesis of 4-bromophenyl-2,6-diphenylpyridine

4-Bromobenzaldehyde 15.0 g (81 mmol) and acetophenone 9.7 g (81 mmol) were dissolved in 300 ml of ethanol, and 16.6 ml (81 mmol) of a 28% sodium methoxide methanol solution was added thereto and stirred a room temperature for 9 hours. After finishing the reaction, crystal deposited was filtered and washed with ethanol to obtain 19.6 g (yield: 84%) of a synthetic intermediate (enone).

The synthetic intermediate (enone) 9.0 g 31 mmol), 1-phenacylpyridinium bromide 8.7 g (31 mmol) and ammonium acetate 19.3 g (25 mmol) were suspended in 27 ml of acetic acid and refluxed for 12 hours by heating. The reaction solution was cooled down to room temperature, and toluene and water were added thereto to separate the solution into two layers. Then, the organic layer was washed in order with a 10% sodium hydroxide aqueous solution and a saturated saline solution and dried on anhydrous sodium sulfate. After removing the organic solvent by distillation under reduced pressure, 27 ml of ethanol was added thereto, and deposited crystal was filtered and washed with ethanol to obtain 10.6 g (yield: 88%) of 4-bromophenyl-2,6-diphenylpyridine.

(4-b) Synthesis of 9,10-diphenyl-2-[4-(2,6-diphenylpyridine-4-yl)phenyl]anthracene (compound 4)

4-(4-Bromophenyl)-2,6-diphenylpyridine 4.2 g (11 mmol), 9,10-diphenylanthracene-2-boronic acid 4.9 g (13 mmol) and tetrakis(triphenylphosphine)palladium 0.21 g (0.22 mmol) were dissolved in 60 mL of 1,2-dimethoxyethane. A 2.0M sodium carbonate aqueous solution 30 mL was added thereto, and the solution was refluxed for 8 hours under argon atmosphere by heating. After finishing the reaction, the solution was filtered, and a solid matter obtained was washed with water, methanol and toluene to obtain 5.8 g (yield: 83%) of a greenish white solid matter. Mass spectral analysis of the above solid matter resulted in confirming that m/e was 635 versus a molecular weight of 635.26 and that it was the aimed compound 4.

Synthetic Example 5 synthesis of 9,10-diphenyl-2-[4-(2,6-diphenylpyrimidine-4-yl)phenyl]anthracene (compound 5)

A compound 5 shown below was synthesized by the following reaction process:

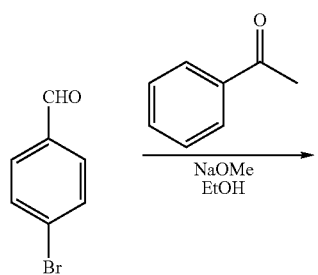

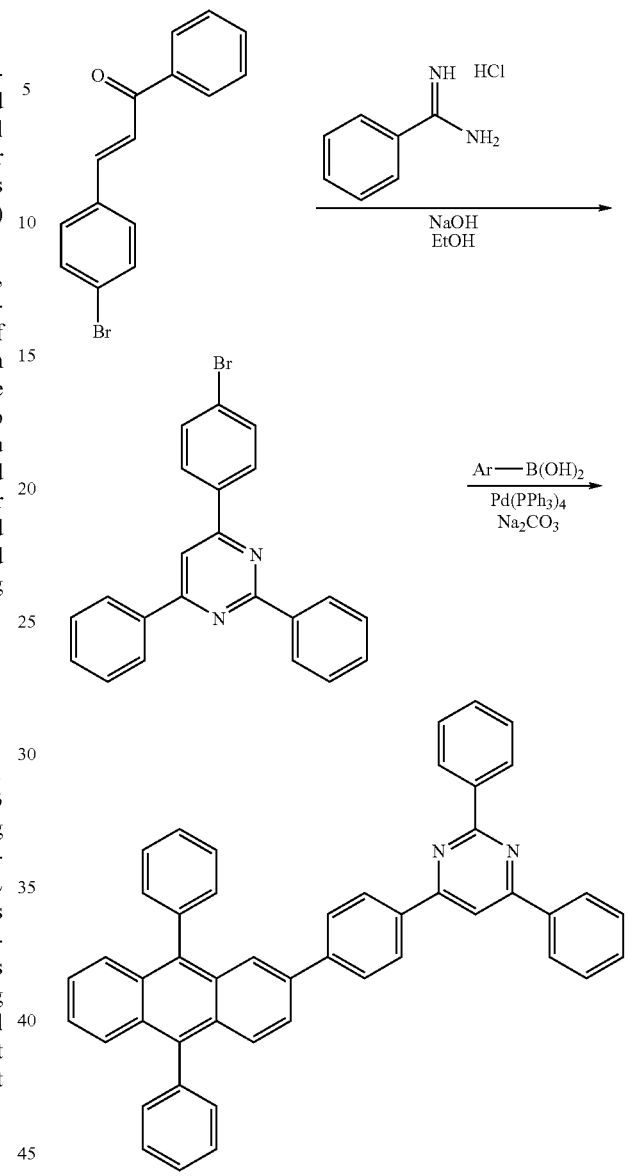

Compound 5

(5-a) Synthesis of 4-(4-bromophenyl)-2,6-diphenylpyrimidine

4-Bromoacetophenone 19.9 g (100 mmol) and benzaldehyde 10.6 g (100 mmol) were mixed and, the system was substituted with argon. Next, 200 mL of ethanol and 10 MeI of a 1N sodium methoxide/methanol solution were added thereto and stirred at room temperature for 5 hours. Thereafter, the solution was heated on an oil bath of 70° C. to carry out reaction for further 4 hours while refluxing ethanol. Then, benzamidine hydrochloride 9.40 g (60 mmol) and sodium hydroxide 8.00 g (200 mmol) were added thereto and heated on the oil bath of 70° to carry out reaction for 5 hours. After finishing the Reactions the deposit was separated by filtering and refined by silica gel chromatography to obtain 13.6 g (yield: 35%) of 4-(4-bromophenyl)-2,6-diphenylpyrimidine.

(5-b) Synthesis of 9,10-diphenyl-2-[4-(2,6-d-phenylpyrimidine-4-yl)phenyl]anthracene (compound 5)

4-(4-Bromophenyl)-2,6-d phenylpyrimidine 4.3 g (11 mmol), 9,10-diphenylanthracene-2-boronic acid 4.9 g (13 mmol) and tetrakis(triphenylphosphine)palladium 0.25 g (0.22 mmol) were dissolved in 60 mL of 1,2-dimethoxyethane. A 2.0M sodium carbonate aqueous solution 30 mL was added thereto, and the solution was refluxed for 8 hours under argon atmosphere by heating. After finishing the reaction, the solution was filtered, and a solid matter obtained was washed with water, methanol and toluene to obtain 5.3 g (yield: 76%) of a greenish white solid matter. Mass spectral analysis of the above solid matter resulted in confirming that m/e was 636 versus a molecular weight of 636.26 and that it was the aimed compound 5.

Synthetic Example 6

(synthesis of 9,10-diphenyl-2-[4-(4,6-diphenyl-1,3,5-triazine-2-yl)phenyl]anthracene (compound 6)

A compound 6 shown below was synthesized by the following reaction process:

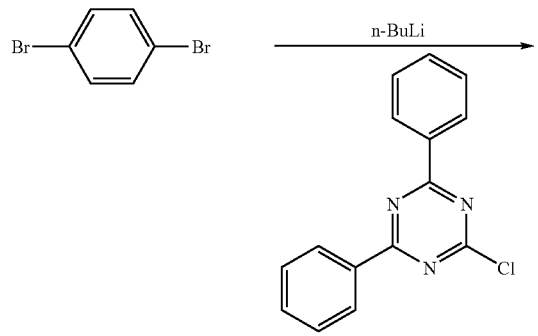

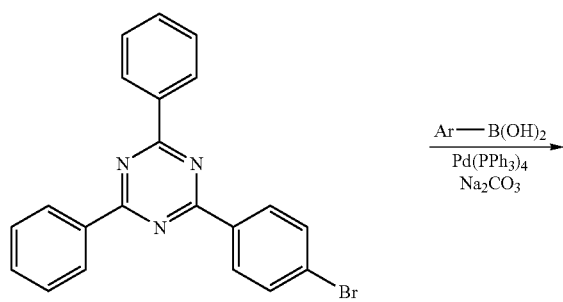

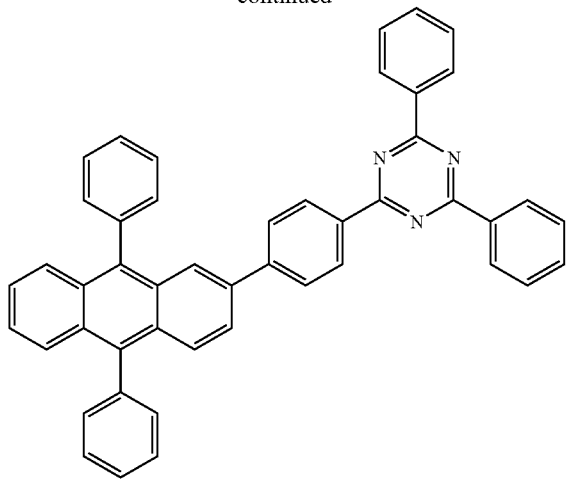

Compound 6

(6-a) Synthesis of 2-(4-bromophenyl)-4,6-diphenyl-1,3,5-triazine 1,4-Dibromobenzene 2.64 g (11.2 mmol) was dissolved in 30 mL of dried tetrahydrofuran and cooled down to −70° C. A hexane solution (1.6M) 7.4 mL (11.8 mmol) was dropwise added slowly to the above solution and stirred at −70° C. for 30 minutes. A tetrahydrofuran solution of 2-chloro-4,6-diphenyl-1,3,5-triazine 3.00 g (11.2 mmol) was dropwise added to the above mixture at −70° and stirred at −70° C. for 30 minutes, and then the solution was heated slowly up to room temperature and stirred further for 1.5 hour. The mixture thus obtained was extracted with ethyl acetate, and the organic layer was washed in order with water and a saturated saline solution and dried on anhydrous magnesium sulfate. Then, the solvent was removed by distillation, and the residue was refined by silica gel chromatography to thereby obtain 1.48 g (yield: 34%) of 2-(4-bromophenyl)-4,6-diphenyl-1,3,5-triazine.

(6-b) Synthesis of 9,10-diphenyl-2-[4-(4,6-diphenyl-1,3,5-triazine-2-yl)phenyl]anthracene (compound 6)

2-(4-Bromophenyl)-4,6-diphenyl-1,3,5-triazine 4.3 g (11 mmol), 9,10-diphenylanthracene-2-boronic acid 4.9 g (13 mmol) and tetrakis(triphenylphosphine)palladium 0.25 g (0.22 mmol) were dissolved in 60 mL of 1,2-dimethoxyethane. A 2.0M sodium carbonate aqueous solution 30 mL was added thereto, and the solution was refluxed for 8 hours under argon atmosphere by heating. After finishing the reaction, the solution was filtered, and a solid matter obtained was washed with water, methanol and toluene to obtain 5.6 g (yield: 80%) of a greenish white solid matter. Mass spectral analysis of the above solid matter resulted in confirming that m/e was 637 versus a molecular weight of 637.25 and that it was the aimed compound 6.

Example 1

A glass substrate (manufactured by Geomatech Co., Ltd.) of 25 mm×75 mm×1.1 mm thickness equipped with an ITO transparent electrode was subjected to supersonic wave washing in isopropyl alcohol for 5 minutes and then to UV ozone washing for 30 minutes. After washed, the glass substrate equipped with the transparent electrode line was loaded in a substrate holder of a vacuum vapor deposition apparatus, and an N,N'-bis(N,N'-diphenyl-4-aminophenyl)-N,N-diphenyl-4,4'-diamino-1,1'-biphenyl film (TPD 232 film) having a film thickness of 60 nm was formed by resistance heating vapor deposition on a face of a side at which the transparent electrode line was formed so that it covered the transparent electrode described above. The above TPD 232 film functions as a first hole injecting layer (or a hole transporting layer). A 4,4"-bis[N-1-naphthyl)-N-phenylamino]biphenyl film (NPD film) having a film thickness of 20 nm was formed on the above TPD 232 film by resistance heating vapor deposition. The above NPD film functions as a second hole injecting layer (or a hole transporting layer). Further, a film of 4',4"-bis(2,2-diphenylvinyl)-9,10-diphenylanthracene (DPVDPAN) was formed on the above NPD film in a film thickness of 40 nm by resistance heating vapor deposition. The above DPVDPAN film functions as a light emitting layer.

Further, a film of the compound 1 described above having a film thickness of 10 nm was formed on the above DPVDPAN film by vapor deposition. The above compound 1 film functions as an electron injecting layer (or an electron transporting layer). Then, Li (Li source: manufactured by Saesgetter Co., Ltd.) and the compound 1 described above were subjected to binary vapor deposition to form a compound 1:Li film having a film thickness of 10 nm as an electron injecting layer for a cathode) at a film forming speed of 1.5 Å/sec:1 Å/min. Metal Al was deposited on the above compound 1:Li film to form a metal cathode having a film thickness of 130 nm, whereby an organic EL device was formed.

An electric current was applied to the device thus obtained, and homogeneous light emission of a blue color was obtained. Further, the above device was operated at a constant electric current and an initial luminance of 300 cd/m$^2$ to find that homogeneous light emission was continued for 1000 hours or longer.

Examples 2 to 5

Organic EL devices were prepared in the same manner as Example 1, except that the compound 2 described above (Examples 2), the compound 3 described above (Examples 3), the compound 4 described above (Examples 4) and the compound 5 described above (Examples 5) were used in place of the compound 1 used in the electron injecting layer (or the electron transporting layer) and the electron injecting layer (or the cathode).

An electric current was applied to the devices thus obtained, and homogeneous light emission of a blue color was obtained. Further, the above devices were operated at a constant electric current and an initial luminance of 300 cd/m$^2$ to find that homogeneous light emission was continued for 1000 hours or longer.

Example 6

An organic EL device was prepared in the same manner as Example 1, except that the compound 1 was used in place of DPVDPAN used in the light emitting layer and that the compound 5 was used in place of the compound 1 used in the electron injecting layer (or the electron transporting layer) and the electron injecting layer (or the cathode).

An electric current was applied to the device thus obtained, and homogeneous light emission of a blue color was obtained. Further, the above device was operated at a constant electric current and an initial luminance of 300 cd/m$^2$ to find that homogeneous light emission was continued for 1000 hours or longer.

Example 7

An organic EL device was prepared in the same manner as Example 1, except that the compound 2 was used in place of DPVDPAN used in the light emitting layer and that the compound 5 was used in place of the compound 1 used in the electron injecting layer (or the electron transporting layer) and the electron injecting layer (or the cathode).

An electric current was applied to the device thus obtained, and homogeneous light emission of a blue color was obtained. Further, the above device was operated at a constant electric current and an initial luminance of 300 cd/m$^2$ to find that homogeneous light emission was continued for 1000 hours or longer.

Example 8

An organic EL device was prepared in the same manner as Example 1, except that the compound 3 was used in place of DPVDPAN used in the light emitting layer and that the compound 5 was used in place of the compound 1 used in the electron injecting layer (or the electron transporting layer) and the electron injecting layer (or the cathode).

An electric current was applied to the device thus obtained, and homogeneous light emission of a blue color was obtained. Further, the above device was operated at a constant electric current and an initial luminance of 300 cd/m$^2$ to find that homogeneous light emission was continued for 1000 hours or longer.

Example 9

An organic EL device was prepared in the same manner as Example 1, except that the compound 4 was used in place of DPVDPAN used in the light emitting layer and that the compound 5 was used in place of the compound 1 used in the electron Injecting layer (or the electron transporting layer) and the electron injecting layer (or the cathode).

An electric current was applied to the device thus obtained and homogeneous light emission of a blue color was obtained. Further, the above device was operated at a constant electric current and an initial luminance of 300 cd/m$^2$ to find that homogeneous light emission was continued for 1000 hours or longer.

Comparative Examples 1 to 2

Organic EL devices were prepared in the same manner as Example 1, except that a compound A shown below (Comparative Example 1) and a compound B shown below (Comparative Example 2) were used in place of the compound 1 used in the electron injecting layer (or the electron transporting layer) and the electron injecting layer (or the cathode).

The device obtained in Comparative Example 1 was operated at a constant electric current and an initial luminance of 300 cd/m$^2$ to find that light emission of the device prepared in Comparative Example 1 was reduced by half in 100 hours and confirm that a lot of dark spots were present.

Further, the device obtained in Comparative Example 2 was operated at a constant electric current and an initial luminance of 300 cd/m$^2$ to find that light emission of the device prepared in Comparative Example 2 was reduced by half in 10 hours and confirm that a lot of dark spots were present.

Compound A

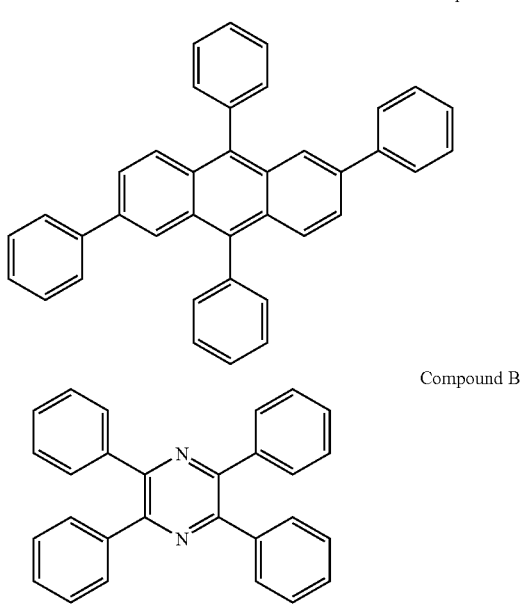

Compound B

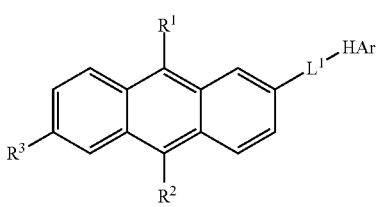

As described above, the organic EL devices prepared in Examples 1 to 9 in which the anthracene derivative of the present invention was used in an electron injecting layer are improved in an adhesive property between an electron infecting layer and a cathodes provides homogeneous light emission and can stably be operated for a long period of time.

Industrial Applicability

As explained above, the anthracene derivative of the present invention and the organic EL device prepared by using the same provide homogeneous light emission over a long period of time and have a long lifetime. Accordingly it is very useful as an organic EL device having a high practicality.

The invention claimed is:

1. An organic electroluminescence device in which an organic thin film layer comprising an electron injecting layer and/or an electron transporting layer, and a light emitting layer is interposed between a cathode and an anode, wherein the electron injecting layer and/or the electron transporting layer comprise at least one anthracene derivative represented by the following formula (1):

(1)

[structure of anthracene with substituents $R^1$, $R^2$, $R^3$, $L^1$, HAr]

wherein $R^1$ to $R^3$ each independently represent a hydrogen atom, a halogen atom, a substituted or non-substituted aliphatic hydrocarbon group having 1 to 40 carbon atoms, a substituted or non-substituted aryl group having 5 to 60 carbon atoms, or a substituted or non-substituted heteroaryl group having 3 to 60 carbon atoms, with the proviso that $R^1$ and $R^2$ do not simultaneously represent a hydrogen atom;

$L^1$ represents a single bond, a substituted or non-substituted divalent aliphatic hydrocarbon group having 1 to 40 carbon atoms, a substituted or non-substituted arylene group having 5 to 60 carbon atoms, or a substituted or non-substituted heteroarylene group having 3 to 60 carbon atoms; and HAr represents a substituted or non-substituted heteroaryl group which has 3 to 60 carbon atoms and comprises a nitrogen-containing six-membered ring.

2. The organic electroluminescence device according to claim 1, wherein the organic thin film layer comprises the electron injecting layer, and wherein the electron injecting layer comprises the anthracene derivative of formula (1).

3. The organic electroluminescence device according to claim 1, wherein the organic thin film layer comprises the electron transporting layer, and wherein the electron transporting layer comprises the anthracene derivative of formula (1).

4. The organic electroluminescence device according to claim 1, wherein the organic thin film layer comprises the electron injecting layer and the electron transporting layer, and wherein the electron injecting layer and the electron transporting layer comprise the anthracene derivative of formula (1).

5. The organic electroluminescence device according to claim 1, wherein the electron injecting layer and/or electron transporting layer further comprise a reducing dopant.

6. The organic electroluminescence device according to claim 5, wherein the reducing dopant is at least one selected from the group consisting of an alkali metal, an alkaline earth metal, a rare earth metal, an oxide of an alkali metal, a halide of an alkali metal, an oxide of an alkaline earth metal, a halide of an alkaline earth metal, an oxide of a rare earth metal, a halide of a rare earth metal, an organic complex of an alkali metal, an organic complex of an alkaline earth metal, and an organic complex of a rare earth metal.

7. The organic electroluminescence device according to claim 1, wherein HAr is a group represented by any of the following formulae:

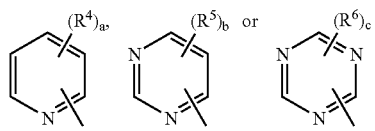

wherein $R^4$ to $R^6$ each independently represent a hydrogen atom, a halogen atom, a substituted or non-substituted aliphatic hydrocarbon group having 1 to 40 carbon atoms, a substituted or non-substituted aryl group having 5 to 60 carbon atoms, or a substituted or non-substituted heteroaryl group having 3 to 60 carbon atoms, and plural adjacent $R^4$ and $R^5$ may be combined to form a cyclic structure;

a represents an integer of 0 to 4;

b represents an integer of 0 to 3; and c represents an integer of 0 to 2.

8. The organic electroluminescence device according to claim 1, with the proviso that $R^1$ and $R^2$ do not simultaneously represent an alkoxy-substituted aryl group.

9. An organic electroluminescence device in which an organic thin film layer comprising an electron injecting layer and/or an electron transporting layer, and a light emitting layer is interposed between a cathode and an anode, wherein the electron injecting layer and/or the electron transporting layer comprise at least one anthracene derivative represented by the following formula (2):

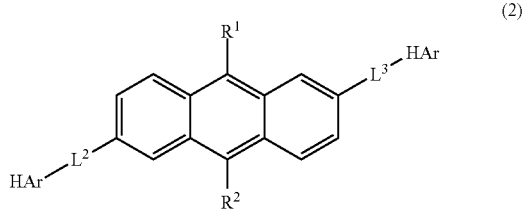

(2)

wherein $R^1$ and $R^2$ each independently represent a hydrogen atom, a halogen atom, a substituted or non-substituted aliphatic hydrocarbon group having 1 to 40 carbon atoms, a substituted or non-substituted aryl group having 5 to 60 carbon atoms, or a substituted or non-substituted heteroaryl group having 3 to 60 carbon atoms, with the proviso that $R^1$ and $R^2$ do not simultaneously represent a hydrogen atom;

$L^2$ and $L^3$ each independently represent a single bond, a substituted or non-substituted divalent aliphatic hydrocarbon group having 1 to 40 carbon atoms, a substituted or non-substituted arylene group having 5 to 60 carbon atoms, or a substituted or non-substituted heteroarylene group having 3 to 60 carbon atoms; and HAr represents a substituted or non-substituted heteroaryl group which has 3 to 60 carbon atoms and comprises a nitrogen-containing six-membered ring.

10. The organic electroluminescence device according to claim 9, wherein the organic thin film layer comprises the electron injecting layer, and wherein the electron injecting layer comprises the anthracene derivative of formula (2).

11. The organic electroluminescence device according to claim 9, wherein the organic thin film layer comprises the electron transporting layer, and wherein the electron transporting layer comprises the anthracene derivative of formula (2).

12. The organic electroluminescence device according to claim 9, wherein the organic thin film layer comprises the electron injecting layer and the electron transporting layer, and wherein the electron injecting layer and the electron transporting layer comprise the anthracene derivative of formula (2).

13. The organic electroluminescence device according to claim 9, wherein the electron injecting layer and/or electron transporting layer further comprise a reducing dopant.

14. The organic electroluminescence device according to claim 13, wherein the reducing dopant is at least one selected from the group consisting of an alkali metal, an alkaline earth metal, a rare earth metal, an oxide of an alkali metal, a halide of an alkali metal, an oxide of an alkaline earth metal, a halide of an alkaline earth metal, an oxide of a rare earth metal, a halide of a rare earth metal, an organic complex of an alkali metal, an organic complex of an alkaline earth metal, and an organic complex of a rare earth metal.

15. The organic electroluminescence device according to claim 9, wherein HAr is a group represented by any of the following formulae:

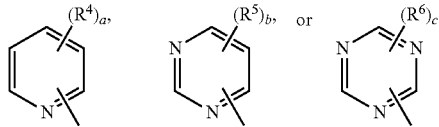

wherein $R^4$ to $R^6$ each independently represent a hydrogen atom, a halogen atom, a substituted or non-substituted aliphatic hydrocarbon group having 1 to 40 carbon atoms, a substituted or non-substituted aryl group having 5 to 60 carbon atoms, or a substituted or non-substituted heteroaryl group having 3 to 60 carbon atoms, and plural adjacent $R^4$ and $R^5$ may be combined to form a cyclic structure;

a represents an integer of 0 to 4;
b represents an integer of 0 to 3; and
c represents an integer of 0 to 2.

16. The organic electroluminescence device according to claim 9, with the proviso that $R^1$ and $R^2$ do not simultaneously represent an alkoxy-substituted aryl group.

* * * * *